(12) United States Patent
Ma et al.

(10) Patent No.: US 7,229,996 B2
(45) Date of Patent: Jun. 12, 2007

(54) RIFAMYCIN DERIVATIVES

(75) Inventors: Zhenkun Ma, Dallas, TX (US); Jing Li, Dallas, TX (US); Susan Harran, Dallas, TX (US); Yong He, Arlington, TX (US); Keith P. Minor, Dallas, TX (US); In Ho Kim, Lewisville, TX (US); Charles Z. Ding, Plano, TX (US); Jamie C. Longgood, Carrolton, TX (US); Yafei Jin, Dallas, TX (US); Keith D. Combrink, Fort Worth, TX (US)

(73) Assignee: Cumbre Pharmaceuticals Inc., Dallas, TX (US)

( * ) Notice: Subject to any disclaimer, the term of this patent is extended or adjusted under 35 U.S.C. 154(b) by 66 days.

(21) Appl. No.: 11/186,187

(22) Filed: Jul. 21, 2005

(65) Prior Publication Data

US 2006/0019985 A1    Jan. 26, 2006

Related U.S. Application Data

(60) Provisional application No. 60/590,190, filed on Jul. 22, 2004.

(51) Int. Cl.
C07D 498/08 (2006.01)
A61K 31/4709 (2006.01)
A61P 31/04 (2006.01)

(52) U.S. Cl. ............... 514/252.17; 514/278; 514/306; 540/459

(58) Field of Classification Search ............ 540/459; 514/306, 252.17, 278
See application file for complete search history.

(56) References Cited

U.S. PATENT DOCUMENTS 5,786,350 A    7/1998    Occelli et al.

FOREIGN PATENT DOCUMENTS

| WO | WO 94/28002 A1 | 12/1994 |
|---|---|---|
| WO | WO 03/045319 A2 | 6/2003 |
| WO | WO 2005/070940 A2 | 8/2005 |
| WO | WO 2005/070941 A1 | 8/2005 |

OTHER PUBLICATIONS

Farr, BM. Rifamycins, in Principles and Practice of Infectious Diseases. Mandell GL, Bennett JE, Dolin R, Eds. Churchhill Livingstone Philadelphia pp. 348-361.
Li Q, Chu DT, Claiborne, A, Cooper CS, Lee CM, Raye K, Berst KB, Donner P, Wang W, Hasvold L, Fung A, Ma Z, Tufano M, Flamm R, Shen LL, Baranowski J, Nilius A, Alder J, Meulbroek J, Marsh K, Crowell D, Hui Y, Seif L, Melcher LM, Plattner JJ, et al. Synthesis and structure-activity relationships of 2-pyridones: a novel series of potent DNA gyrase inhibitors as antibacterial agents. J Med Chem. Aug. 2, 1996;39(16):3070-88.

(Continued)

*Primary Examiner*—Bruck Kifle
(74) *Attorney, Agent, or Firm*—Jackson Walker L.L.P.

(57) ABSTRACT

Novel rifamycin derivatives of formula I (both hydroquinone and corresponding quinone ($C_1$-$C_4$) forms):

or their salts, hydrates or prodrugs thereof,
wherein: a preferred R comprises hydrogen, acetyl; L is a linker, a preferred linker group elements selected from any combination of 1 to 5 groups shown FIG. 1, provided L is not wherein $R_1$ is H, methyl or alkyl. The inventive compounds exhibit valuable antibiotic properties. Formulations having these compounds can be used in the control or prevention of infectious diseases in mammals, both humans and non-humans. In particular, the compounds exhibit a pronounced antibacterial activity, even against multiresistant strains of microbes.

8 Claims, 4 Drawing Sheets

OTHER PUBLICATIONS

Li Q, Mitscher LA, Shen LL. The 2-pyridone antibacterial agents: bacterial topoisomerase inhibitors. Med Res Rev. Jun. 2000;20(4):231-93.

Marsili L, Pasqualucci CR, Vigevani A, Gioia B, Schioppacassi G, Oronzo G. New rifamycins modified at positions 3 and 4. Synthesis, structure and biological evaluation. J Antibiol (Tokyo). Aug. 1981;34(8):1033-8.

Yamane T, Hashizume T, Yamashita K, Konishi E, Hosoe K, Hidaka T, Watanabe K, Kawaharada H, Yamamoto T, Kuze F. Synthesis and biological activity of 3'-hydroxy-5'-aminobenzoxazinorifamycin derivatives. Chem Pharm Bull (Tokyo). Jan. 1993;41(1):148-55.

PCT Notification of Transmittal of the International Search Report and the Written Opinion of the International Searching Authority, or the Declaration. Dec. 6, 2005.

Scheme B

RIFAMYCIN DERIVATIVES

This application claims benefit of application Ser. No. 60/590,190 filed Jul. 22, 2004.

BACKGROUND

This application claims priority to U.S. Provisional Patent Application Ser. No. 60/590,190, entitled "4H-4-Oxoquinolizine Derivatives Having Improved Target Selectivity," filed on Jul. 22, 2004, the entire content of which is hereby incorporated by reference.

One aspect of this invention relates to novel rifamycin derivatives having antimicrobial activity, compositions containing the compounds, and methods for treatment and prevention of microbial infections. The compounds of the current invention exhibit potent antimicrobial activity and improved activity against drug resistant bacteria. In particular, the compounds of the current invention relate to a series of rifamycins which covently linked to 4H-4-oxoquinolizine carboxylic acid and they demonstrate antibacterial activity against drug-resistant bacteria.

The compounds of the current invention are chemically designed to address drug resistance by chemically linking molecules derived from hybridization of rifamycin and 4H-4-oxoquinolizine carboxylic acid. These compounds have potent antibacterial pharmacophores joined together through a stable bivalent linker. They exhibit reduced frequency of resistance, and slow or eliminate development of drug resistance.

Rifamycins belong to a potent class of antibiotics targeting bacterial RNA polymerase. Many semi-synthetic rifamycin derivatives such as rifampin, rifabutin and rifapetine have been developed into therapeutic agents and are currently used for the treatment of tuberculosis and other microbial infections (Farr, Rifamycins). However, one of the major problems associated with the rifamycin class of antimicrobial agents is the high frequency of development of microbial resistance due to mutations in RNA polymerase. Consequently, rifamycins are currently used only in combination therapies to minimize the development of resistance to this class of drug.

Quinolones are a class of potent antimicrobial agents targeting both bacterial DNA gyrase and topoisomerase IV. These agents have been widely used clinically and are orally and parenterally active with a broad spectrum of activities covering both Gram-positive and Gram-negative pathogens. One of the major problems associated with the quinolone class is the rapid development of resistance among some common bacterial pathogens. To address the drug resistance problem, newer generations of quinolones are introduced and currently under development. A series of 4H-4-oxoquinolizine compounds are introduced recently (Li, Q.; Mitscher, L. A.; Shen, L. *Med. Res. Rev.*, 2000, 20, 231-293.). This series of compounds possess potent antimicrobial activity and improved activity against quinolone resistance.

Reference is also made to PCT application WO 03/045319 A2 that discloses rifamycin derivatives formed by linking rifamycin and a therapeutic drug and the use of these derivatives as vehicles for delivering the therapeutic drug. However, this reference failed to demonstrate by specific examples that quinolones or 4H-4-oxoquinolizine carboxylic acid is introduced to the rifamycin scaffold.

SUMMARY

The current invention relates to a compound of general formula I (either hydroquinone or corresponding quinone ($C_1$-$C_4$) forms):

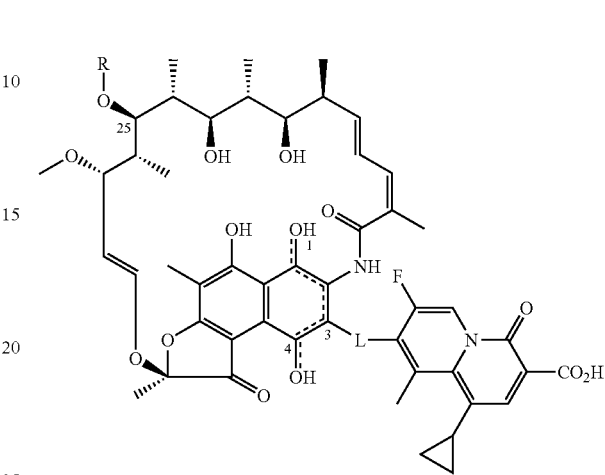

I or its salts, hydrates or prodrugs thereof, wherein: a preferred R comprises hydrogen or acetyl; L is a linker, wherein a preferred linker group is selected from any combination of 1 to 5 structural elements shown in FIG. 1, provided L is not

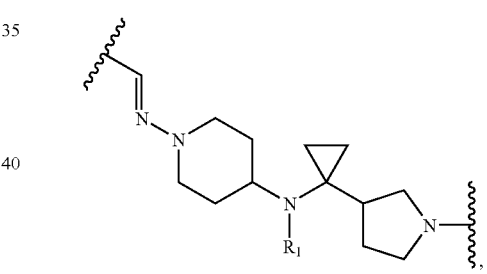

wherein $R_1$ is H, methyl or alkyl.

These compounds are novel and have valuable antibiotic properties. They can be used in the control or prevention of infectious diseases in mammals, both humans and non-humans. In particular, they exhibit a pronounced antibacterial activity, even against multiresistant strains of microbes. The compounds can also be administered in combination with known antibacterially active substances, exhibiting synergistic or additive effects. Examples are the beta-lactam class, like ceftriaxone; oxazolidinone class, like linezolid; antibacterial peptides, like vancomycin, dalbavancin, daptomycin; and polymycin B.

Another aspect of the current invention comprises a method of treating a microbial infection in a subject; wherein the subject is any species of the animal kingdom. The microbial infection can be caused by a bacterium or microorganism. The term "subject" refers more specifically to human and animals, wherein the animals are raised for: pets (e.g. cats, dogs, etc.); work (e.g. horses, cows, etc.); food (chicken, fish, lambs, pigs, etc); and all others known in the art. The method comprises administering an effective amount of one or more compounds of the present invention to the subject suffering from a microbial infection.

DETAILED DESCRIPTION OF PREFERRED EMBODIMENTS

Figure 1:
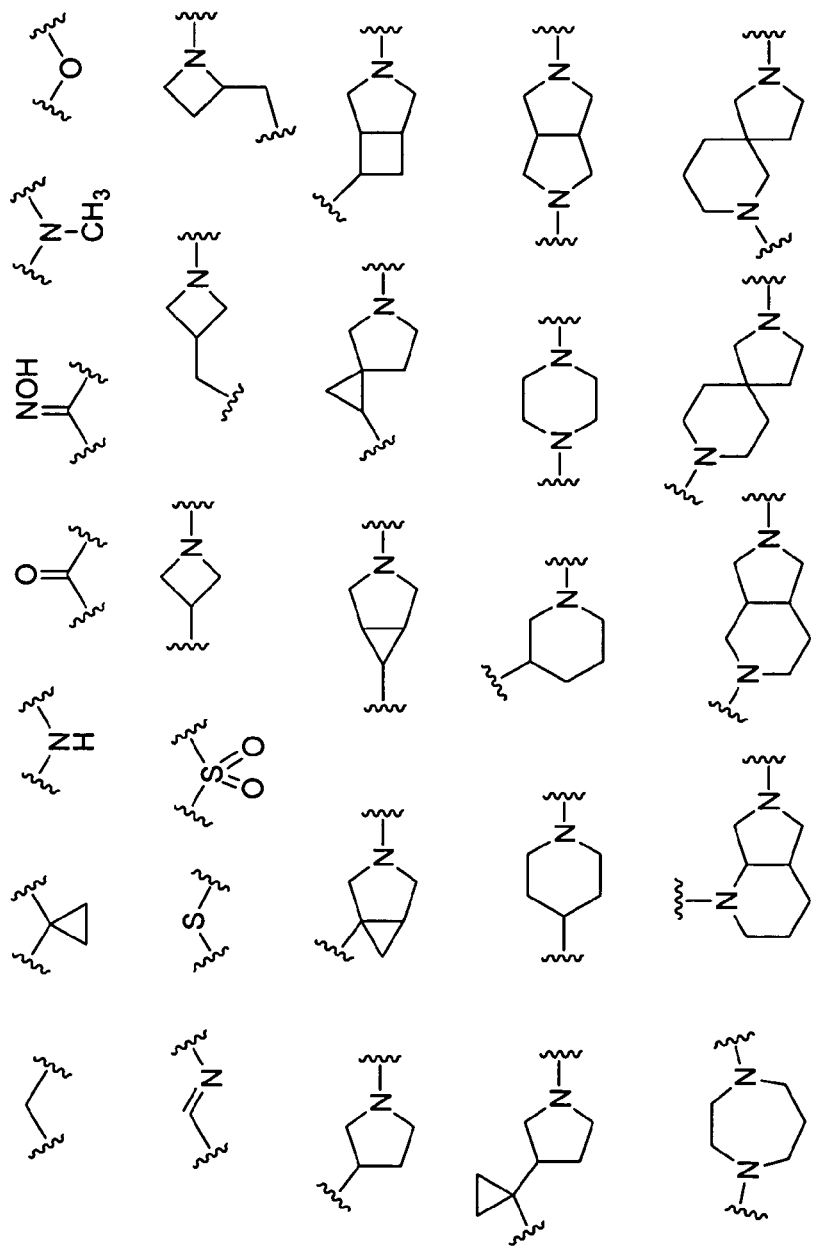
FIG. 1 shows a group of linker structural elements, which are constituents of preferred structures for L.

Terms:

The term "alkyl" as used herein, refers to a saturated, straight or branched chain hydrocarbon group. Lower alkyl group includes $C_1$ to $C_{10}$. Examples of preferred lower alkyl group include methyl, ethyl, propyl, iso-propyl, n-butyl, iso-butyl, tert-butyl, neo-pentyl, and n-hexyl. The alkyl groups of this invention can be optionally substituted with 1-3 substitutents.

The term "prodrugs," as used herein refers to the prodrugs of the compounds of the current invention which are suitable for use in humans and animals with acceptable toxicity, irritation, allergic response, and the like, commensurate with a reasonable benefit to risk ratio, and effective for their intended use. The term "prodrug," as used herein, represents compounds which can be transformed in vivo to parent compounds defined above.

The term "salt," as used herein refers to those salts which are suitable for use in humans and animals with acceptable toxicity, irritation, and allergic response, etc., and are commensurate with a reasonable benefit to risk ratio. Pharmaceutically acceptable salts are well known in the art. The salts can be prepared in situ during the final step of isolation and purification of the compounds of the invention or separately prepared by reacting the compounds of the invention with an acid or base. Examples of pharmaceutically acceptable salts are salts of an amino group formed with inorganic acids such as hydrochloric acid, hydrobromic acid, phosphoric acid, and sulfuric acid or with organic acids such as acetic acid, oxalic acid, maleic acid, tartaric acid, citric acid, succinic acid, or malonic acid. Examples of pharmaceutically acceptable salts are salts of an acid group formed with inorganic bases such as sodium hydroxide, sodium carbonate, sodium phosphate, etc. Other metal salts include lithium, potassium, calcium, and magnesium. Additional pharmaceutically acceptable salts include ammonium cations formed with counterions such as halide, hydroxide, carboxylate, sulfate, phosphate, nitrate, loweralkyl sulfonate, and aryl sulfonate.

Abbreviations:

Abbreviations as used herein have the meanings known by one skilled in the art. Specifically, Ac represents acetyl group, Aoc represents allyloxycarbonyl group, Boc represents t-butoxycarbonyl group, Bn represents benzyl group, Bu represents butyl group, Bz represents benzoyl group, Cbz represents benzyloxycarbonyl group, CDI represents carbonyldiimidazole, DCM represents dichloromethane, DMAP represents 4-N,N-dimethylaminopyridine, DME represents 1,2-dimethoxyethane, DMF represents N,N-dimethylformamide, DMSO represents dimethyl sulfoxide, Et represents ethyl group, EtOAc represents ethyl acetate, Me represents methyl group, MEM represents 2-methoxyethoxymethyl group, MOM represents methoxylmethyl group, NMP represents N-methylpyrrolidinone, Ph represents phenyl group, Pr represents propyl group, TEA represents triethylamine, TFA represents trifluoroacetic acid, TFAA represents trifluoroacetic anhydride, THF represents tetrahydrofuran, TMS represents trimethylsilyl group, and Ts represents p-toluenesulfonyl group.

One embodiment of the current invention is a series of compounds (either quinone or hydroquinone form) having general formula I:

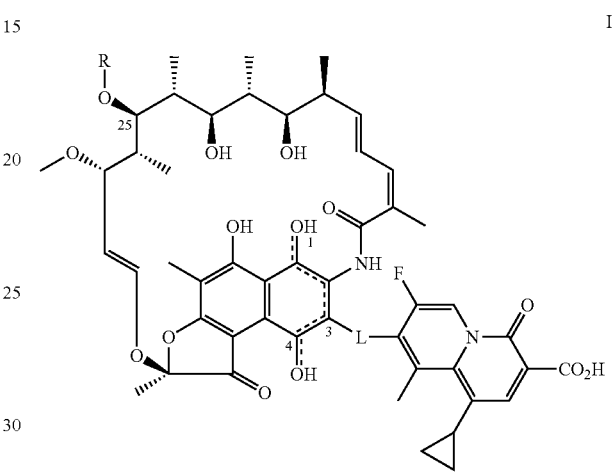

or its salts, hydrates or prodrugs thereof, wherein: a preferred R comprises hydrogen or acetyl; L is a linker, wherein a preferred linker group is selected from any combination of 1 to 5 structural elements shown in FIG. 1, provided L is not

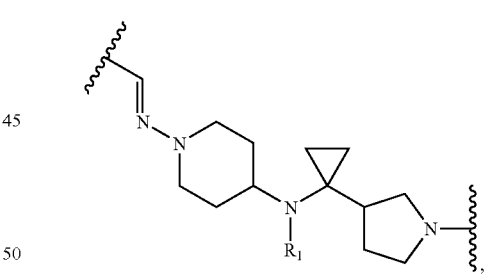

wherein $R_1$ is H, methyl or lower alkyls.

Compositions:

The compounds of the current invention are rifamycin derivatives of formula I. In one aspect, compounds of the current invention contain many asymmetric and geometric centers. In some cases, one or more of the asymmetric or geometric centers can be converted to their opposite configurations. These stereoisomers are within the scope of the present invention. The examples below are intended for illustration purposes only and are not intended to limit the scope of this invention.

Administration to a Subject:

The pharmaceutical composition of the present invention comprises a therapeutically effective amount of a compound of the current invention formulated together with one or more pharmaceutically acceptable carriers. Injectable preparations can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of a drug, it is often desirable to slow the absorption of the drug through subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and the following: 1) fillers or extenders such as starches, lactose, sucrose, glucose, mannitol, and silicic acid, 2) binders such as, carboxymethylcellulose, alginates, gelatin, polyvinylpyrrolidinone, sucrose, and acacia, 3) humectants such as glycerol, 4) disintegrating agents such as agar-agar, calcium carbonate, potato or tapioca starch, alginic acid, certain silicates, and sodium carbonate, 5) solution retarding agents such as paraffin, 6) absorption accelerators such as quaternary ammonium compounds, 7) wetting agents such as, cetyl alcohol and glycerol monostearate, 8) absorbents such as kaolin and bentonite clay, and 9) lubricants such as talc, calcium stearate, magnesium stearate, solid polyethylene glycols, sodium lauryl sulfate, and mixtures thereof. In the case of capsules, tablets and pills, the dosage form can also comprise buffering agents. Solid compositions of a similar type can also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient only, or preferentially, in a certain part of the intestinal tract, optionally, in a delayed manner. Examples of embedding compositions which can be used include polymeric substances and waxes. The active compounds can also be in microencapsulated form with one or more excipients as noted above.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as can be required. Ophthalmic formulation, ear drops, eye ointments, powders and solutions are also contemplated as being within the scope of this invention. The ointments, pastes, creams and gels can contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or animal by administering to the patient a therapeutically effective amount of a compound of the invention, in such amounts and for such time as is necessary to achieve the desired therapeutic effects. The term "therapeutically effective amount" of a compound of the invention is meant a sufficient amount of the compound to treat bacterial infections, at a reasonable benefit to risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or animals in single or in divided doses can be in amounts, for example, from 0.1 to 100 mg/kg body weight or preferably from 0.25 to 25 mg/kg body weight. Single dose compositions can contain such amounts or submultiples thereof to make up the daily dose. In general, treatment regimens according to the present invention comprise administration to an infected patient of such treatment from about 10 mg to about 2000 mg of the compounds of this invention per day in single or multiple doses. The compounds of current invention can be administrated orally, rectally, parenterally, intracisternally, intravaginally, intraperitoneally, topically, bucally, or as an oral or nasal spray.

Biological Activity:

Representative compounds were assayed for antimicrobial activity as follows: Minimum Inhibitory Concentrations (MICs) were determined by the microbroth dilution method as per NCCLS guidelines (National Committee for Clinical Laboratory Standards 2000), except that all growth incubations were conducted at 37° C. Bacterial cultures were tested in the following bacteriological media: S. aureus, S. epidermidis, and E. coli in Cation-Adjusted Mueller-Hinton Broth, S. pneumoniae in THY Broth supplemented with 1 mg/mL catalase under 5% $CO_2$ atmosphere, S. pyogenes in THY Broth, E. faecalis in BHI Broth, H. influenzae in BHI Broth supplemented with 0.75 µL of 1 mg/mL NAD and 150 µL of 1 mg/ml hematin per 5 mL, and M. smegmatis in Middlebrook Broth plus ADC Enrichment. The antimicrobial activity of the example compounds of the current invention are shown in Table 1.

TABLE 1

Antimicrobial activity (MIC range, mcg/ml) of the inventive compounds

| Organism | | Rifampin | Examples 4–62 |
|---|---|---|---|
| Staphylococcus aureus ATCC29213 | Rif-S | 0.008 | 0.008–2 |
| Staphylococcus aureus ATCC29213 RpoB$^{H481Y}$ | Rif-R | >64 | 0.06->64 |
| Staphylococcus aureus ATCC29213 RpoB$^{D471Y}$ | Rif-R | 8 | 0.06–32 |
| Staphylococcus aureus ATCC29213 GyrA$^{S84L}$ ParC$^{S80F}$ | FQ-R | 0.008 | 0.008–2 |
| Staphylococcus epidermidis ATCC 12228 | Rif-S | 0.03 | 0.004–2 |
| Streptococcus pneumoniae ATCC6303 | Rif-S | 0.061 | 0.002–0.25 |
| Streptococcus pyogenes ATCC19615 | Rif-S | 0.013 | 0.002–0.25 |
| Enterococcus faecalis ATCC29212 | Rif-S | 0.98 | 0.06->64 |
| Haemophilus influenzae ATCC10211 | Rif-S | 0.24 | 0.008->64 |
| Escherichia coli ATCC25922 | Rif-S | 16 | 0.03->64 |

Compounds of the current invention show potent activity against various organisms. Most importantly, compounds of the current invention demonstrate excellent activity against rifampin-resistant organisms. S. aureus ATCC 29213 RpoB$^{H481Y}$ is a rifampin-resistant strain with a mutation in RNA polymerase. This mutation results in a significant increase in the MIC for rifampin to about >64 µg/ml. Compounds of the current invention exhibit potent activity against this strain with a MIC as low as 0.06 µg/ml. S. aureus ATCC 29213 RpoB$^{D471Y}$ is another rifampin-resistant strain due to a RNA polymerase mutation with a MIC 8 µg/ml for rifampin. S. aureus ATCC 29213 GyrA$^{S84L}$ParC$^{S80F}$ is a quinolone-resistant strain with mutations to both DNA gyrase and topoisomerase IV. Compounds of the current invention show potent activity against this strain with MIC between 0.008 and 2 µg/ml. Compounds of the current invention are active against this rifampin-resistant strain with MICs as low as 0.06 µg/ml.

Synthetic Methods

The compounds of the current invention can be better understood in connection with the following synthetic schemes. The synthetic procedures in Schemes 1 to 8, shown in FIGS. 2-9, are for illustration purposes and are not intended to limit the scope of the invention. It will be apparent to one skilled in the art that the compounds of the current invention can be prepared by a variety of synthetic routes, including but not limited to substitution of appropriate reagents, solvents or catalysts, change of reaction sequence, and variation of protecting groups.

Figure 2:
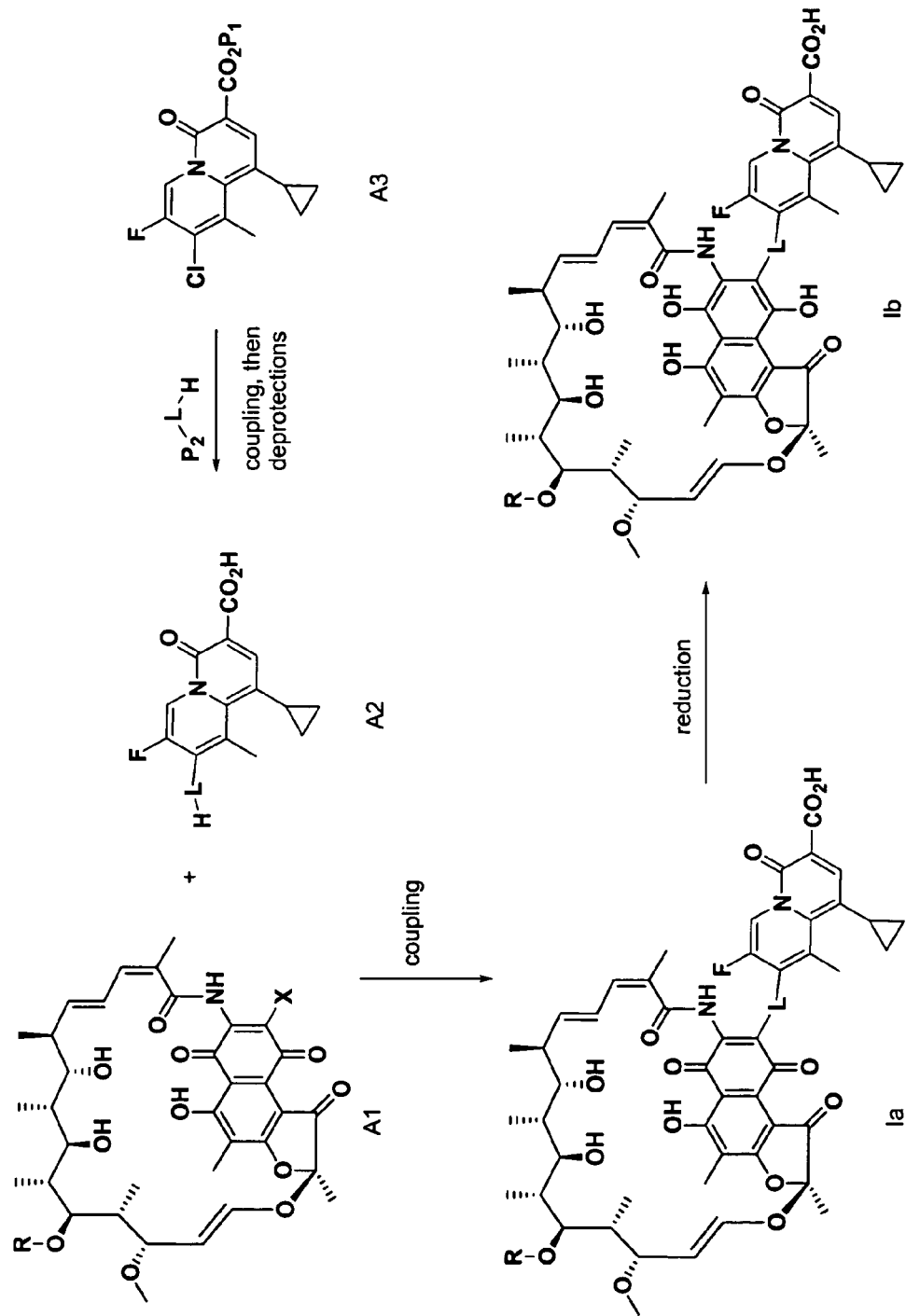
FIG. 2 shows Scheme A where compounds of general formula I are prepared.

Scheme A, shown in FIG. 2, shows a preparation of the compounds of formula I in accordance with this invention. In Scheme A, "L-H" denotes a pre-coupled linker that contains a nucleophilic group, like amino (>NH), hydroxyl (—OH) and thiol (—SH), $P_1$ is alkyl, $P_2$ is a protecting group, like BOC. Thus, rifamycin S (R=acetyl) or its 3-halorifamycin derivative (A1) prepared according to known methods (e.g.:) couples with a 4-oxoquinolizinecarboxylic acid derivative (A2) prepared by following known methods from A3 and compound "$P_2$-L-H" (e.g.: Li, Q.; Chu, D. T. W.; et al. J. Med. Chem., 1996, 39, 3070-3088) in aqueous alcoholic solvent, like ethanol, in the presence of a base, like sodium bicarbonate to give a compound (Ia) of this invention. The protected linker compound "$P_2$-L-H" is prepared individually, which is shown in individual examples of this invention. Compound Ia can be reduced using a reductant, like ascorbic acid, in alcoholic solvent, like methanol to give compound Ib. Compound Ia is the quinone form of compound Ib, both forms are constituents of formula I of this invention.

Figure 3:
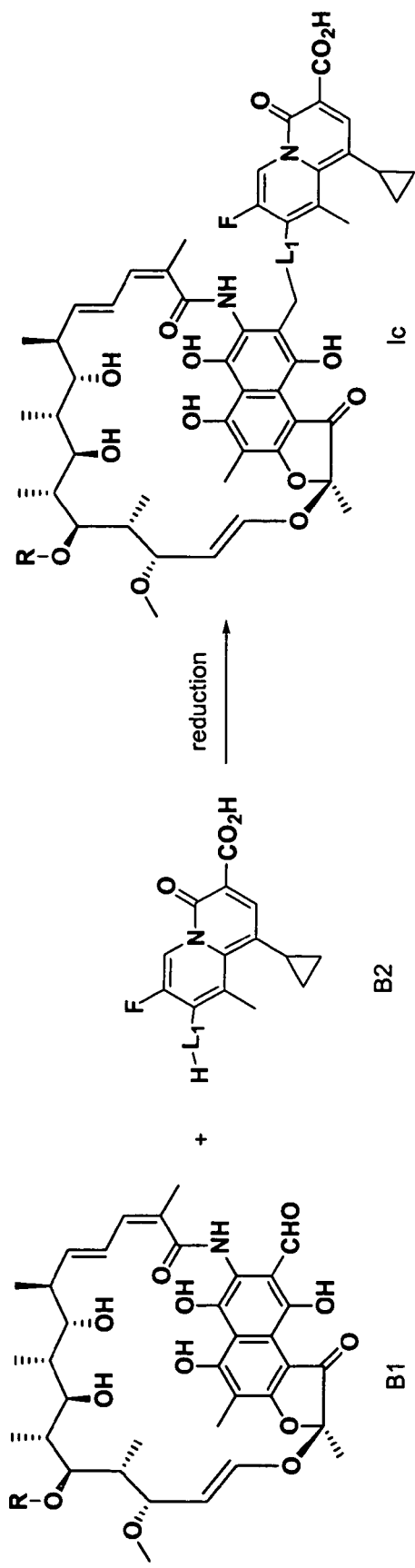
FIG. 3 shows Scheme B where another set of compounds of general formula I are prepared.

Scheme B, shown in FIG. 3, illustrates a preparation of other sets of the compounds of formula I of this invention. The preparation takes advantage of 3-formylrifamycin or its derivative B1, which reacts with a 4-oxoquinolizinecarboxylic acid derivative B2 prepared as described above, in the presence of a reducing agent, like sodium cyanoborohydride, in solvent, like methanol, acetic acid or a mixture provides compound Ic of the formula I of this invention. In scheme B, "$L_1$-H" represents amino groups, like —$NH_2$, >NH, and "$L_1$" is the part of linker group "L".

Figure 4:
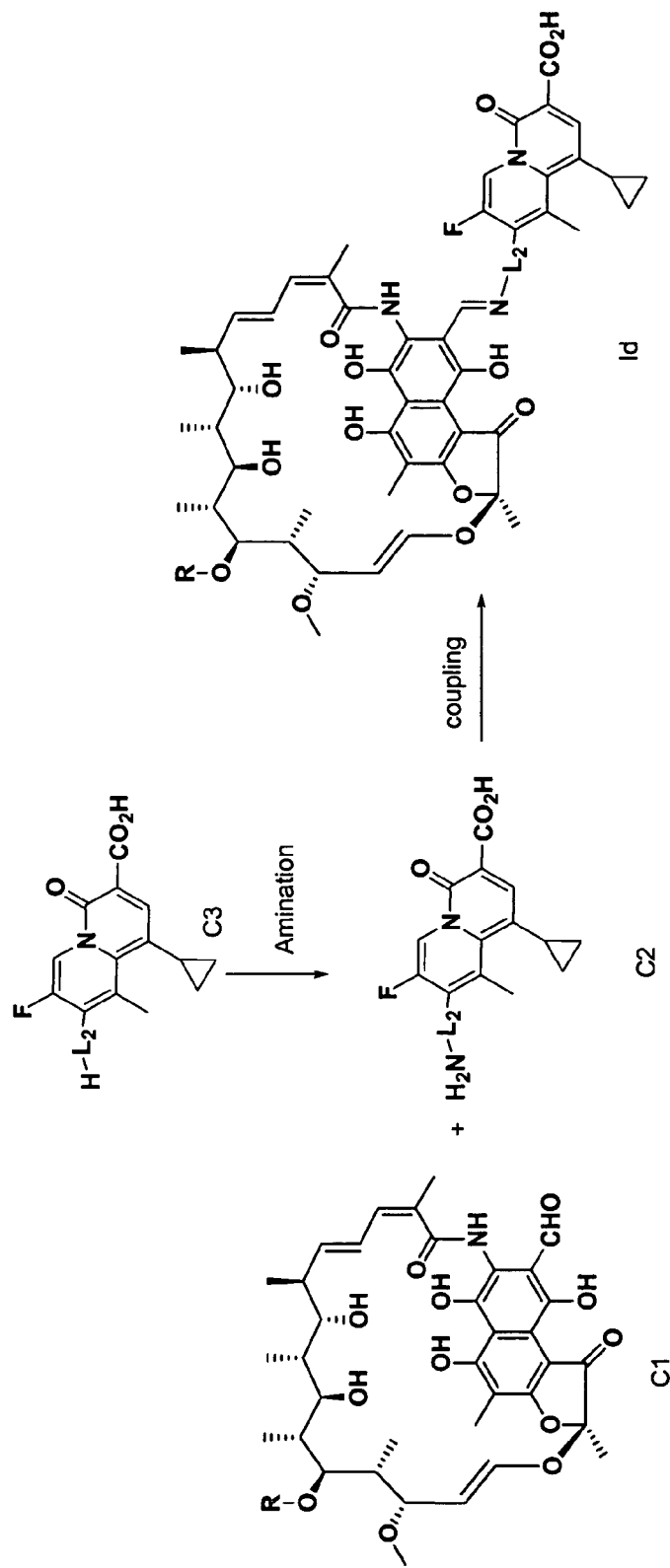
FIG. 4 shows Scheme C where yet another set of compounds of general formula I are prepared.

Scheme C, shown in FIG. 4, illustrates a preparation of yet other sets of the compounds of formula I of this invention. The preparation also takes advantage of 3-formylrifamycin or its derivative C1, which couples with a hydrazino-4-oxoquinolizinecarboxylic acid derivative C2 prepared from 4-oxoquinolizinecarboxylic acid derivative C3, which in turn prepared as described above. Transformation of C3 to C2 can be done by a single step reaction using an aminating agent, like HN2-OSO3H in aqueous NaOH, or a two-step reaction, involving nitrosylation, using sodium nitrite in aqueous acid, like HCl, followed by reduction with a reagent, like zinc in acetic acid. The coupling of 3-formylrifamycin C1 and hydrazine C2 can be done in solvent, like methanol, THF, water, acetic acid or a mixture of them provides compound Id of the formula I of this invention. In scheme C, "L$_2$-H" represents amino groups, like —NH$_2$, >NH, and "L$_2$" is the part of linker group "L".

Specific Compositions

The compounds of the current invention may be better understood with reference to the following specific examples, which are representative of some of the embodiments of the invention, and are not intended to limit the invention.

All starting materials used in these examples are either purchased from commercial sources or prepared according to published procedures. Operations involving moisture and/or oxygen sensitive materials are conducted under an atmosphere of nitrogen. Flash chromatography is performed using silica gel 60 as normal phase adsorbent or C18 silica gel as reverse phase adsorbent. Thin layer chromatography ("TLC") and preparative thin layer chromatography ("PTLC") are performed using pre-coated plates purchased from E. Merck and spots are visualized with ultraviolet light followed by an appropriate staining reagent. Nuclear magnetic resonance ("NMR") spectra are recorded on a Varian 400 MHz magnetic resonance spectrometer. $^1$H NMR chemical shift are given in parts-per million (δ) downfield from TMS using the residual solvent signal (CHCl$_3$=δ7.26, CH$_3$OH=δ3.31) as internal standard. $^1$H NMR information is tabulated in the following format: number of protons, multiplicity (s, singlet; d, doublet; t, triplet; q, quartet; m, multiplet; dd, doublet of doublet; td, triplet of doublet; dt, doublet of triplet), coupling constant(s) (J) in hertz. The prefix app is occasionally applied in cases where the true signal multiplicity is unresolved and prefix br indicates a broad signal. Electro spray ionization mass spectra are recorded on a Finnegan LCQ advantage spectrometer.

EXAMPLE 1

(R/S)-3-{[1-(3-Carboxy-1-cyclopropyl-7-fluoro-9-methyl-4-oxo-4H-quinolizine-8-yl)-pyrrolidin-3-ylmethyl]-amino}-rifamycin S

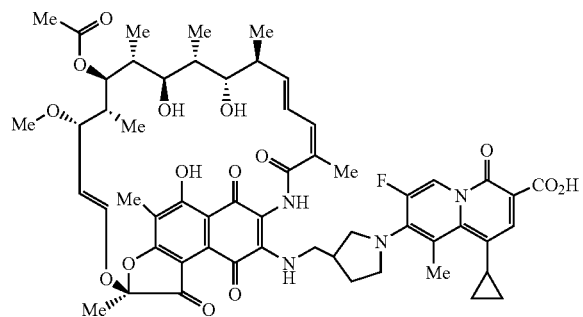

Synthesis: Step 1. (R/S)-8-[3-(tert-Butoxycarbonylamino-methyl)-pyrrolidin-1-yl]-1-cyclopropyl-7-fluoro-9-methyl-4-oxo-4H-quinolizine-3-carboxylic acid ethyl ester

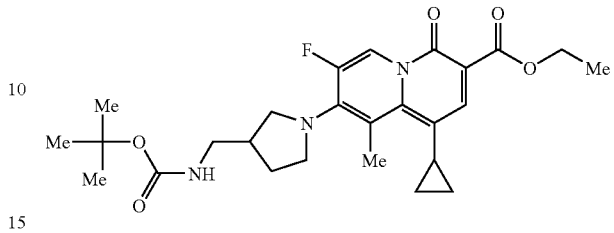

To a stirred solution of 3-aminomethyl-pyrrolidine-1-carboxylic acid tert-butyl ester (210 mg, 1.05 mmol) in dichloromethane (5.0 mL) was added trifluoroacetic acid (0.80 mL, 10.4 mmol). After stirring at room temperature for 30 minutes, the solution was removed solvent and trifluoroacetic acid. The solution of the residue in acetonitrile (4.0 mL) was added 8-chloro-1-cyclopropyl-7-fluoro-9-methyl-4-oxo-4H-quinolizine-3-carboxylic acid ethyl ester (This compound was prepared by following the procedure described in *Heterocycles*, 1999, Vol 51(6), 1345-1353; 210 mg, 0.65 mmol) and NaHCO$_3$ (1.2 g, 14.3 mmol). The suspension was heated to reflux for three hours. The resulting mixture was filtered and condensed. The residue was dissolved in DMF and added di-tert-butyl dicarbonate (300 mg, 1.37 mmol) and triethylamine (0.20 mL, 1.43 mmol). The resulting solution was partitioned between ethyl acetate and water. The separated organic layer was washed with brine, dried over sodium sulfate and concentrated in vacuo. The residue was purified by preparative thin layer chromatography (10% methanol in dichloromethane) to give the title compound as a yellow solid (153 mg, 48%). ESI MS m/z 488.3 (M+H$^+$).

Step 2. (R/S)-8-[3-(tert-Butoxycarbonylamino-methyl)-pyrrolidin-1-yl]-1-cyclopropyl-7-fluoro-9-methyl-4-oxo-4H-quinolizine-3-carboxylic acid:

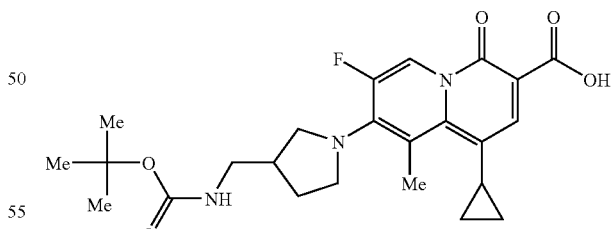

To a solution of product from step 1 (153 mg, 0.31 mmol) in ethanol (5.0 mL) was added the solution of LiOH.H$_2$O (150 mg, 3.5 mmol) in water (2.0 mL). The solution was heated at 60° C. for two hours. The resulting solution was partitioned between dichloromethane and saturated aq NH$_4$Cl. The separated organic layer was washed with brine, dried over sodium sulfate and concentrated in vacuo to yield the title compound as a yellow solid (124 mg, 87%). ESI MS m/z 460.1 (M+Na$^+$).

Step 3. (R/S)-8-(3-Aminomethyl-pyrrolidin-1-yl)-1-cyclopropyl-7-fluoro-9-methyl-4-oxo-4H-quinolizine-3-carboxylic acid (trifluoroacetate salt):

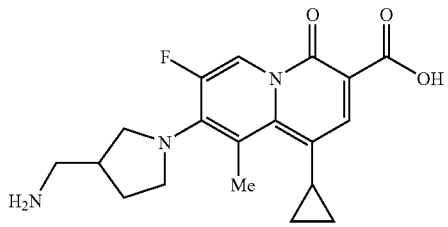

To a stirred solution of product from step 2 (124 mg, 0.27 mmol) in dichloromethane (1.0 mL) was added trifluoroacetic acid (0.25 mL, 3.2 mmol). After stirring at room temperature for one hour, the solvent and trifluoroacetic acid were removed to yield a yellow solid (127 mg, 100%). ESI MS m/z 360.0 (M+H$^+$).

Step 4. (R/S)-3-{[1-(3-Carboxy-1-cyclopropyl-7-fluoro-9-methyl-4-oxo-4H-quinolizine-8-yl)-pyrrolidin-3-ylmethyl]-amino}-rifamycin S: The solution of the product from step 3 (12 mg, 0.025 mmol) and 3-bromorifamycin S (this compound was prepared by following the procedure described in DE 2548128; 28 mg, 0.036 mmol) in ethanol (0.6 mL) was added triethylamine (30 µL, 0.21 mmol). The solution was stirred at room temperature overnight and then partitioned between dichloromethane and water. The separated organic layer was washed with brine, dried over sodium sulfate, concentrated in vacuo. The residue was purified by preparative thin layer chromatography (10% methanol in dichloromethane) to give the title compound as a dark brown solid (15 mg, 57%). ESI MS m/z 1053.3 (M+H$^+$). $^1$H NMR (400 MHz, CDCl$_3$) δ 13.87 (s, 1H), 13.55 (s, 1H), 9.06 (d, J=10.4 Hz, 1H), 8.24 (s, 1H), 7.77 (s, 1H), 6.90-6.82 (m, 1H), 6.78-6.72 (m, 1H), 6.35 (d, J=10.0 Hz, 1H), 6.19 (dd, J=6.0, 15.2 Hz, 1H), 6.09 (d, J=12.4 Hz, 1H), 5.13 (dd, J=5.6, 12.4 Hz, 1H), 5.01 (d, J=10.0 Hz, 1H), 3.92 (d, J=8.8 Hz, 1H), 3.87-3.72 (m, 4H), 3.70-3.52 (m, 5H), 3.47 (br s, 1H), 3.10 (s, 3H), 3.06-3.02 (m, 1H), 2.68-2.60 (m, 1H), 2.62 (s, 3H), 2.40-2.32 (m, 1H), 2.30 (s, 3H), 2.30-2.22 (m, 1H), 2.20-2.12 (m, 1H), 2.10 (s, 3H), 2.07 (s, 3H), 1.90-1.65 (m, 3H), 1.75 (s, 3H), 1.26-1.14 (m, 1H), 1.05 (d, J=6.8 Hz, 3H), 1.05-0.94 (m, 2H), 0.86-0.81 (m, 3H), 0.70-0.64 (m, 5H), 0.09 (d, J=6.8 Hz, 3H).

EXAMPLE 2

(R/S)-3-{[1-(3-Carboxy-1-cyclopropyl-7-fluoro-9-methyl-4-oxo-4H-quinolizine-8-yl)-pyrrolidin-3-yl]-amino}-rifamycin S

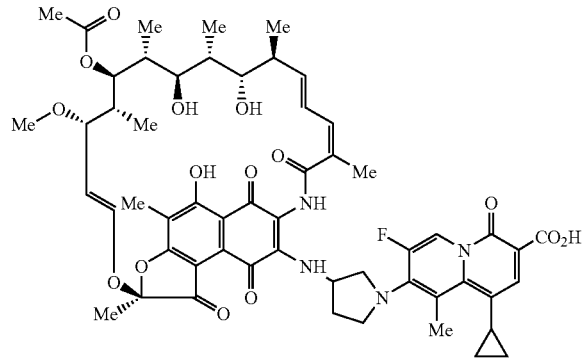

Synthesis: The title compound was prepared by using the same procedure as described in Step 1-4 of Example 1 except (R/S)-3-aminopyrrolidine-1-carboxylic acid tert-butyl ester was used in place of (R/S)-3-aminomethyl-pyrrolidine-1-carboxylic acid tert-butyl ester. ESI MS m/z 1039.0 (M+H$^+$). $^1$H NMR (400 MHz, CDCl$_3$) δ (~1:1 mixture of two diastereomers) 13.40, 13.39 (two singlets, 1H), 11.50 (br s, 1H), 9.15, 9.11 (two doublets, d, J=10.4 Hz, 1H), 8.33, 8.31 (two singlets, 1H), 7.88, 7.83 (two singlets, 1H), 7.02-6.96 (m, 1H), 6.80-6.76 (m, 1H), 6.35 (app d, J=9.6 Hz, 1H), 6.23-6.18 (m, 1H), 6.10 (d, J=12.0 Hz, 1H), 5.16-5.12 (m, 1H), 5.02-4.98 (m, 1H), 4.69 (app s, 1H), 4.22-4.18 (m, 1H), 4.04-3.47 (m, ~6H), 3.18-3.08 (m, 4H), 3.11 (s, 3H), 2.69, 2.66 (two doublets, 3H), 2.41-2.36 (m, 1H), 2.31-2.30 (two singlets, 3H), 2.24-2.18 (m, 1H), 2.09 (s, 3H), 2.07 (s, 3H), 1.82-1.70 (overlap with Me, m, 2H), 1.75 (s, 3H), 1.24-1.18 (m, 1H), 1.06, 1.05 (two doublets, J=6.0 Hz, 3H), 0.88 (d, J=6.8 Hz, 2H), 0.81 (d, J=6.8 Hz, 2H), 0.71 (d, J=6.4 Hz, 3H), 0.68 (d, J=7.2 Hz, 3H), 0.13, 0.09 (two doublets, J=6.4 Hz, 3H).

EXAMPLE 3

(R/S)-3-{[1-(3-Carboxy-1-cyclopropyl-7-fluoro-9-methyl-4-oxo-4H-quinolizine-8-yl)-pyrrolidin-3-yl]-methyl-amino}-rifamycin S

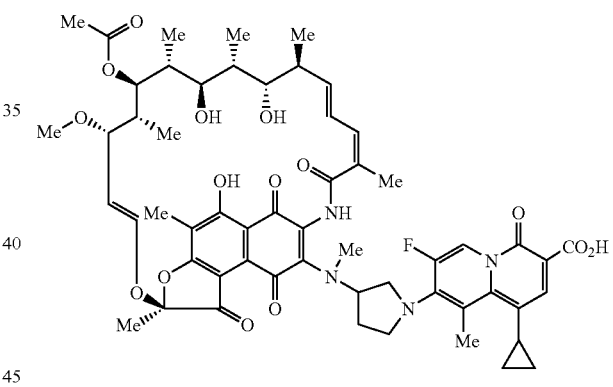

Synthesis: The title compound was prepared by using the same procedure as described in Step 1-4 of Example 1 except (R/S)-3-methylamino-pyrrolidine-1-carboxylic acid tert-butyl ester was used in place of (R/S)-3-aminomethyl-pyrrolidine-1-carboxylic acid tert-butyl ester. ESI MS m/z 1053.2 (M+H$^+$). $^1$H NMR (400 MHz, CDCl$_3$) δ 13.82 (~1:1 mixture of two diastereomers) (br s, 1H), 13.13, 13.07 (two singlets, 1H), 9.17, 9.08 (two doublets, J=10.4 Hz, 1H), 8.31 (s, 1H), 7.74, 7.72 (two singlets, 1H), 7.30-7.22 (m, 1H), 6.45-6.40 (m, 1H), 6.26-6.18 (m, 1H), 6.10 (d, J=12.8 Hz, 1H), 5.14-5.08 (m, 2H), 4.62-4.56 (m, 1H), 4.08-3.38 (m, ~9H), 3.12, 3.11 (two singlets, 3H), 3.09-3.02 (m, 1H), 2.77, 2.75 (two singlets, 3H), 2.71, 2.68 (two singlets, 3H), 2.41-2.36 (m, 2H), 2.29 (s, 3H), 2.24-2.18 (m, 1H), 2.16, 2.15 (two singlets, 3H), 2.10, 2.08 (two singlets, 3H), 1.82-1.70 (overlap with Me, m, 2H), 1.77, 1.75 (two singlets, 3H), 1.24-1.18 (m, 1H), 1.06, 1.04 (two doublets, J=7.6 Hz, 3H), 1.00-0.92 (m, 2H), 0.89-0.87 (two doublets, J=6.8 Hz, 3H), 0.81-0.68 (m, 2H), 0.72, 0.63 (two doublets, J=6.8 Hz, 3H), 0.22, 0.20 (two doublets, J=6.4 Hz, 3H).

EXAMPLE 4

(R/S)-3-{4-[1-(3-Carboxy-1-cyclopropyl-7-fluoro-9-methyl-4-oxo-4H-quinolizine-8-yl)-pyrrolidin-3-ylmethyl]-piperazin-1-yl}-rifamycin S

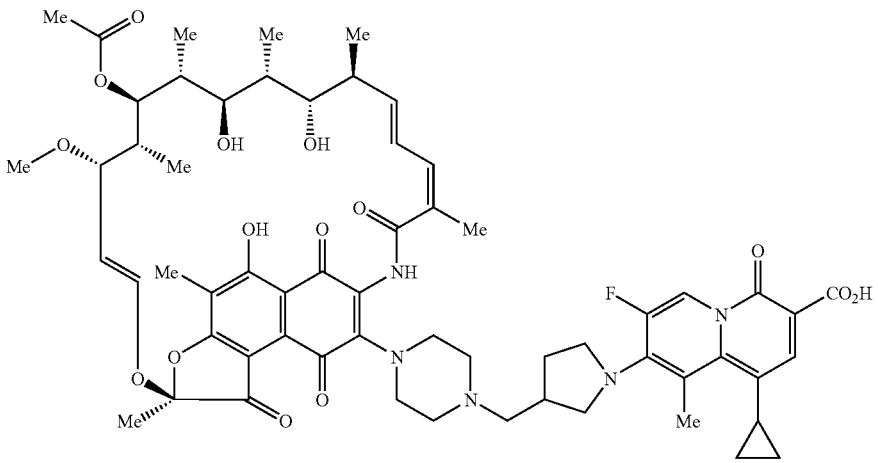

Synthesis: Step 1. 4-Acryloyl-piperazine-1-carboxylic acid tert-butyl ester

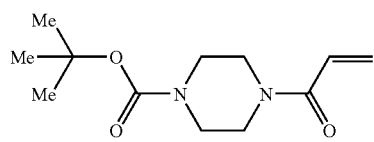

To a solution of piperazine-1-carboxylic acid tert-butyl ester (3.9 g, 21 mmol) in dichloromethane at 0° C. was added diisopropylethylamine (3.7 mL, 21 mmol), followed by a solution of acryloyl chloride (1.8 mL, 22 mmol) in dichloromethane (15 mL). The mixture was allowed to stir at 0° C. to room temperature for 18 hours. The mixture was washed with 5% aq HCl, follows by saturated aq NaHCO₃ solution, dried and concentrated to give a clear oil (4.5 g, 90%), which was used in next step without purification.

Step 2. (R/S)-4-(1-Benzyl-pyrrolidine-3-carbonyl)-piperazine-1-carboxylic acid tert-butyl ester

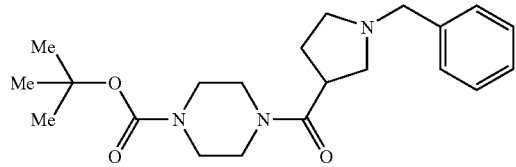

To the solution of the product from step 1 (~20 mmol) in toluene (50 mL) was added N-(methoxymethyl)-N-(trimethylsilylmethyl)benzylamine (5.1 mL, 20 mmol) followed by of trifluoroacetic acid (0.1 mL, 0.9 mmol) at room temperature. The mixture was allowed to stir at room temperature for 18 hours. The mixture was washed with saturated aq NaHCO₃ solution, dried over Na₂SO₄ and concentrated. The residue was purified by chromatography on silica gel (10% MeOH in ethyl acetate) to give a solid (4.0 g, 60%).

Step 3. (R/S)-4-(1-Benzyl-pyrrolidin-3-ylmethyl)-piperazine-1-carboxylic acid tert-butyl ester

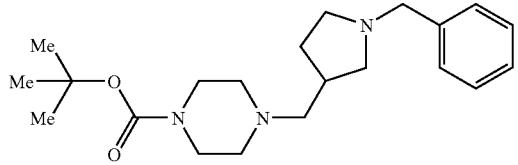

To a stirred solution of the product from step 2 (500 mg, 1.3 mmol) in THF (20 mL) was added a solution of BH₃.THF (1N solution in THF, 3.0 mL, 3.0 mmol) at room temperature. The mixture was allowed to stir at room temperature for two hours, and then heated at reflux for 18 hours. The solvent was removed, and the residue was digested in 20% aq NaOH. The mixture was extracted with dichloromethane. The combined extracts were dried and concentrated to give an oil (400 mg, 78%).

Step 4. (R/S)-4-Pyrrolidin-3-ylmethyl-piperazine-1-carboxylic acid tert-butyl ester

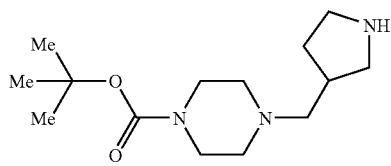

To a stirred solution of the product from step 3 (400 mg, 1.1 mmol) in acetic acid (10 mL), 20% Pd(OH)₂/C (100 mg) was added and the mixture was hydrogenated at 1 atm using a hydrogen balloon for 18 hours. The catalyst was filtered, and the solvent was removed, and the residue was partitioned between 20% aq NaOH (small amount) and dichloromethane. The aqueous layer was extracted with dichloromethane twice, and the combined organic extracts were dried and concentrated to give an oil (200 mg, 65%).

Step 5. (R/S)-8-[3-(4-tert-Butoxycarbonyl-piperazin-1-ylmethyl)-pyrrolidin-1-yl]-1-cyclopropyl-7-fluoro-9-methyl-4-oxo-4H-quinolizine-3-carboxylic acid ethyl ester:

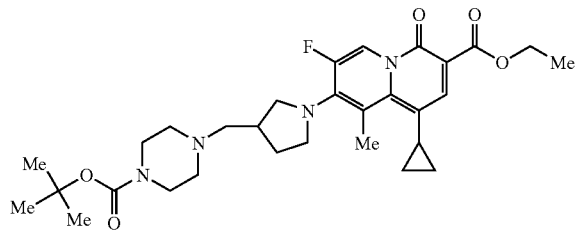

To a solution of 8-chloro-1-cyclopropyl-7-fluoro-9-methyl-4-oxo-4H-quinolizine-3-carboxylic acid ethyl ester (120 mg, 0.37 mmol) and the product from step 4 (94 mg, 0.35 mmol) in acetonitrile (3.0 mL) was added NaHCO$_3$ (270 mg, 3.21 mmol). The suspension was heated to reflux for five hours. The resulting mixture was partitioned between ethyl acetate and water. The separated organic layer was washed with brine, dried over sodium sulfate and concentrated in vacuo. The residue was purified by preparative thin layer chromatography (10% methanol in dichloromethane) to give the title compound as a yellow solid (124 mg, 64%). ESI MS m/z 557.2 (M+H$^+$).

Step 6. (R/S)-8-[3-(4-tert-Butoxycarbonyl-piperazin-1-ylmethyl)-pyrrolidin-1-yl]-1-cyclopropyl-7-fluoro-9-methyl-4-oxo-4H-quinolizine-3-carboxylic acid:

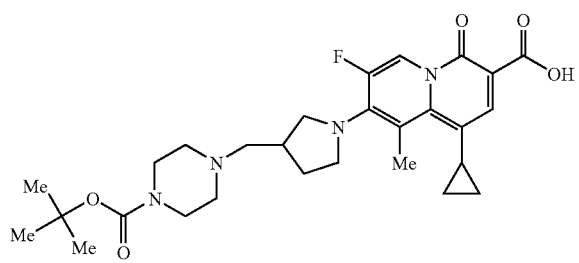

To a solution of product from step 5 (124 mg, 0.22 mmol) in ethanol (4.0 mL) was added the solution of LiOH.H$_2$O (108 mg, 2.6 mmol) in water (2.0 mL). The solution was heated at 60° C. for two hours. The resulting solution was partitioned between dichloromethane and saturated aq NH$_4$Cl. The separated organic layer was washed with brine, dried over sodium sulfate, concentrated in vacuo to give the title compound as a yellow solid (110 mg, 95%). ESI MS m/z 529.3 (M+Na$^+$).

Step 7. (R/S)-1-Cyclopropyl-7-fluoro-9-methyl-4-oxo-8-(3-piperazin-1-ylmethyl-pyrrolidin-1-yl)-4H-quinolizine-3-carboxylic acid (trifluoroacetate salt):

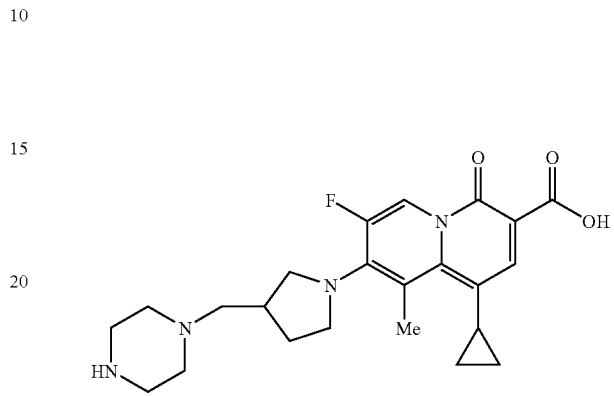

To a stirred solution of product from step 6 (110 mg, 0.21 mmol) in dichloromethane (1.0 mL) was added trifluoroacetic acid (0.25 mL, 3.2 mmol). After stirring at room temperature for one hour, the solution was removed solvent and trifluoroacetic acid to give the title compound as a yellow solid (114 mg, 100%). ESI MS m/z 429.3 (M+H$^+$).

Step 8. (R/S)-3-{4-[1-(3-Carboxy-1-cyclopropyl-7-fluoro-9-methyl-4-oxo-4H-quinolizine-8-yl)-pyrrolidin-3-ylmethyl]-piperazin-1-yl}-rifamycin S: The solution of the product from step 7 (18 mg, 0.033 mmol) and 3-bromorifamycin S (30 mg, 0.039 mmol) in ethanol (1.0 mL) was added triethylamine (30 μL, 0.21 mmol). The solution was stirred at room temperature for one hour and partitioned between dichloromethane and water. The separated organic layer was washed with brine, dried over sodium sulfate and concentrated in vacuo. The residue was purified by preparative thin layer chromatography (10% methanol in dichloromethane) to give the title compound as a dark brown solid (23 mg, 62%). ESI MS m/z 1122.5 (M+H$^+$). $^1$H NMR (400 MHz, CDCl$_3$) δ (~1:1 mixture of two diastereomers) 13.90 (br s, 1H), 13.28 (br s, 1H), 9.10 (d, J=10.4 Hz, 1H), 8.23 (s, 1H), 7.54 (s, 1H), 7.10-7.04 (m, 1H), 6.36 (d, J=10.8 Hz, 1H), 6.17 (dd, J=6.0, 15.2 Hz, 1H), 6.07 (d, J=12.4 Hz, 1H), 5.12-5.08 (m, 2H), 4.00-3.85 (m, 3H), 3.77-3.36 (m, ~12H), 3.11 (s, 3H), 3.06 (d, J=10.0 Hz, 1H), 2.78-2.45 (m, 6H), 2.63 (s, 3H), 2.40-2.32 (m, 1H), 2.27 (s, 3H), 2.20-2.14 (m, 1H), 2.13, 2.12 (two singlets, 3H), 2.09 (s, 3H), 1.86-1.70 (m, 1H), 1.75 (s, 3H), 1.72-1.68 (m, 1H), 1.26-1.18 (m, 1H), 1.04 (d, J=6.8 Hz, 3H), 1.02-0.95 (m, 2H), 0.89(d, J=7.2 Hz, 3H), 0.72-0.68 (m, 5H), 0.19 (d, J=6.8 Hz, 3H).

EXAMPLE 5

(S)-3-{4-[1-(3-Carboxy-1-cyclopropyl-7-fluoro-9-methyl-4-oxo-4H-quinolizine-8-yl)-pyrrolidin-3-yl-oxycarbonyl]-piperazin-1-yl}-rifamycin S

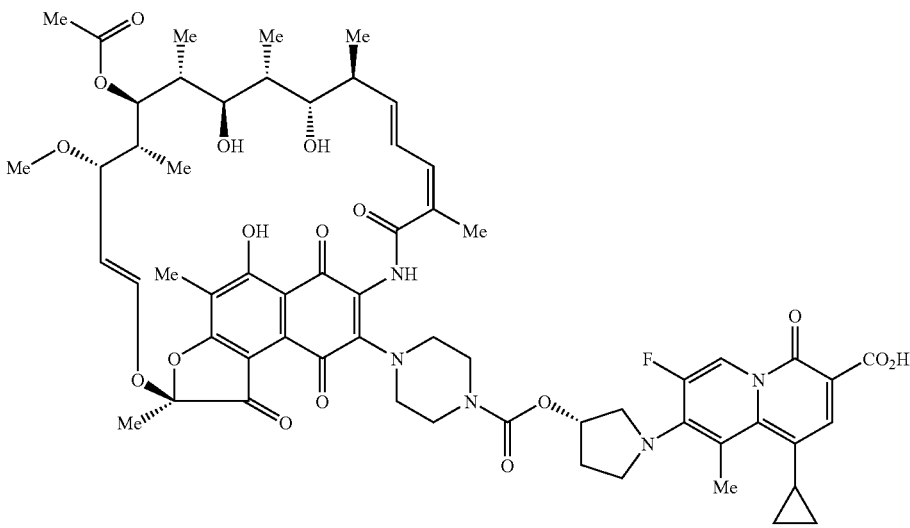

Synthesis: Step 1. (S)-1-Cyclopropyl-7-fluoro-8-(3-hydroxy-pyrrolidin-1-yl)-9-methyl-4-oxo-4H-quinolizine-3-carboxylic acid ethyl ester:

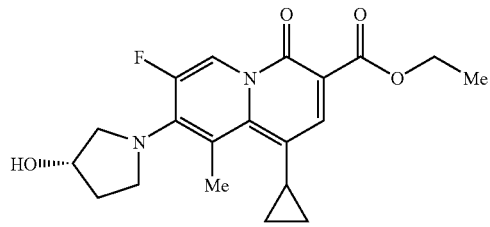

The title compound was prepared by using the same procedure as described in step 5 in example 4 except (S)-3-hydroxy pyrrolidine was used in place of 4-pyrrolidin-3-ylmethyl-piperazine-1-carboxylic acid tert-butyl ester. ESI MS m/z 375.1 (M+H$^+$).

Step 2. 1-Cyclopropyl-7-fluoro-9-methyl-4-oxo-8-[3-(piperazine-1-carbonyloxy)-pyrrolidin-1-yl]-4H-quinolizine-3-carboxylic acid ethyl ester:

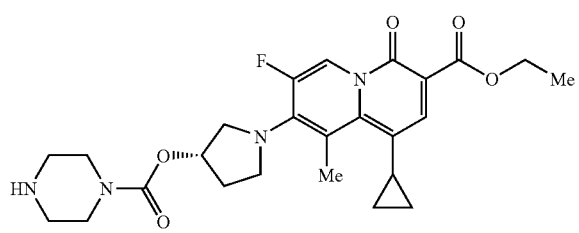

To the solution of product from step 1 (156 mg, 0.42 mmol) and 1,1'-carbonyldiimidazole (95 mg, 0.58 mmol) in dichloromethane (5.0 mL) and THF (3.0 mL) was added K$_2$CO$_3$ (210 mg, 1.52 mmol). The resulting mixture was heated at 40° C. overnight and then partitioned between ethyl acetate and water. The separated organic layer was washed with brine, dried over sodium sulfate and concentrated in vacuo. The resulting yellow oil was dissolved in THF (6.0 mL) and added piperazine (400 mg, 4.64 mmol). The solution was brought to 50° C. for one hour and then partitioned between ethyl acetate and water. The separated organic layer was washed with brine, dried over sodium sulfate and concentrated in vacuo. The residue was purified by preparative thin layer chromatography (10% methanol in dichloromethane) to give the title compound as a yellow solid (100 mg, 50%). ESI MS m/z 487.1 (M+H$^+$).

Step 3. 1-Cyclopropyl-7-fluoro-9-methyl-4-oxo-8-[3-(piperazine-1-carbonyloxy)-pyrrolidin-1-yl]-4H-quinolizine-3-carboxylic acid (trifluoroacetate salt)

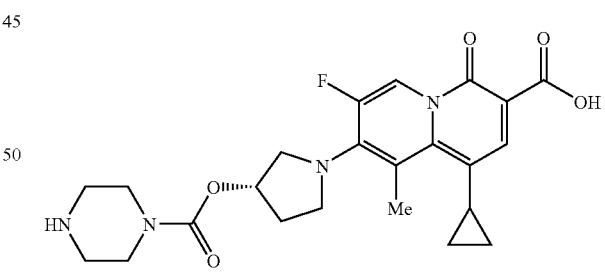

To a solution of product from step 2 (45 mg, 0.09 mmol) in ethanol (1.6 mL) was added the solution of LiOH.H$_2$O (52 mg, 1.2 mmol) in water (0.8 mL). The solution was heated at 60° C. for one hour and cooled to room temperature. Trifluoroacetic acid (0.15 mL, 1.3 mmol) was added and the resulting solution was partitioned between dichloromethane and water. The aqueous phase was extracted with 20% isopropanol in dichloromethane. The combined organic layer was washed with brine, dried over sodium sulfate and concentrated in vacuo to give the title compound as a yellow foam (53 mg, 100%), ESI MS m/z 459.1 (M+H$^+$).

Step 4. (S)-3-{4-[1-(3-Carboxy-1-cyclopropyl-7-fluoro-9-methyl-4-oxo-4H-quinolizine-8-yl)-pyrrolidin-3-yl-oxycarbonyl]-piperazin-1-yl}-rifamycin S: The title compound was prepared by using the same procedure as described in step 8 of example 4 except 1-cyclopropyl-7-fluoro-9-methyl-4-oxo-8-[3-(piperazine-1-carbonyloxy)-pyrrolidin-1-yl]-4H-quinolizine-3-carboxylic acid (trifluoroacetate salt) was used in place of 1-cyclopropyl-7-fluoro-9-methyl-4-oxo-8-(3-piperazin-1-ylmethyl-pyrrolidin-1-yl)-4H-quinolizine-3-carboxylic acid (trifluoroacetate salt). ESI MS m/z 1174.4 (M+Na$^+$). $^1$H NMR (400 MHz, CDCl$_3$) δ 13.87 (s, 1H), 13.11 (s, 1H), 9.15 (d, J=10.0 Hz, 1H), 8.30 (s, 1H), 7.60 (s, 1H), 7.03 (dd, J=11.2, 15.6 Hz, 1H), 6.38 (d, J=10.8 Hz, 1H), 6.19 (dd, J=6.4, 16.0 Hz, 1H), 6.06 (dd, J=1.6, 12.4 Hz, 1H), 5.43 (app s, 1H), 5.11 (d, J=9.6 Hz, 1H), 5.08 (dd, J=4.8, 12.4 Hz, 1H), 4.19-4.02 (m, 3H), 3.91 (d, J=9.6 Hz, 1H), 3.90-3.82 (m, 1H), 3.73-3.26 (m, ~12H), 3.11 (s, 3H), 3.05 (d, J=10.4 Hz, 1H), 2.66 (s, 3H), 2.38-2.27 (m, 2H), 2.27 (s, 3H), 2.23-2.18 (m, 1H), 2.12 (s, 3H), 2.10 (s, 3H), 1.82-1.76 (overlap with Me, m, 1H), 1.75 (s, 3H), 1.69-1.63 (m, 1H), 1.25-1.19 (m, 1H), 1.12-1.07 (m, 1H), 1.03 (d, J=6.8 Hz, 3H), 0.97-0.91 (m, 1H), 0.83 (d, J=7.2 Hz, 3H), 0.73-0.66 (m, 5H), 0.15 (d, J=7.2 Hz, 3H).

EXAMPLE 6

(R/S)-3-4-{[1-(3-Carboxy-1-cyclopropyl-7-fluoro-9-methyl-4-oxo-4H-quinolizine-8-yl)-pyrrolidin-3-yl-carbonyl]-amino}-piperidin-1-yl)-rifamycin S

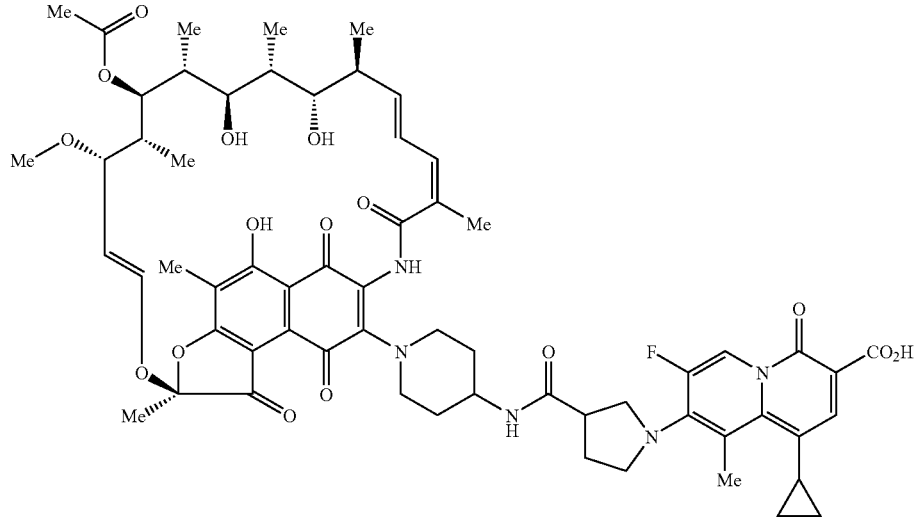

Synthesis: Step 1. (R/S)-4-[(1-Benzyloxycarbonyl-pyrrolidine-3-carbonyl)-amino]-piperidine-1-carboxylic acid tert-butyl ester:

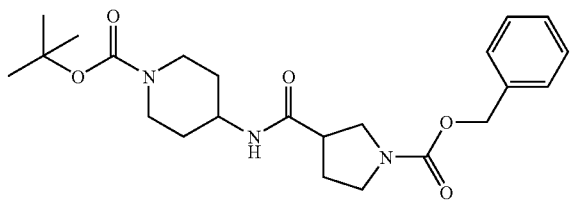

To the solution of 4-amino-piperidine-1-carboxylic acid tert-butyl ester (0.82 g, 4.1 mmol) and pyrrolidine-1,3-dicarboxylic acid 1-benzyl ester (0.99 mL, 4.0 mmol) in dichloromethane (10.0 mL) was added 1-(3-dimethylaminopropyl)-3-ethylcarbodiimide hydrochloride (1.06 g, 5.5 mmol) and 4-dimethylaminopyridine (0.10 g, 0.8 mmol). After stirred at room temperature overnight, the solution was partitioned between ethyl acetate and water. The separated organic layer was washed with water, brine, dried over sodium sulfate, concentrated in vacuo to give a white solid (1.62 g, 95%).

Step 2. (R/S)-4-[(Pyrrolidine-3-carbonyl)-amino]-piperidine-1-carboxylic acid tert-butyl ester:

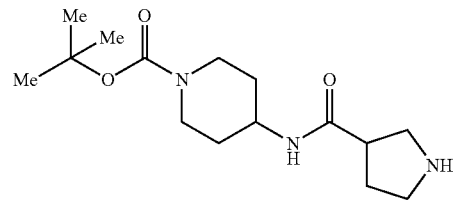

To the solution of product from step 1 (130 mg, 0.30 mmol) in methanol (4.0 mL) was added 30% Pd/C (20 mg). The resulting mixture was hydrogenated at 1 atm for 40 minutes. Filtered off the catalyst and removed solvent to give a pale yellow oil (~100 mg) which could be used in next step directly.

Step 3-6. (R/S)-3-(4-{[1-(3-Carboxy-1-cyclopropyl-7-fluoro-9-methyl-4-oxo-4H-quinolizine-8-yl)-pyrrolidin-3-yl-carbonyl]-amino}-piperidin-1-yl)-rifamycin S: The title compound was prepared by using the same procedure as described in step 5-8 of example 4 except (R/S)-4-[(pyrrolidine-3-carbonyl)-amino]-piperidine-1-carboxylic acid tert-butyl ester was used in place of (R/S)-4-pyrrolidin-3-ylmethyl-piperazine-1-carboxylic acid tert-butyl ester. ESI MS m/z 1172.3 (M+Na$^+$). $^1$H NMR (400 MHz, CDCl$_3$) δ (~1:1 mixture of two diastereomers) 13.95 (br s, 1H), 13.25 (s, 1H), 9.00 (d, J=10.4 Hz, 1H), 8.18, 8.17 (two singlets, 1H), 7.60 (s, 1H), 7.08-7.02 (m, 1H), 6.37 (d, J=10.4 Hz, 1H), 6.17-6.08 (m, 2H), 6.07 (d, J=12.4 Hz, 1H), 5.12-5.08 (m, 2H), 4.08-3.77 (m, ~9H), 3.48-3.19 (m, 4H), 3.21-3.16 (m, 1H), 3.10 (s, 3H), 3.08-3.03 (m, 2H), 2.64 (s, 3H), 2.39-2.27

(m, 3H), 2.27 (s, 3H), 2.26-2.12 (m, 2H), 2.12 (s, 3H), 2.09 (s, 3H), 2.00-1.81 (m, 2H), 1.74 (s, 3H), 1.72-1.65 (m, 1H), 1.54-1.48 (m, 1H), 1.24-1.14 (m, 1H), 1.04 (d, J=6.8 Hz, 3H), 1.04-0.96(m, 2H), 0.88 (d, J=7.2 Hz, 3H), 0.71 (d, J=7.2 Hz, 3H), 0.68-0.64 (m, 2H), 0.18 (d, J=6.4 Hz, 3H).

EXAMPLE 7

(S)-3-(4-{[1-(3-Carboxy-1-cyclopropyl-7-fluoro-9-methyl-4-oxo-4H-quinolizine-8-yl)-pyrrolidin-3-yl]-carbamoyl}-piperidin-1-yl)-rifamycin S Step 2. (S)-4-(Pyrrolidin-3-ylcarbamoyl)-piperidine-1-carboxylic acid tert-butyl ester (acetate salt)

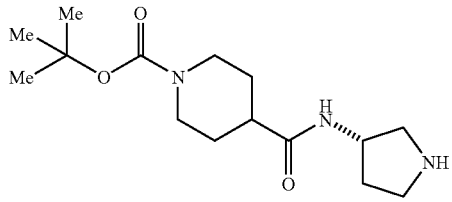

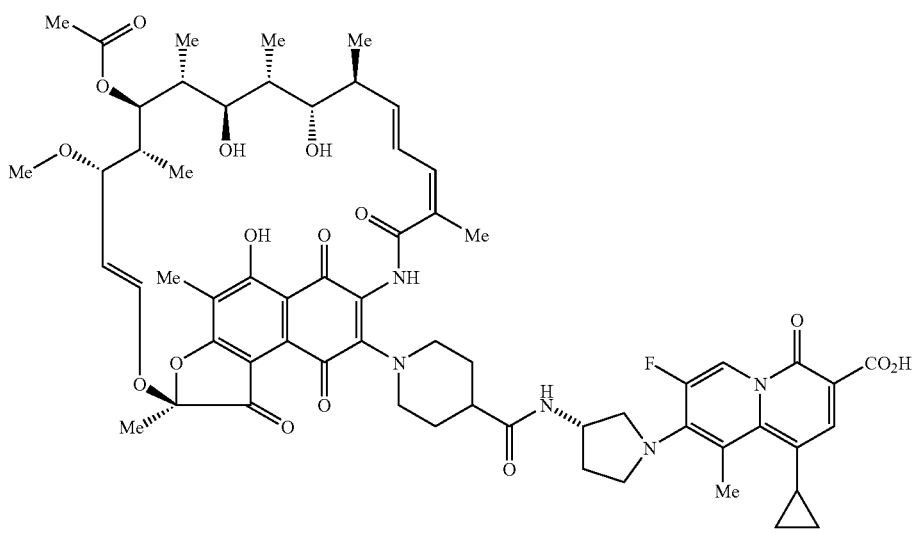

Synthesis: Step 1. (S)-4-(1-Benzyl-pyrrolidin-3-ylcarbamoyl)-piperidine-1-carboxylic acid tert-butyl ester

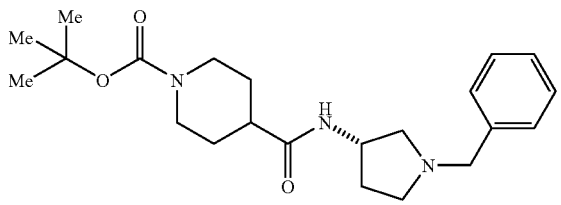

To the solution of piperidine-1,4-dicarboxylic acid mono-tert-butyl ester (1.00 g, 4.36 mmol) and (S)-3-amino-1-benzyl pyrrolidine (769 mg, 4.36 mmol) in dichloromethane (15.0 mL) was added 1-(3-dimethylaminopropyl)-3-ethyl-carbodiimide hydrochloride (1.09 g, 5.67 mmol) and 4-dimethylaminopyridine (80 mg, 0.65 mmol). After stirred at room temperature overnight, the solution was diluted with dichloromethane and washed with water and brine, dried over sodium sulfate, concentrated in vacuo to dryness. The crude solid was triturated with diethyl ether to give pure product as white solid (1.42 g, 84%).

To the solution of product from step 1 (600 mg, 1.55 mmol) in methanol (30 mL) was added acetic acid (0.46 mL) and 30% Pd/C (70 mg, 0.20 mmol). The resulting mixture was hydrogenated under 50 psi hydrogen for 16 hours. The catalyst was filtered off and the solvent removed. The product was yielded as a pale yellow oil (~0.6 g), which was used directly in next step without further purification.

Step 3-6. (S)-3-(4-{[1-(3-Carboxy-1-cyclopropyl-7-fluoro-9-methyl-4-oxo-4H-quinolizine-8-yl)-pyrrolidin-3-yl]-carbamoyl}-piperidin-1-yl)-rifamycin S: The title compound was prepared by using the same procedure as described in step 5-8 in example 1 except (S)-4-(pyrrolidin-3-ylcarbamoyl)-piperidine-1-carboxylic acid tert-butyl ester was used in place of 4-Pyrrolidin-3-ylmethyl-piperazine-1-carboxylic acid tert-butyl ester. ESI MS m/z 1150.5 (M+H$^+$), 1172.5 (M+Na$^+$). $^1$H NMR (400 MHz, CDCl$_3$) δ 13.97 (br s, 1H), 13.35 (s, 1H), 8.76 (d, J=10.0 Hz, 1H), 7.67 (br s, 1H), 7.65 (br s, 1H), 7.52 (br s, 1H), 6.95-6.85 (m, 1H), 6.25 (d, J=11.0 Hz, 1H), 6.09-6.04 (m, 1H), 6.04 (d, J=11.7 Hz, 1H), 5.10-5.03 (m, 2H), 4.61 (br s, 1H), 4.15-3.64 (m, 7H), 3.54-3.41 (m, 4H), 3.28-3.21 (m, 1H), 3.09-2.96 (overlap with Me, m, 2H), 3.07 (s, 3H), 2.58 (s, 3H), 2.52-2.42 (m, 1H), 2.38-1.56 (overlap with 4 Me, m, 8H), 2.22 (s, 3H), 2.06 (s, 3H), 2.05 (s, 3H), 1.74 (s, 3H), 1.24 (s, 1H), 1.22-1.18 (m, 2H), 1.13-1.07 (m, 1H), 1.05-1.01 (m, 1H), 0.98 (d, J=7.0 Hz, 3H), 0.90-0.82 (m, 1H), 0.80 (d, J=7.0 Hz, 3H), 0.65 (d, J=6.3 Hz, 3H), 0.12 (d, J=6.3 Hz, 3H).

EXAMPLE 8

(R/S)-3-(4-{[1-(3-Carboxy-1-cyclopropyl-7-fluoro-9-methyl-4-oxo-4H-quinolizine-8-yl)-pyrrolidin-3-ylmethyl]-carbamoyl}-piperidin-1-yl)-rifamycin S

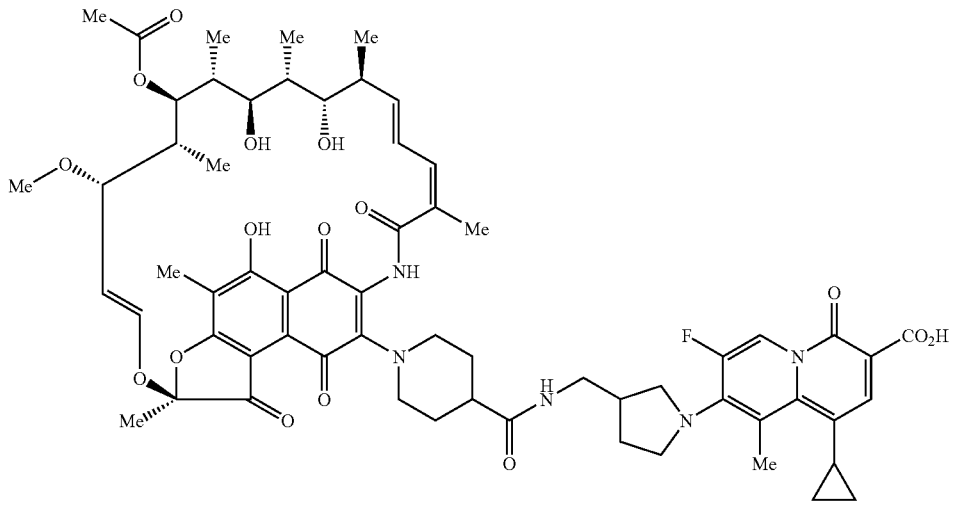

Synthesis: Step 1. (R/S)-4-[(1-tert-Butoxycarbonyl-pyrrolidin-3-ylmethyl)-carbamoyl]-piperidine-1-carboxylic acid tert-butyl ester

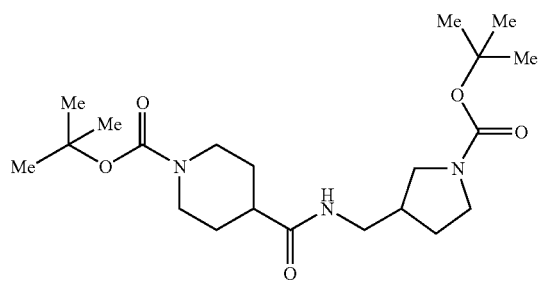

To the solution of 3-aminomethyl-pyrrolidine-1-carboxylic acid tert-butyl ester (269 mg, 1.34 mmol) and piperidine-1,4-dicarboxylic acid mono-tert-butyl ester (310 mg, 1.35 mmol) in dichloromethane (6.0 mL) was added 1-(3-dimethylaminopropyl)-3-ethylcarbodiimide hydrochloride (390 mg, 2.03 mmol) and 4-dimethylaminopyridine (10 mg, 0.08 mmol). After stirred at room temperature for three hours, the solution was partitioned between ethyl acetate and water. The separated organic layer was washed with brine, dried over sodium sulfate and concentrated in vacuo to give a white solid (550 mg, 100%).

Step 2. (R/S)-Piperidine-4-carboxylic acid (pyrrolidin-3-ylmethyl)-amide

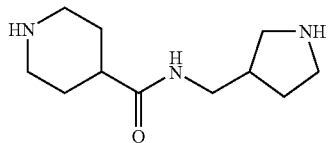

To a stirred solution of product from step 1 (550, 1.3 mmol) in dichloromethane (5.0 mL) was added trifluoroacetic acid (1.8 mL, 20.8 mmol). After stirring at room temperature for 30 minutes, the solution was evaporated to dryness to give an oil (~0.6 g), which was used in next step without purification.

Step 3. (R/S)-1-Cyclopropyl-7-fluoro-9-methyl-4-oxo-8-(3-{[(piperidine-4-carbonyl)-amino]-methyl}-pyrrolidin-1-yl)-4H-quinolizine-3-carboxylic acid ethyl ester:

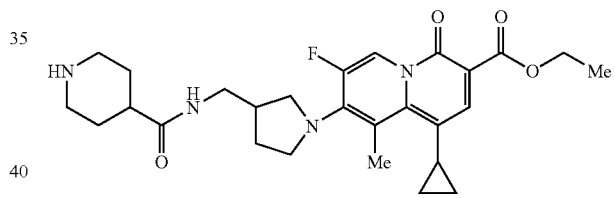

The crude product from step 2 was dissolved in acetonitrile (6.0 mL) and added 8-chloro-1-cyclopropyl-7-fluoro-9-methyl-4-oxo-4H-quinolizine-3-carboxylic acid ethyl ester (324 mg, 1.0 mmol) and NaHCO$_3$ (500 mg, 6.0 mmol). The suspension was heated to reflux for three hours. The resulting solution was partitioned between dichloromethane and water. The separated organic layer was washed with brine, dried over sodium sulfate and concentrated in vacuo to give the title compound as a yellow solid (560 mg, 86%), ESI MS m/z 499.2(M+H$^+$).

Step 4. (R/S)-1-Cyclopropyl-7-fluoro-9-methyl-4-oxo-8-(3-{[(piperidine-4-carbonyl)-amino]-methyl}-pyrrolidin-1-yl)-4H-quinolizine-3-carboxylic acid (trifluoroacetate salt)

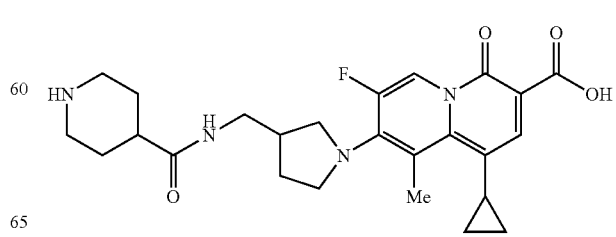

To a solution of product from step 2 (560 mg, 1.1 mmol) in ethanol (10.0 mL) was added the solution of LiOH.H$_2$O (490 mg, 11.7 mmol) in water (5.0 mL). The solution was heated at 60° C. for one hour. Trifluoroacetic acid (1.5 mL, 13 mmol) was added at room temperature. The resulting solution was partitioned between dichloromethane and water. The aqueous phase was extracted with 20% isopropanol in dichloromethane. The combined organic layer was washed with brine, dried over sodium sulfate and concentrated in vacuo to give the title compound as a yellow solid (320 mg, 61%), ESI MS m/z 471.1(M+H$^+$).

Step 5. (R/S)-3-(4-{[1-(3-Carboxy-1-cyclopropyl-7-fluoro-9-methyl-4-oxo-4H-quinolizine-8-yl)-pyrrolidin-3-ylmethyl]-carbamoyl}-piperidin-1-yl)-rifamycin S: The title compound was prepared by using the same procedure as described in step 8 in example 4 except (R/S)-1-cyclopropyl-7-fluoro-9-methyl-4-oxo-8-(3-{[(piperidine-4-carbonyl)-amino]-methyl}-pyrrolidin-1-yl)-4H-quinolizine-3-carboxylic acid (trifluoroacetate salt) was used in place of (R/S)-1-cyclopropyl-7-fluoro-9-methyl-4-oxo-8-(3-piperazin-1-ylmethyl-pyrrolidin-1-yl)-4H-quinolizine-3-carboxylic acid (trifluoroacetate salt). ESI MS m/z 1186.5 (M+Na$^+$). $^1$H NMR (400 MHz, CDCl$_3$) δ (~1:1 mixture of two disstereomers) 13.95 (br s, 1H), 13.33 (s, 1H), 8.92 (d, J=10.0 Hz, 1H), 7.93, 7.91 (two singlets, 1H), 7.59 (s, 1H), 7.02-6.85 (m, 2H), 6.32 (d, J=10.0 Hz, 1H), 6.12 (dd, J=5.2, 15.2 Hz, 1H), 6.07 (d, J=12.0 Hz, 1H), 5.12-5.08 (m, 2H), 4.04-3.19 (m, ~16H), 3.10 (s, 3H), 3.08-2.89 (m, 2H), 2.70-2.65 (m, 1H), 2.60 (s, 3H), 2.46-2.30 (m, 2H), 2.27, 2.26 (two singlets, 3H), 2.24-2.12 (m, 2H), 2.10 (s, 3H), 2.09, 2.08 (two singlets, 3H), 2.00-1.70 (m, 3H), 1.74 (s, 3H), 1.72-1.65 (m, 1H), 1.24-1.14 (m, 1H), 1.06-1.00 (m, 5H), 0.87 (d, J=6.8 Hz, 3H), 0.72-0.64 (m, 5H), 0.18-0.15 (m, 3H).

EXAMPLE 9

(R/S)-3-(4-{[1-(3-Carboxy-1-cyclopropyl-7-fluoro-9-methyl-4-oxo-4H-quinolizine-8-yl)-pyrrolidin-3-ylmethyl]-methyl-amino}-piperidin-1-yl)-rifamycin S Synthesis: Step 1. (R/S)-8-{3-[(1-tert-Butoxycarbonyl-piperidin-4-ylamino)-methyl]-pyrrolidin-1-yl}-1-cyclopropyl-7-fluoro-9-methyl-4-oxo-4H-quinolizine-3-carboxylic acid:

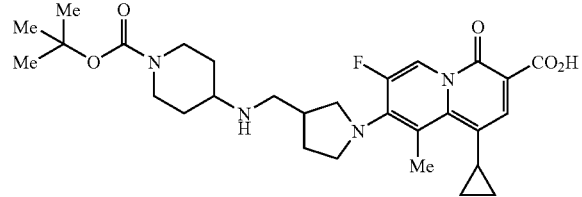

To the solution of 8-(3-aminomethyl-pyrrolidin-1-yl)-1-cyclopropyl-7-fluoro-9-methyl-4-oxo-4H-quinolizine-3-carboxylic acid (trifluoroacetate salt, 102 mg, 0.22 mmol) in methanol (4.0 mL) was added acetic acid (0.66 mL), 4-oxo-piperidine-1-carboxylic acid tert-butyl ester (46 mg, 0.23 mmol) and sodium acetate (144 mg, 1.76 mmol). The solution was stirred at room temperature for two hours and cooled to 0° C. NaBH$_3$CN (32 mg, 0.51 mmol) was added in one portion. The reaction mixture was warmed up to room temperature, stirred for 1.5 hour and partitioned between dichloromethane and water. The separated organic layer was washed with brine, dried over sodium sulfate and concentrated in vacuo to give the title compound as a yellow solid (112 mg, 94%). ESI MS m/z 543.2 (M+H$^+$).

Step 2. (R/S)-8-(3-{[(1-tert-Butoxycarbonyl-piperidin-4-yl)-methyl-amino]-methyl}-pyrrolidin-1-yl)-1-cyclopropyl-7-fluoro-9-methyl-4-oxo-4H-quinolizine-3-carboxylic acid

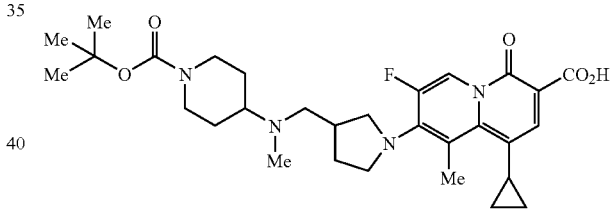

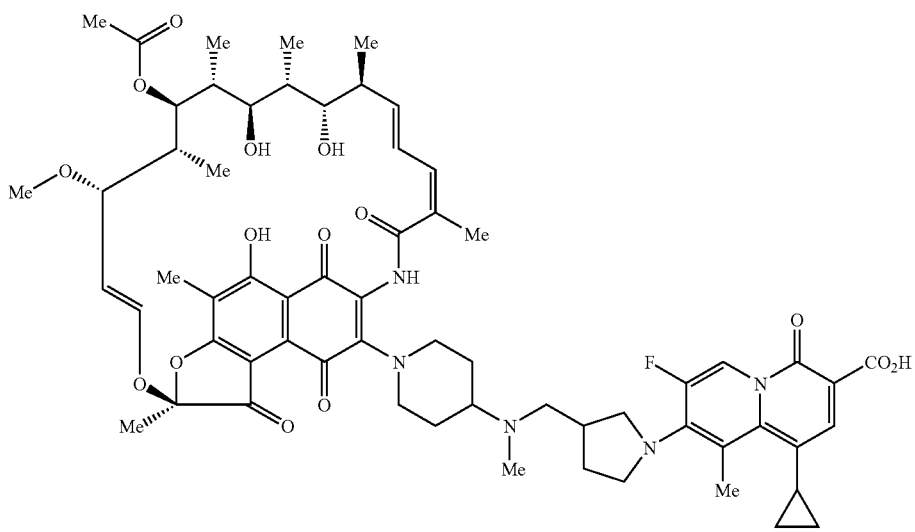

The solution of product from step 1 (42 mg, 0.078 mmol) in MeOH (1 mL) at 0° C. was added acetic acid (0.02 mL) and formaldehyde (37 wt % in water, 25 mg, 0.23 mmol), followed by NaBH$_3$CN (12 mg, 0.19 mmol) and stirred at 0° C. for one hour. Reaction mixture was diluted with dichloromethane, washed with water twice, washed with brine, dried over sodium sulfate, and concentrated in vacuo to give the title compound as yellow solid (43 mg, 98%). ESI MS m/z: 557.2 (M+H$^+$).

Step 3-4. (R/S)-3-(4-{[1-(3-Carboxy-1-cyclopropyl-7-fluoro-9-methyl-4-oxo-4H-quinolizine-8-yl)-pyrrolidin-3-ylmethyl]-methyl-amino}-piperidin-1-yl)-rifamycin S: The title compound was prepared by using the same procedure as described in step 7-8 of example 4 except (R/S)-8-(3-{[(1-tert-Butoxycarbonyl-piperidin-4-yl)-methyl-amino]-methyl}-pyrrolidin-1-yl)-1-cyclopropyl-7-fluoro-9-methyl-4-oxo-4H-quinolizine-3-carboxylic acid was used in place of (R/S)-8-[3-(4-tert-butoxycarbonyl-piperazin-1-ylmethyl)-pyrrolidin-1-yl]-1-cyclopropyl-7-fluoro-9-methyl-4-oxo-4H-quinolizine-3-carboxylic acid. ESI MS m/z 1150.2 (M+H$^+$), 1172.2 (M+Na$^+$). $^1$H NMR (400 MHz, CDCl$_3$) δ 13.87 (br s, 1H), 13.28 (br s, 1H), 9.03 (d, J=10.2 Hz, 1H), 8.17 (s, 1H), 7.46 (s, 1H), 7.10-7.04 (m, 1H), 6.28 (d, J=11.0 Hz, 1H), 6.19-6.12 (m, 1H), 6.00 (d, J=12.5 Hz, 1H), 5.05-5.00 (m, 2H), 4.00-3.68 (m, 5H), 3.60-3.36 (m, 4H), 3.34-3.26 (m, 1H), 3.09 (s, 3H), 3.08-3.30 (m, 4H), 2.62-2.60 (m, 2H), 2.54-2.46 (m, 2H), 2.40-1.56 (overlap with 5 Me, m, 10H), 2.30 (s, 3H), 2.26 (s, 3H), 2.11 (s, 3H), 2.08 (s, 3H), 1.74 (s, 3H), 1.40-1.11 (overlap with Me, m, 2H), 1.34 (s, 3H), 1.02 (d, J=7.0 Hz, 3H), 0.98-0.91 (m, 1H), 0.86 (d, J=7.0 Hz, 3H), 0.69 (d, J=6.3 Hz, 3H), 0.67-0.63 (m, 1H), 0.16 (d, J=7.0 Hz, 3H).

EXAMPLE 10

(R)-3-(4-{[1-(3-Carboxy-1-cyclopropyl-7-fluoro-9-methyl-4-oxo-4H-quinolizine-8-yl)-pyrrolidin-3-ylmethyl]-methyl-amino}-piperidin-1-yl)-rifamycin S Synthesis: Title compound was prepared by using the same procedures as described for Example 9 except (R)-(8-(3-aminomethyl-pyrrolidin-1-yl)-1-cyclopropyl-7-fluoro-9-methyl-4-oxo-4H-quinolizine-3-carboxylic acid (trfluoroacetate salt was used in place of (R/S)-(8-(3-aminomethyl-pyrrolidin-1-yl)-1-cyclopropyl-7-fluoro-9-methyl-4-oxo-4H-quinolizine-3-carboxylic acid (trfluoroacetate salt) in step 1. ESI MS m/z 1150.3 (M+H$^+$), 1172.3 (M+Na$^+$). $^1$H NMR (400 MHz, CDCl$_3$) δ 13.77 (br s, 1H), 13.19 (br s, 1H), 8.92 (d, J=11.0 Hz, 1H), 8.07 (s, 1H), 7.40 (s, 1H), 6.91-6.89 (m, 1H), 6.19 (d, J=11.0 Hz, 1H), 6.18-6.09 (m, 1H), 5.90 (d, J=12.5 Hz, 1H), 4.98-4.92 (m, 2H), 3.86-3.54 (m, 5H), 3.44-3.24 (m, 4H), 3.18-3.12 (m, 1H), 2.96 (s, 3H), 2.98-2.76 (overlap with Me, m, 4H), 2.47 (s, 3H), 2.38-2.28 (m, 2H), 2.24-1.30 (overlap with 5 Me, m, 10H), 2.15 (s, 3H), 2.11 (s, 3H), 1.96 (s, 3H), 1.93 (s, 3H), 1.58 (s, 3H), 1.16-1.02 (m, 2H), 0.90-0.76 (overlap with Me, m, 2H), 0.87 (d, J=7.0 Hz, 3H), 0.71 (d, J=7.0 Hz, 3H), 0.54 (d, J=7.0 Hz, 3H), 0.54-0.46 (m, 2H), 0.01 (d, J=6.3 Hz, 3H).

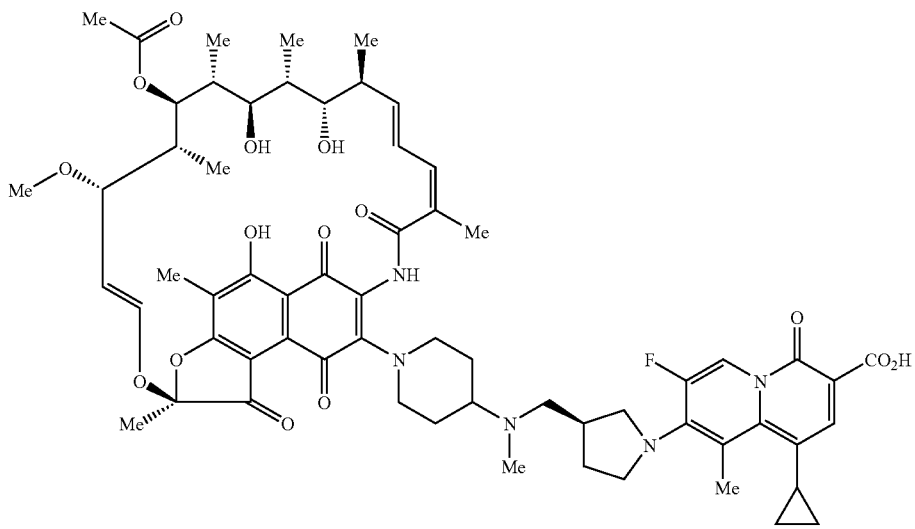

EXAMPLE 11

(R/S)-3-{4-[1-(3-Carboxy-1-cyclopropyl-7-fluoro-9-methyl-4-oxo-4H-quinolizine-8-yl)-pyrrolidin-3-ylmethoxy]-piperidin-1-yl}-rifamycin S

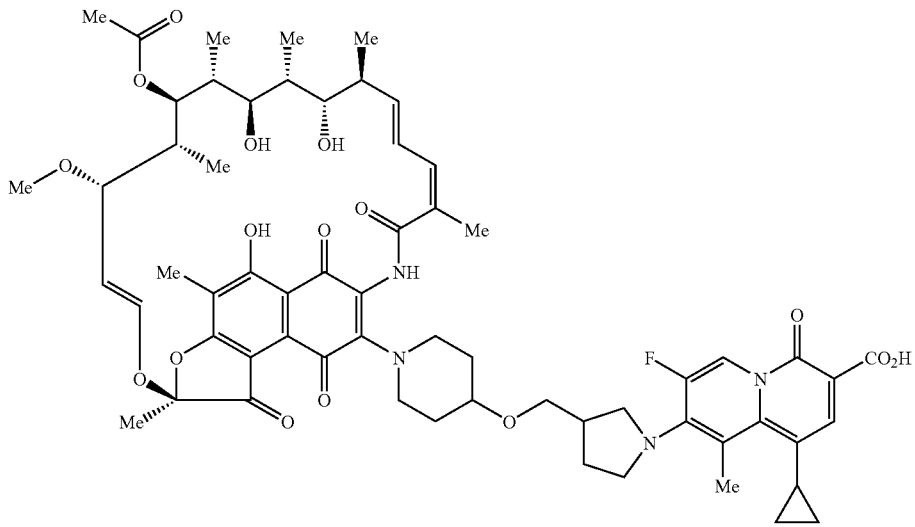

Step 1. (R/S)-1-Benzyl-pyrrolidine-3-carboxylic acid:

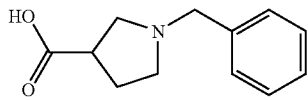

To the solution of acrylic acid (1.57 g, 21.8 mmol) and N-(methoxymethyl)-N-(trimethylsilylmethyl)benzylamine (5.5 mL, 21.5 mmol) in toluene (30 mL) was added trifluoroacetic acid (50 μL, 0.65 mmol). The resulting solution was stirred at room temperature for two hours and condensed to give a colorless oil (~4.3 g), which was used in next step without further purification.

Step 2. (R/S)-(1-Benzyl-pyrrolidin-3-yl)-methanol

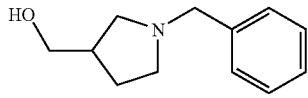

The solution of lithium aluminumhydride (1N solution in THF, 22 mL) was added dropwise to the solution of the colorless oil from step 1 in anhydrous THF (30 mL) at 0° C. The resulting mixture was warmed to room temperature in two hours and quenched with ice-water very carefully. The mixture was extracted with ethyl acetate twice. The combined organic layer was washed with brine, dried over sodium sulfate and concentrated in vacuo to give a colorless oil (3.6 g, 88% in two steps) which was used in next step directly.

Step 3. (R/S)-Methanesulfonic acid 1-benzyl-pyrrolidin-3-ylmethyl ester

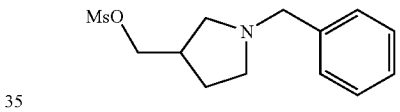

To the solution of the product from step 2 (583 mg, 3.05 mmol) and triethylamine (0.64 mL, 4.59 mmol) in dichloromethane (10.0 mL) was added methanesulfonyl chloride (0.26 mL, 3.34 mmol) dropwise. The resulting solution was stirred at room temperature for 30 minutes and then partitioned between ethyl acetate and water. The separated organic layer was washed with brine, dried over sodium sulfate, concentrated in vacuo to give a yellow oil (720 mg, 88%), which was used directly in next step.

Step 4. (R/S)-4-(1-Benzyl-pyrrolidin-3-ylmethoxy)-piperidine-1-carboxylic acid tert-butyl ester:

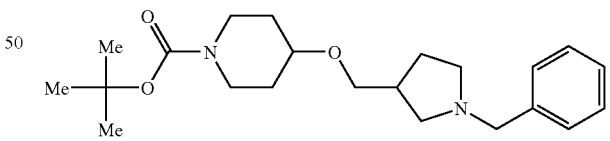

To the solution of 4-hydroxy-piperidine-1-carboxylic acid tert-butyl ester (1.61 g, 8.02 mmol) in DMF (16 mL) was added sodium hydride (60% in mineral oil, 532 mg, 13.3 mmol) followed by the solution of the product from step 3 (0.72 g, 2.67 mmol) in DMF (2.0 mL) after 20 minutes. The resulting mixture was heated at 80° C. overnight and quenched carefully with water. The mixture was partitioned between ethyl acetate and water. The separated organic layer was washed with brine, dried over sodium sulfate and concentrated in vacuo. The residue was purified by flash chromatography on silica gel (20-50% ethyl acetate/hexane) to give a white solid (0.60 g, 60%). ESI MS m/z 375.2 (M+H$^+$).

Step 5. (R/S)-4-(Pyrrolidin-3-ylmethoxy)-piperidine-1-carboxylic acid tert-butyl ester:

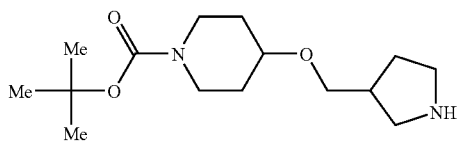

To the solution of product from step 4 (276 mg, 0.74 mmol) in acetic acid (10.0 mL) was added 30% Pd/C (120 mg). The resulting mixture was hydrogenated at 50 Psi for 16 hours. The catalyst was filtered off and the solvent removed. The product was yielded as a pale yellow oil (~200 mg), which was used in next step directly.

Step 6-9. (R/S)-3-{4-[1-(3-Carboxy-1-cyclopropyl-7-fluoro-9-methyl-4-oxo-4H-quinolizine-8-yl)-pyrrolidin-3-ylmethoxy]-piperidin-1-yl}-rifamycin S: The title compound was prepared by using the same procedure as described in step 5-8 of example 4 except (R/S)-4-(pyrrolidin-3-ylmethoxy)-piperidine-1-carboxylic acid tert-butyl ester was used in place of (R/S)-4-pyrrolidin-3-ylmethyl-piperazine-1-carboxylic acid tert-butyl ester. ESI MS m/z 1159.5 (M+Na+). $^1$H NMR (400 MHz, CDCl$_3$) δ (~1:1 mixture of two diastereomers) 13.87, 13.86 (two singlets, 1 H), 13.27 (s, 1H), 9.07 (d, J=10.4 Hz, 1H), 8.22 (s, 1H), 7.52 (s, 1H), 7.02-6.96 (m, 1H), 6.29 (d, J=10.8 Hz, 1H), 6.11 (dd, J=6.0, 15.2 Hz, 1H), 6.02 (d, J=12.4 Hz, 1H), 5.08-5.03 (m, 2H), 3.93 (d, J=8.8 Hz, 1H), 3.86 (d, J=11.2 Hz, 1H), 3.80-3.12 (m, ~15H), 3.06 (s, 3H), 3.02-2.97 (m, 1H), 2.58 (s, 3H), 2.58-2.52 (m, 1H), 2.34-2.28 (m, 1H), 2.22 (s, 3H), 2.28-2.19 (m, 2H), 2.07 (s, 3H), 2.04 (s, 3H), 2.04-1.98 (m, 1H), 1.92-1.72 (m, 3H), 1.70 (s, 3H), 1.68-1.60(m, 1H), 1.22-1.08 (m, 1H), 0.99 (d, J=7.2 Hz, 3H), 0.98-0.90 (m, 2H), 0.82 (d, J=6.8 Hz, 3H), 0.65 (d, J=7.2 Hz, 3H), 0.65-0.58 (m, 2H), 0.13 (d, J=6.8 Hz, 3H).

EXAMPLE 12

(R/S)-3-(4-{1-[1-(3-Carboxy-1-cyclopropyl-7-fluoro-9-methyl-4-oxo-4H-quinolizine-8-yl)-pyrrolidin-3-yl]-cyclopropylamino}-piperidin-1-yl)-rifamycin S Synthesis Step 1. 4-Benzylamino-piperidine-1-carboxylic acid tert-butyl ester:

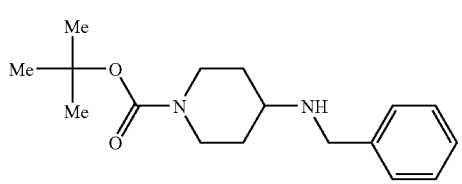

To the solution of 4-amino-piperidine-1-carboxylic acid tert-butyl ester (660 mg, 3.30 mmol) and benzaldehyde (0.34 mL, 3.36 mmol) in methanol (6.0 mL) was added acetic acid (20 μL, 0.32 mmol). After 15 minutes, NaBH$_3$CN (304 mg, 4.8 mmol) was added in two portions. The resulting solution was stirred at room temperature for 30 minutes and then partitioned between ethyl acetate and water. The separated organic layer was washed with brine, dried over sodium sulfate and concentrated in vacuo to give a colorless oil (0.96 g).

Step 2. 4-(Acryloyl-benzyl-amino)-piperidine-1-carboxylic acid tert-butyl ester:

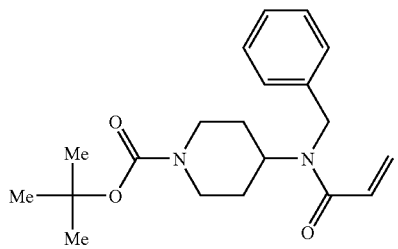

To the solution of the product from step 1 (0.96 g, 3.3 mmol) and acrylic acid (0.25 mL, 3.6 mmol) in dichloromethane (10.0 mL) was added 1-(3-dimethylaminopropyl)-3-ethyl-carbodiimide hydrochloride (0.87 g, 4.5 mmol) followed by

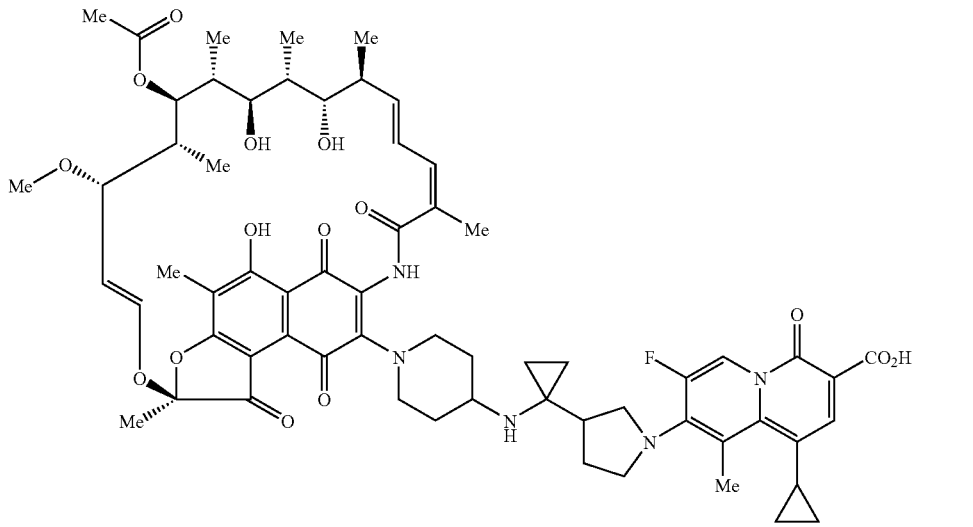

4-dimethylaminopyridine (10 mg, 0.08 mol). After stirred at room temperature overnight, the solution was partitioned between ethyl acetate and water. The separated organic layer was washed with brine, dried over sodium sulfate and concentrated in vacuo to give a colorless oil (~1.0 g). ESI MS m/z 367.1 (M+Na+).

Step 3. (R/S)-4-[Benzyl-(1-benzyl-pyrrolidine-3-carbonyl)-amino]-piperidine-1-carboxylic acid tert-butyl ester:

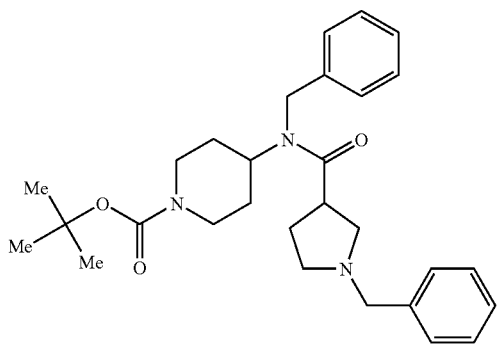

To the solution of the product from step 2 (1.1 g, 3.2 mmol) and N-(methoxymethyl)-N-(trimethylsilylmethyl)benzylamine (0.84 mL, 3.3 mmol) in dichloromethane (10 mL) was added trifluoroacetic acid (40 μL, 0.35 mmol). The resulting solution was stirred at room temperature for four hours and condensed to give a colorless oil, which was purified by flash chromatography on silica gel with 2-10% methanol in dichloromethane to give a white solid (0.36 g, 23% in three steps). ESI MS m/z 478.3 (M+H+).

Step 4: (R/S)-4-{Benzyl-[1-(1-benzyl-pyrrolidin-3-yl)-cyclopropyl]-amino}-piperidine-1-carboxylic acid tert-butyl ester:

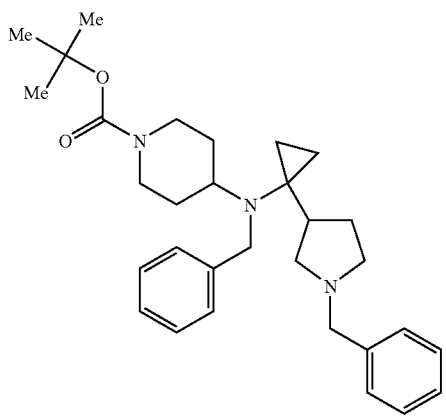

The solution of ethylmagnesium bromide (3.0 M in ethyl ether, 0.64 mL, 1.92 mmol) in THF (5.0 mL) was cooled to −78° C. To this solution was added the solution of titanium (IV) isopropoxide (0.23 mL, 0.78 mmol) in THF (0.5 mL) dropwise with the temperature below −70° C. After stirred for three minutes, the solution of the product from step 3 (0.36 g, 0.75 mmol) in THF (0.5 mL) was added. The resulting solution was warmed to room temperature, heated to reflux for one hour and then cooled to 8° C. Ethylmagnesium bromide (3.0M in ethyl ether, 0.53 mL, 1.59 mmol) was added followed by the solution of titanium (IV) isopropoxide (0.20 mL, 0.68 mmol) in THF (0.5 mL) rapidly. The reaction mixture was stirred at room temperature for one hour and partitioned between ethyl acetate and water. The separated organic layer was washed with brine, dried over sodium sulfate and concentrated in vacuo. The residue was purified by preparative thin layer chromatography (60% ethyl acetate in hexane with 0.5% triethylamine) to give a pale yellow oil (190 mg, 52%). ESI MS m/z 490.3 (M+H+).

Step 5. (R/S)-4-(1-Pyrrolidin-3-yl-cyclopropylamino)-piperidine-1-carboxylic acid tert-butyl ester:

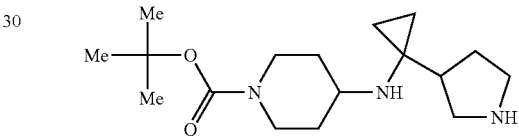

To a solution of the product from step 4 (190 mg, 0.39 mmol) in acetic acid (6.0 mL) was added 30% Pd/C (100 mg). The resulting mixture was hydrogenated under 50 Psi for 60 hours. The catalyst was filtered off and the solvent removed. The product was yielded as a pale yellow oil (~120 mg) which could be used in next step directly. ESI MS m/z 310.1 (M+H+).

Step 6-9. (R/S)-3-(4-{1-[1-(3-Carboxy-1-cyclopropyl-7-fluoro-9-methyl-4-oxo-4H-quinolizine-8-yl)-pyrrolidin-3-yl]-cyclopropylamino}-piperidin-1-yl)-rifamycin S: The title compound was prepared by using the same procedure as described in step 5-8 of example 4 except (R/S)-4-(1-pyrrolidin-3-yl-cyclopropylamino)-piperidine-1-carboxylic acid tert-butyl ester was used in place of (R/S)-4-pyrrolidin-3-ylmethyl-piperazine-1-carboxylic acid tert-butyl ester. ESI MS m/z 1184.5 (M+Na+). 1H NMR (400 MHz, CDCl3) δ (~1:1 mixture of two diastereomers) 13.85 (s, 1H), 13.27 (s, 1H), 9.06 (d, J=10.4 Hz, 1H), 8.21 (s, 1H), 7.51 (s, 1H), 7.02-6.98 (m, 1H), 6.32-6.27 (m, 1H), 6.18-6.12 (m, 1H), 6.01 (d, J=12.4 Hz, 1H), 5.07-5.01 (m, 2H), 3.96-3.84(m, 4H), 3.60-3.24 (m, ~8H), 3.05 (s, 3H), 3.02-2.89 (m, 3H), 2.68-2.60 (m, 1H), 2.59, 2.58 (two singlets, 3H), 2.32-2.26 (m, 1H), 2.21 (s, 3H), 2.18-2.12 (m, 1H), 2.08, 2.06 (two singlets, 3H), 2.04 (s, 3H), 1.90-1.71 (m, ~6H), 1.69 (s, 3H), 1.60-1.32 (m, 2H), 1.19-1.12 (m, 1H), 1.08-0.98 (m, 4H), 0.89-0.80 (m, 5H), 0.67-0.56 (m, 8H), 0.12-0.10 (m, 3H).

EXAMPLE 13

(R/S)-3-(4-{[1-(3-Carboxy-1-cyclopropyl-7-fluoro-9-methyl-4-oxo-4H-quinolizine-8-yl)-3-trifluoromethyl-pyrrolidin-3-ylmethyl]-amino}-piperidin-1-yl)-rifamycin S

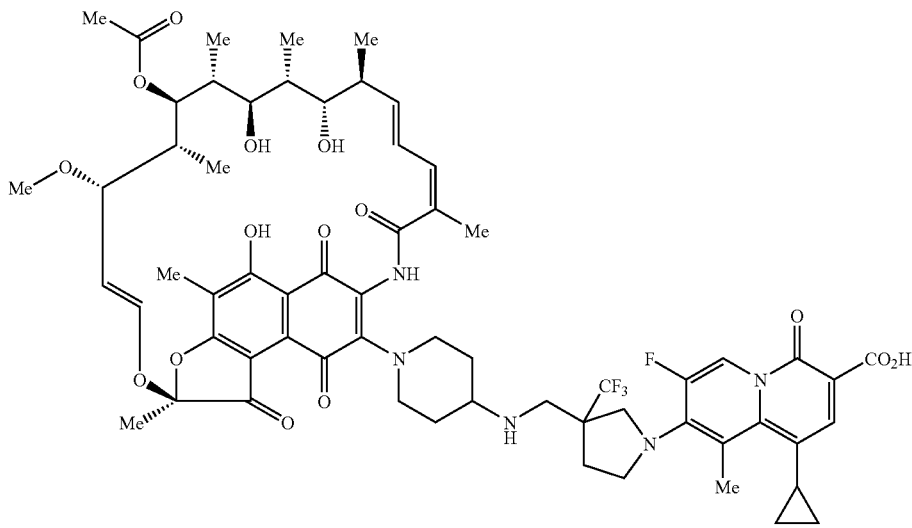

Synthesis: Step 1. (R/S)-1-Benzyl-3-trifluoromethyl-pyrrolidine-3-carboxylic acid methyl ester:

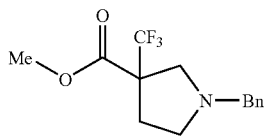

To the solution of 2-trifluoromethyl-acrylic acid methyl ester (957 mg, 6.21 mmol) and N-(methoxymethyl)-N-(trimethylsilylmethyl)-benzylamine (1.60 mL, 6.25 mmol) in dichloromethane (6.0 mL) was added trifluoroacetic acid (20 µL, 0.18 mmol). The resulting solution was stirred at room temperature for 30 minutes and condensed to give a colorless oil (1.74 g, 98%), which could be used in next step without purification.

Step 2. (R/S)-(1-Benzyl-3-trifluoromethyl-pyrrolidin-3-yl)-methanol:

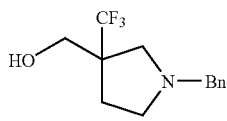

The solution of lithium aluminumhydride (1N solution in THF, 6.2 mL) was added dropwise to the solution of the product from step 1 (1.74 g, 6.06 mmol) in anhydrous THF (20 mL) at −70° C. The resulting mixture was warmed up to −30° C. in two hours and quenched with ice-water very carefully. The mixture was extracted with dichloromethane twice. The combined organic layer was washed with brine, dried over sodium sulfate and concentrated in vacuo to give colorless oil (1.47 g, 94%) which could be used in next step directly.

Step 3. (R/S)-1'-Benzyl-3-trifluoromethyl-pyrrolidine-3-carbaldehyde:

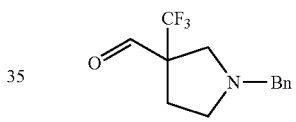

Oxalyl chloride (2.0 M in dichloromethane, 0.63 mL, 1.26 mmol) was added dropwise to the solution of DMSO (0.18 mL, 2.53 mmol) in dichloromethane (2.0 mL) at −70° C. The solution of the product from step 2 (260 mg, 1.00 mmol) in dichloromethane (2.8 mL) was added at the same temperature. The resulting solution was stirred at −70° C. for 1.5 hours, and then triethylamine (0.6 mL, 4.30 mmol) was added. Stirring was continued for 15 minutes without the cooling bath. The mixture was partitioned between dichloromethane and water. The separated organic layer was washed with brine, dried over sodium sulfate and concentrated in vacuo to give a colorless oil (240 mg, 93%). $^1$H NMR (400 MHz, CDCl$_3$) δ 9.63 (s, 1H), 7.35-7.27 (m, 5H), 3.68 (d, J$_{AB}$=13.2 Hz, 1H), 3.62 (d, J$_{AB}$=13.2 Hz, 1H), 3.12 (d, J=10.8 Hz, 1H), 2.89-2.83 (m, 1H), 2.69 (d, J=10.8 Hz, 1H), 2.59-2.53 (m, 1H), 2.39-2.32 (m, 1H), 2.16-2.10 (m, 1H).

Step 4: (R/S)-4-[(1-Benzyl-3-trifluoromethyl-pyrrolidin-3-ylmethyl)-amino]-piperidine-1-carboxylic acid tert-butyl ester:

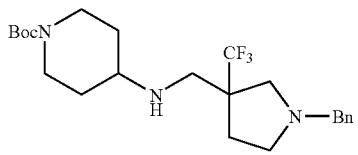

To the solution of 4-amino-piperidine-1-carboxylic acid tert-butyl ester (250 mg, 1.25 mmol) and product from step 3 (240 mg, 0.93 mmol) in methanol (3.0 mL) was added acetic acid (80 μL, 1.29 mmol). The solution was stirred at room temperature for one hour and then NaBH₃CN (150 mg, 2.39 mmol) was added in three portions. The reaction mixture was stirred at room temperature for one hour and partitioned between ethyl acetate and water. The separated organic layer was washed with water, washed with brine, dried over sodium sulfate and concentrated in vacuo. The residue was purified by flash chromatography on silica gel (30% ethyl acetate in hexane) to give a pale yellow oil (350 mg, 85%). ESI MS m/z 442.1 (M+H⁺).

Step 5. (R/S)-4-[(3-Trifluoromethyl-pyrrolidin-3-ylmethyl)-amino]-piperidine-1-carboxylic acid tert-butyl ester:

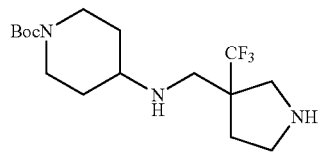

To the solution of the product from step 4 (240 mg, 0.54 mmol) in acetic acid (5.0 mL) was added 20% Pd(OH)₂/C (90 mg). The resulting mixture was hydrogenated at 1 atm under hydrogen balloon for 60 hours. The catalyst was filtered off and the solvent removed. The product was yield as a pale yellow oil (~120 mg), which was used in next step directly.

Step 6-9. (R/S)-3-(4-{[1-(3-Carboxy-1-cyclopropyl-7-fluoro-9-methyl-4-oxo-4H-quinolizine-8-yl)-3-trifluoromethyl-pyrrolidin-3-ylmethyl]-amino}-piperidin-1-yl)-rifamycin S: The title compound was prepared by using the same procedure as described in step 5-8 of example 4 except (R/S)-4-[(3-trifluoromethyl-pyrrolidin-3-ylmethyl)-amino]-piperidine-1-carboxylic acid tert-butyl ester was used in place of (R/S)-4-pyrrolidin-3-ylmethyl-piperazine-1-carboxylic acid tert-butyl ester. ESI MS m/z 1204.5 (M+Na⁺). ¹H NMR (400 MHz, CDCl₃) δ (~1:1 mixture of two diastereomers) 13.87 (br s, 1 H), 13.31 (s, 1H), 9.18, 9.17 (two doublets, J=10.0 Hz, 1H), 8.33 (s, 1H), 7.59 (s, 1H), 7.05-7.00 (m, 1H), 6.34 (d, J=10.8 Hz, 1H), 6.16 (dd, J=6.0, 15.2 Hz, 1H), 6.07 (d, J=12.4 Hz, 1H), 5.11-5.07 (m, 2H), 4.01-3.75 (m, ~8H), 3.50 (s, 3H), 3.50-3.38 (m, 2H), 3.31-3.27 (m, 1H), 3.11 (s, 3H), 3.08-2.89 (m, 4H), 2.70 (s, 3H), 2.70-2.65 (m, 1H), 2.38-2.30 (m, 1H), 2.27 (s, 3H), 2.26-2.12 (m, 2H), 2.11 (s, 3H), 2.09 (s, 3H), 2.00-1.90 (m, 2H), 1.75, 1.74 (two singlets, 3H), 1.74-1.66 (m, 2H), 1.42-1.32 (m, 1H), 1.24-1.14 (m, 1H), 1.05-1.00 (m, 5H), 0.87 (d, J=6.8 Hz, 3H), 0.72-0.67 (m, 5H), 0.18-0.15 (m, 3H).

EXAMPLE 14

(R/S)-3-{4-[1-(3-Carboxy-1-cyclopropyl-7-fluoro-9-methyl-4-oxo-4H-quinolizine-8-yl)-pyrrolidin-3-yl]-piperidin-1-yl}-rifamycin S

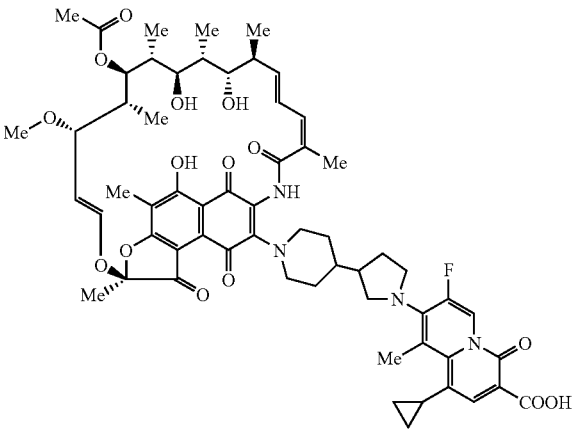

Synthesis: Step 1. (R/S)-4-(1-Benzyl-pyrrolidin-3-yl)-pyridine:

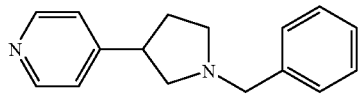

To the solution of 4-vinyl-pyridine (3.0 g, 28.5 mmol) and N-(methoxymethyl)-N-(trimethylsilylmethyl)benzylamine (7.3 mL, 25.3 mmol) in toluene (25 mL) was added trifluoroacetic acid (0.30 mL, 3.9 mmol). The resulting solution was stirred at room temperature overnight and condensed. The residue oil was purified by flash chromatography on silica gel (5% methanol in dichloromethane) to give a clear oil (~4.5 g, 66%).

Step 2. (R/S)-4-Pyrrolidin-3-yl-piperidine:

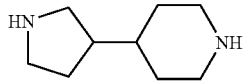

The oil from step 1 (320 mg, 1.34 mmol) was dissolved in acetic acid (10 mL) and trifluoroacetic acid (1 mL), and 30% Pd/C (200 mg) was added. The mixture was hydrogenated at 40 psi for 72 hours. The catalyst was filtered, and acids were removed. The solution of residue in THF (7.0 mL) was added NaHCO₃ (680 mg, 8 mmol), triethylamine (0.56 mL, 4 mmol) and di-tert-butyl dicarbonate (1.47 g, 6.75 mmol). The mixture was allowed to stir at 60° C. under nitrogen for 18 hours. THF was removed and the residue was partitioned between ethyl acetate and water. The organic layer was separated, and aqueous layer was extracted with ethyl acetate. The combined extracts were washed with brine and dried over Na₂SO₄. The solution was condensed and purified by preparative thin layer chromatography (100% ethyl acetate) to give 4-(1-tert-butoxycarbonyl-pyrrolidin-3-yl)- piperidine-1-carboxylic acid tert-butyl ester as a clear oil (240 mg, 50%). ESI MS m/z 377.1 (M+Na+). This oil was dissolved in trifluoroacetic acid (1.8 mL) in 1,2-dichloroethane (4.2 mL). The mixture was allowed to stir at room temperature for two hours. Solvent was removed and the residue (light brown syrup) was carried to the next step without purification.

Step 3. (R/S)-1-Cyclopropyl-7-fluoro-9-methyl-4-oxo-8-(3-piperidin-4-yl-pyrrolidin-1-yl)-4H-quinolizine-3-carboxylic acid (trifluoroacetate salt, Major) and (R/S)-1-cyclopropyl-7-fluoro-9-methyl-4-oxo-8-(4-pyrrolidin-3-yl-piperidin-1-yl)-4H-quinolizine-3-carboxylic acid (trifluoroacetate, Minor):

Major

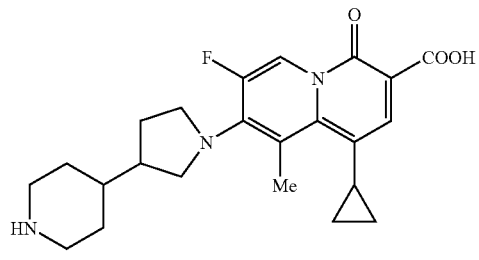

Minor

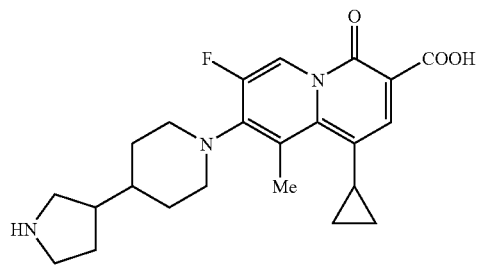

The title compounds, the mixtures of two regioisomers (>7:3), was prepared by using the same procedure as described in step 3-4 of example 11 except 4-pyrrolidin-3-yl-piperidine was used in place of piperidine-4-carboxylic acid (pyrrolidin-3-ylmethyl)-amide. ESI MS m/z 414.1 (M+H+).

Step 4. (R/S)-3-{4-[1-(3-Carboxy-1-cyclopropyl-7-fluoro-9-methyl-4-oxo-4H-quinolizine-8-yl)-pyrrolidin-3-yl]-piperidin-1-yl}-rifamycin S: The title compound, as the only regioisomer separated, was prepared by using the same procedure as described in step 8 of example 4 except the product from step 3 was used in place of (R/S)-1-cyclopropyl-7-fluoro-9-methyl-4-oxo-8-(3-piperazin-1-ylmethyl-pyrrolidin-1-yl)-4H-quinolizine-3-carboxylic acid (trifluoroacetate salt). ESI MS m/z 1107.5 (M+H+); 1H NMR (400 MHz, CDCl3) δ 13.88 (s, 1 H), 13.29 (s, 1 H), 9.08 (d, J=10.7 Hz, 1 H), 8.24 (d, J=7.1 Hz, 1 H), 7.53 (s, 1 H), 7.08 (m, 1 H), 6.33 (d, J=10.7 Hz, 1 H), 6.14 (dd, J=3.3, 15.6 Hz, 1 H), 6.04 (d, J=12.4 Hz, 1 H), 5.08 (d, J=9.9 Hz, 1 H), 3.95 (br s, 1 H), 3.90 (d, J=9.2 Hz, 1 H), 3.67-3.24 (m, 3 H), 3.07 (s, 3 H), 3.01 (br s, 1 H), 2.58 (s, 3 H), 2.35 (m, 1 H), 2.24 (s, 3 H), 2.15 (m, 2 H), 2.10 (s, 3 H), 2.06 (s, 3 H), 1.83 (m, 4 H), 1.72 (d, J=13.3 Hz, 3 H), 1.66 (m, 1H), 1.39 (m, 1 H), 1.04 (m, 2 H), 1.01 (d, J=7.2 Hz, 3H), 0.85 (d, J=7.0 Hz, 3 H), 0.84 (m, 2 H), 0.69 (d, J=6.3 Hz, 3 H), 0.16 (d, J=7.0 Hz, 3 H).

EXAMPLE 15

3-[5-(3-Carboxy-1-cyclopropyl-7-fluoro-9-methyl-4-oxo-4H-quinolizin-8-yl)-hexahydro-pyrrolo[3,4-c]pyrrol-2-yl]-rifamycin S

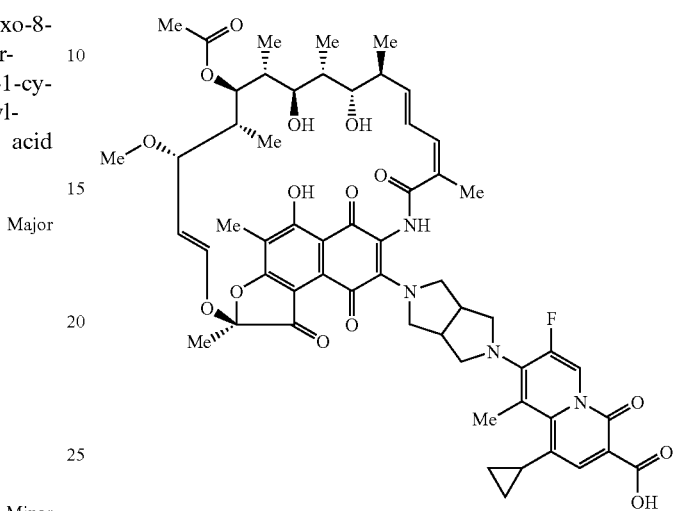

Synthesis: Step 1. 2,5-Dibenzyl-tetrahydro-pyrrolo[3,4-c]pyrrole-1,3-dione:

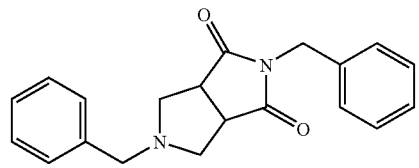

N-Benzylmaleimide (5.0 g, 26.7 mmol), and N-(methoxymethyl)-N-(trimethylsilylmethyl) benzylamine (7.0 g, 29.4 mmol) were dissolved in toluene (150 mL). Trifluoroacetic acid (500 µL, 6.5 mmol) was added at room temperature. The reaction was allowed to stir for two hours at room temperature, and the precipitate was filtered off (~440 mg). The filtrate was concentrated and purified by silica gel column chromatography (20-50% ethyl acetate in hexanes) to afford a white solid (6.2 g, 72%). 1H NMR (400 MHz, CDCl3): δ 7.22-7.05 (m, 8H), 7.01-6.96 (m, 2H), 4.45 (s, 2H), 3.95 (s, 2H), 3.50 (d, J=11.0 Hz), 3.37 (d, J=8.8 Hz), 3.10 (app t, J=9.1 Hz); 13C NMR (400 MHz, CDCl3): δ 175.8 (C=O), 134.8 (Ph), 130.6 (Ph), 129.6 (Ph), 129.3 (Ph), 128.8 (Ph), 128.6 (Ph), 128.3 (Ph), 127.7 (Ph), 57.3 (CH2), 54.0 (CH2), 42.9 (CH), 42.6 (CH2).

Step 2. 2,5-Dibenzyl-octahydro-pyrrolo[3,4-c]pyrrole

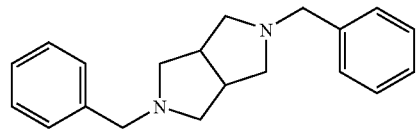

2,5-Dibenzyl-tetrahydro-pyrrolo[3,4-c]pyrrole-1,3-dione (6.0 g, 18.7 mmol) was dissolved in dry dioxane (100 mL). Lithium aluminumhydride (1.0 M in THF, 37.5 mL, 37.5 mmol) was added dropwise and the resulting clear solution was heated at reflux for 20 hours. The reaction was cooled and carefully quenched by the addition of THF/H$_2$O (2:1/v:v). The gelatinous mixture was filtered through Celite, and the filter cake was washed with ethyl acetate (3×25 mL) then with MeOH (3×25 mL). The filtrate was concentrated and purified by silica gel column chromatography (20-50% ethyl acetate in hexanes) to afford a light yellow oil (3.8 g, 69%). $^1$H NMR (400 MHz, CDCl$_3$): δ 7.39-7.32 (m, 8H), 7.30-7.25 (m, 2H), 3.63 (s, 2H), 2.77-2.69 (br m, 2H), 2.66 (app t, J=8.1 Hz, 4H), 2.37 (dd, J=8.8, 3.6 Hz, 4H); $^{13}$C NMR (400 MHz, CDCl$_3$): δ 139.2 (Ph), 128.6 (Ph), 128.1 (Ph), 126.7 (Ph), 59.5 (CH$_2$), 41.8 (CH).

Step 3. 5-Benzyl-hexahydro-pyrrolo[3,4-c]pyrrole-2-carboxylic acid tert-butyl ester:

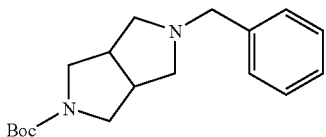

2,5-Dibenzyl-2,5-diazabicyclo[3.3.0]octane (3.8 g, 13.0 mmol) and 10% Pd(OH)$_2$/C (1.0 g) were dissolved in glacial acetic acid (50 mL) and stirred under an atmosphere of H$_2$ (1.0 atm) overnight. The catalyst was filtered off through Celite, and the filtrate was concentrated. The residue (acetate salt, 3.1 g, ~11.8 mmol) was dissolved in methanol-H$_2$O (100 mL, 3:1/v:v). The solution was adjusted to pH=10 with 3N aq NaOH, then di-tert-butyl dicarbonate (10.3 g, 47.3 mmol) was added at room temperature. After 30 minutes, additional 3N aq NaOH was added to bring pH back to pH=10, and the solution was allowed to stir 18 hours at room temperature. The mixture was concentrated and partitioned between dichloromethane and water. The aqueous layer was extracted with dichloromethane, and the combined organic layers was dried over MgSO$_4$ and concentrated. The crude product was purified by silica gel column chromatography (20% ethyl acetate in hexanes) to give a colorless oil (2.2 g, 35%). ESI MS m/z 303.1 (M+H$^+$).

Step 5. Hexahydro-pyrrolo[3,4-c]pyrrole-2-carboxylic acid tert-butyl ester:

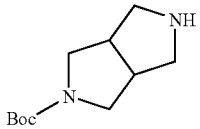

5-Benzyl-hexahydro-pyrrolo[3,4-c]pyrrole-2-carboxylic acid tert-butyl ester (2.2 g, 7.3 mmol) and 10% Pd(OH)$_2$/C (1.0 g) were dissolved in glacial acetic acid (30 mL) and stirred under an atmosphere of H$_2$ (1.0 atm) overnight. The catalyst was filtered off through Celite, and the filtrate was concentrated. The resulting light yellow glass (0.98 g, 49%) was used without further purification. $^1$H NMR (400 MHz, CD$_3$OD): δ 3.54-3.39 (m, 4H), 3.30-3.22 (m, 3H), 3.15-2.97 (m, 3H), 1.33 (s, 9H); $^{13}$C NMR (400 MHz, CD$_3$OD): δ 162.2 (C=O), 81.4, 50.8, 44.0, 42.3, 28.5 (t-Bu).

Step 6-8. 1-Cyclopropyl-7-fluoro-8-(hexahydro-pyrrolo [3,4-c]pyrrol-2-yl)-9-methyl-4-oxo-4H-quinolizine-3-carboxylic acid(trifluoroacetate salt):

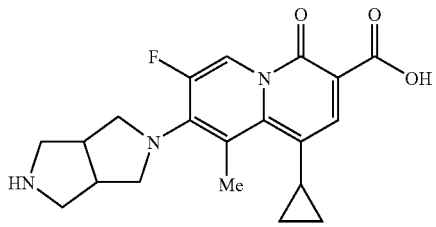

The title compound was prepared by using the same procedure as described in step 5-7 of example 4 except hexahydro-pyrrolo[3,4-c]pyrrole-2-carboxylic acid tert-butyl ester was used in place of 4-pyrrolidin-3-ylmethyl-piperazine-1-carboxylic acid tert-butyl ester. ESI MS m/z 372.2 (M+H$^+$); $^1$H NMR (400 MHz, CD$_3$OD): δ 9.40 (d, J=10.3 Hz, 1H), 8.43 (s, 1H), 3.86 (dd, J=10.3, 2.9 Hz, 2H), 3.66 (d, J=11.0, 2H), 3.64-3.55 (m, 2H), 3.20 (s, 2H), 3.06 (d, J=11.7 Hz, 2H), 2.81 (s, 3H, Me), 2.43-2.34 (m, 1H), 1.29-1.23 (m, 1H), 1.06 (app d, J=8.1 Hz, 1H), 0.90 (app t, J=9.5 Hz, 1H), 0.70 (app d, J=5.1, 1H).

Step 9. 3-[5-(3-Carboxy-1-cyclopropyl-7-fluoro-9-methyl-4-oxo-4H-quinolizin-8-yl)-hexahydro-pyrrolo[3,4-c] pyrrol-2-yl]-rifamycin S: The title compound was prepared by using the same procedure as described in step 8 of example 4 except 1-cyclopropyl-7-fluoro-8-(hexahydro-pyrrolo[3,4-c]pyrrol-2-yl)-9-methyl-4-oxo-4H-quinolizine-3-carboxylic acid (trifluoroacetate salt) was used in place of 1-cyclopropyl-7-fluoro-9-methyl-4-oxo-8-(3-piperazin-1-ylmethyl-pyrrolidin-1-yl)-4H-quinolizine-3-carboxylic acid (trifluoroacetate salt). ESI MS m/z 1065.3 (M+H$^+$).

EXAMPLE 16

3-[7-(3-Carboxy-1-cyclopropyl-7-fluoro-9-methyl-4-oxo-4H-quinolizin-8-yl)-2,7-diaza-spiro[4.4]non-2-yl]-rifamycin S

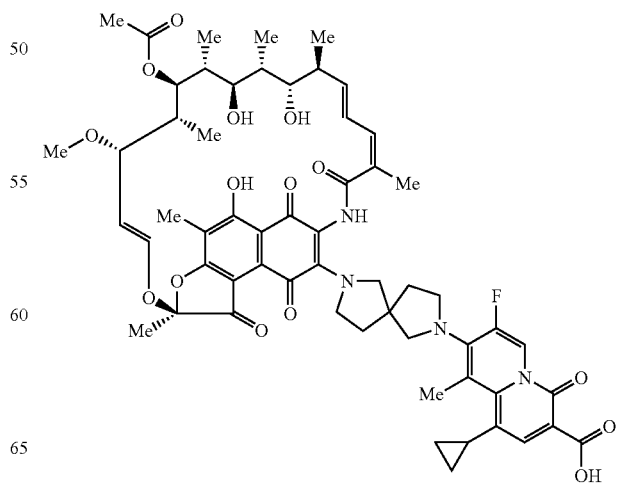

Step 1. 2,7-Diazaspiro[4.4]nonane (dihydrobromide):

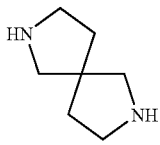

2,7-Dibenzyl-2,7-diazaspiro[4.4]nonane (This compound was prepared by following the procedures described in *J. Org. Chem.*, 1981, 46, 2757-2764; 1.8 g, 5.9 mmol) was dissolved in a solution of HBr in acetic acid (30%, 50 mL) and heated at 100° C. for 12 hours. The reaction was cooled and concentrated to dryness in vacuo to give the debenzylated product (1.4 g, 82% based on di-HBr salt) as a light brown solid. $^1$H NMR (400 MHz, CD$_3$OD): δ 3.51-3.44 (m, 8H), 2.30-2.12 (m, 4H); $^{13}$C NMR (400 MHz, CDCl$_3$): δ 53.7 (CH$_2$), 49.9 (C), 46.3 (CH$_2$), 35.6 (CH$_2$).

Step 2. 3-[7-(3-Carboxy-1-cyclopropyl-7-fluoro-9-methyl-4-oxo-4H-quinolizin-8-yl)-2,7-diaza-spiro[4.4]non-2-yl]-rifamycin S: The title compound was prepared by using the same procedure as described in step 3-5 of example 8 except 2, 7-diazaspiro[4.4]nonane (dihydrobromide) was used in place of piperidine-4-carboxylic acid (pyrrolidin-3-ylmethyl)-amide (trifluoroacetate salt). ESI MS m/z 1079.3 (M+H$^+$).

EXAMPLE 17

(R/S,R/S)-3-{3-[1-(3-Carboxy-1-cyclopropyl-7-fluoro-9-methyl-4-oxo-4H-quinolizine-8-yl)-piperidin-3-yl]-pyrrolidin-1-yl}-rifamycin S

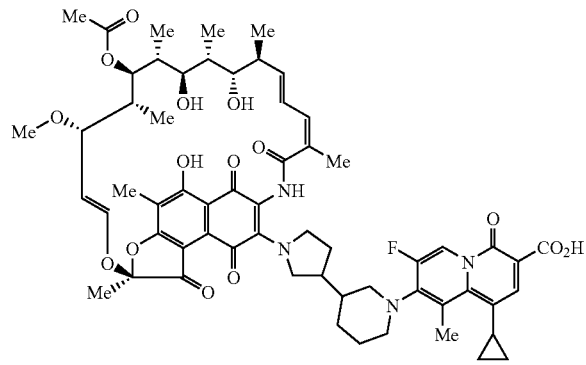

Step 1. (R/S)-3-Pyridin-3-yl-pyrrolidine-1-carboxylic acid tert-butyl ester:

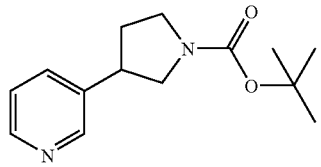

3-Pyrrolidine-3-yl pyridine (1.00 g, 6.74 mmol) was taken up in water (10 mL) and ethanol (10 mL). To this solution was added di-tert-butyl dicarbonate (3.21 g, 20.24 mmol) and then 1N aq NaOH (6 mL) to pH=10. The reaction solution was stirred for 24 hours and evaporated to dryness. The product (1.67 g, 100%) was used without further purification. ESI MS m/z 249.0 (M+H$^+$).

Step 2. (R/S,R/S)-3-Piperidin-3-yl-pyrrolidine-1-carboxylic acid tert-butyl ester:

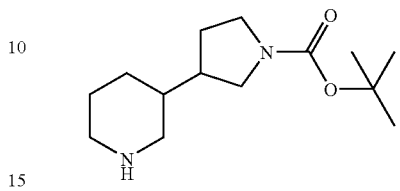

The product from step 1 (1.67 g, 6.73 mmol) was dissolved in acetic acid (1.7 mL) and methanol (17 mL). To the solution was added platinum (IV) oxide (152 mgs, 0.67 mmol) and the formed suspension was hydrogenated at 50 psi for 60 hours. The reaction mixture was filtered over Celite and washed with methanol. The filtrate was evaporated under reduced pressure, partitioned between 1N aq NaOH (20 mL) and ethyl acetate. The aqueous phase was extracted again with ethyl acetate. The combined organic phase was dried over Na$_2$SO$_4$, and evaporated to give the product (~1.0 g, 60%), which was used without further purification. ESI MS m/z 254.9 (M+H$^+$).

Step 3. (R/S,R/S)-3-{3-[1-(3-Carboxy-1-cyclopropyl-7-fluoro-9-methyl-4-oxo-4H-quinolizine-8-yl)-piperidin-3-yl]-pyrrolidin-1-yl}-rifamycin S: The title compound was prepared by using the same procedure as described in step 5-8 of example 4 except (R/S,R/S)-3-piperidin-3-yl-pyrrolidine-1-carboxylic acid tert-butyl ester was used in place of (R/S)-4-pyrrolidin-3-ylmethyl-piperazine-1-carboxylic acid tert-butyl ester. ESI MS m/z 1075.6 (M-MeOH+H$^+$); $^1$H NMR (400 MHz, CDCl$_3$) δ 9.25 (m, 1H), 8.28 (s, 1H), 7.65 (m, 1H), 7.50 (m, 1H), 6.82 (m, 1H), 6.30-6.01 (m, 2H), 5.50 (m, 2H), 5.02 (m, 2H), 4.15-3.05 (m, 8H), 3.02 (m, 6H), 2.72 (m, 3H), 2.60-2.08 (m, 8H), 2.07-1.80 (m, 5H), 1.75-1.40 (m, 4H), 1.34 (s, 3H), 1.34-1.10 (m, 6H), 1.18 (s, 3H), 0.97 (m, 4H), 0.78 (m, 4H), 0.62 (m, 4H), 0.04 (m, 3H).

EXAMPLE 18

(R/S)-3-{3-[4-(3-Carboxy-1-cyclopropyl-7-fluoro-9-methyl-4-oxo-4H-quinolizin-8-yl)-piperazin-1-yl]-pyrrolidin-1-yl}-rifamycin S

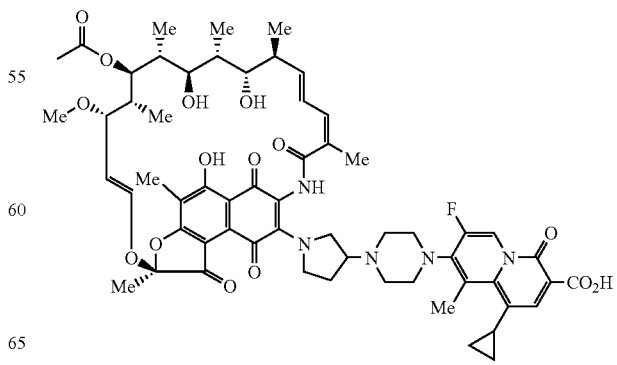

Step 1: (R/S)-8-[4-(1-tert-Butoxycarbonyl-pyrrolidin-3-yl)-piperazin-1-yl]-1-cyclopropyl-7-fluoro-9-methyl-4-oxo-4H-quinolizine-3-carboxylic acid:

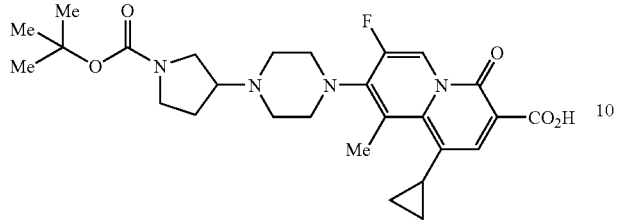

The title compound was prepared as described in Step 1 of Example 9 (1974) except 3-oxo-pyrrolidine-1-carboxylic acid tert-butyl ester was used in place of 4-oxo-piperidine-1-carboxylic acid tert-butyl ester and 1-cyclopropyl-7-fluoro-9-methyl-4-oxo-8-piperazin-1-yl-4H-quinolizine-3-carboxylic acid was used in place of (8-(3-aminomethyl-pyrrolidin-1-yl)-1-cyclopropyl-7-fluoro-9-methyl-4-oxo-4H-quinolizine-3-carboxylic acid.

Step 2-3: (R/S)-3-{3-[4-(3-Carboxy-1-cyclopropyl-7-fluoro-9-methyl-4-oxo-4H-quinolizin-8-yl)-piperazin-1-yl]-pyrrolidin-1-yl}-rifamycin S: The title compound was prepared as described in step 7-8 in example 4 except the product from step 1 was used in place of (R/S)-8-[3-(4-tert-butoxycarbonyl-piperazin-1-ylmethyl)-pyrrolidin-1-yl]-1-cyclopropyl-7-fluoro-9-methyl-4-oxo-4H-quinolizine-3-carboxylic acid. ESI MS m/z 1109.2 (M+H$^+$); $^1$H NMR (400 MHz, CDCl$_3$) δ (~1:1 mixture of two diastereomers) 13.86-13.83 (m, 1H), 9.19 (d, J=9.5 Hz, 1H), 8.36 (s, 1H), 7.55 (two singlets, 1H), 6.92-6.80 (m, 1H), 6.36-6.00 (m, 3H), 5.20-5.00 (m, 2H), 4.08-3.52 (m, 8H), 3.44 (s, 3H), 3.08 (s, 3H), 3.07-3.00 (m, 3H), 2.77 (s, 3H), 2.76-2.60 (m, 3H), 2.40-2.32 (m, 1H), 2.25 (s, 3H), 2.06 (s, 3H), 1.80-1.70 (overlap with Me, m, 2H), 1.71 (s, 3H), 1.55 (s, 9H), 1.24-0.04 (m, 16H).

EXAMPLE 19

(R/S, R/S)-3-{3-[1-(3-Carboxy-1-cyclopropyl-7-fluoro-9-methyl-4-oxo-4H-quinolizine-8-yl)-piperidin-3-ylamino]-pyrrolidin-1-yl}-rifamycin S

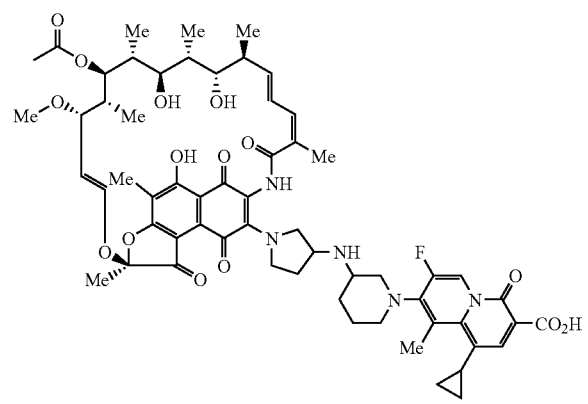

Synthesis: Step 1. (R/S)-8-(3-Amino-piperidin-1-yl)-1-cyclopropyl-7-fluoro-9-methyl-4-oxo-4H-quinolizine-3-carboxylic acid:

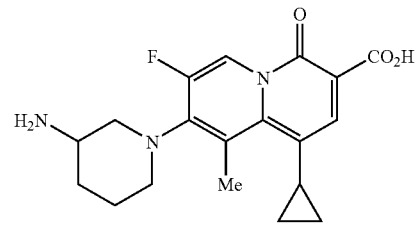

The title compound was prepared as described step 1-3 of example 1 except 3-amino-piperidine-1-carboxylic acid tert-butyl ester was used in place of 3-aminomethyl-pyrrolidine-1-carboxylic acid tert-butyl ester. ESI MS m/z 360.3 (M+H$^+$); $^1$H NMR (400 MHz, CD$_3$OD) δ 9.26 (d, J=8.6 Hz, 1H), 8.22 (s, 1H), 3.81 (d, J=11.9 Hz, 1H), 3.55-3.49 (m, 2H), 3.43-3.33 (m, 2H), 2.87 (s, 1H), 2.45-2.35 (m, 1H), 2.30-2.21(m, 1H), 2.04-1.95 (m, 1H), 1.92-1.82 (m, 1H), 1.77-1.65 (m, 1H), 1.12-1.05 (m, 1H), 0.73-0.67 (m, 1H).

Step 2. (R/S, R/S)-3-{3-[1-(3-Carboxy-1-cyclopropyl-7-fluoro-9-methyl-4-oxo-4H-quinolizine-8-yl)-piperidin-3-ylamino]-pyrrolidin-1-yl}-rifamycin S: The title compound was prepared as described for Example 18 except (R/S)-8-(3-amino-piperidin-1-yl)-1-cyclopropyl-7-fluoro-9-methyl-4-oxo-4H-quinolizine-3-carboxylic acid was used in place of 1-cyclopropyl-7-fluoro-9-methyl-4-oxo-8-piperazin-1-yl-4H-quinolizine-3-carboxylic acid. ESI MS m/z 1123.3 (M+H$^+$); $^1$H NMR (400 MHz, CDCl$_3$) δ (mixture of four diastereomers) 13.90-13.70 (m, 1H), 9.20-9.12 (m, 1H), 8.32-8.24 (m, 1H), 7.72-7.52 (m, 2H), 7.08-6.80 (m, 2H), 6.32-6.00 (m, 2H), 5.16-4.98 (m, 1H), 4.20-2.70 (m, 16H), 2.40-1.50 (m, 28H), 1.47-0.01 (m, 18H).

EXAMPLE 20

(S)-3-(4-{[1-(3-Carboxy-1-cyclopropyl-7-fluoro-9-methyl-4-oxo-4H-quinolizin-8-yl)-pyrrolidin-3-ylamino]-methyl}-piperidin-1-yl)-rifamycin S

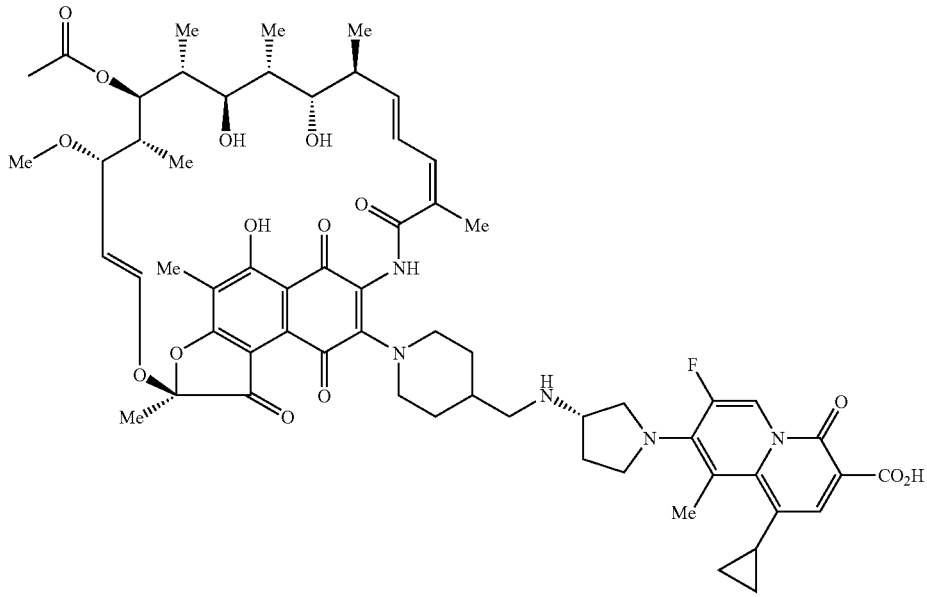

Synthesis: The title compound was prepared as described in Example 18 except (S)-8-(3-amino-pyrrolidin-1-yl)-1-cyclopropyl-7-fluoro-9-methyl-4-oxo-4H-quinolizine-3-carboxylic acid was used in place of 1-cyclopropyl-7-fluoro-9-methyl-4-oxo-8-piperazin-1-yl-4H-quinolizine-3-carboxylic acid and 4-formyl-piperidine-1-carboxylic acid tert-butyl ester was used in place of 3-oxo-pyrrolidine-1-carboxylic acid tert-butyl ester. ESI MS m/z 1137.3 (M+H$^+$); $^1$H NMR (400 MHz, CDCl$_3$) δ 13.33 (br s, 1H), 9.04 (d, J=11.1 Hz, 1H), 8.20 (s, 1H), 7.50 (s, 1H), 7.10-6.90 (m, 1H), 6.30 (d, J=11.1 Hz, 1H), 6.11 (dd, J=15.7, 5.5 Hz, 1H), 6.04 (d, J=9.4 Hz, 1H), 5.08 (d, J=12.6 Hz, 1H), 5.06 (d, J=11.8 Hz, 1H), 4.00-3.80 (m, 5H), 3.76-3.68 (m, 1H), 3.52-3.36 (m, 1H), 3.32-3.21 (m, 1H), 3.07 (s, 3H), 3.04-2.94 (m, 2H), 2.59 (s, 3H), 2.56-2.51 (m, 2H), 2.36-2.28 (m, 1H), 2.23 (s, 3H), 2.20-2.12 (m, 1H), 2.08 (s, 3H), 2.05 (s, 3H), 1.92-1.84 (m, 1H), 1.80-1.73 (m, 4H), 1.70 (s, 3H), 1.68-1.61 (m, 2H), 1.32-1.20 (m, 2H), 1.01 (d, J=7.1 Hz, 3H), 1.00-0.93 (m, 2H), 0.84 (d, J=7.0 Hz, 3H), 0.67 (d, J=7.2 Hz, 3H), 0.64 (m, 2H), 0.14 (d, J=7.1 Hz, 3H).

EXAMPLE 21

(R,S)-3-{3-[1-(3-Carboxy-1-cyclopropyl-7-fluoro-9-methyl-4-oxo-4H-quinolizin-8-yl)-pyrrolidin-3-ylamino]-pyrrolidin-1-yl}-rifamycin S and (S,S)-3-{3-[1-(3-Carboxy-1-cyclopropyl-7-fluoro-9-methyl-4-oxo-4H-quinolizin-8-yl)-pyrrolidin-3-ylamino]-pyrrolidin-1-yl}-rifamycin S

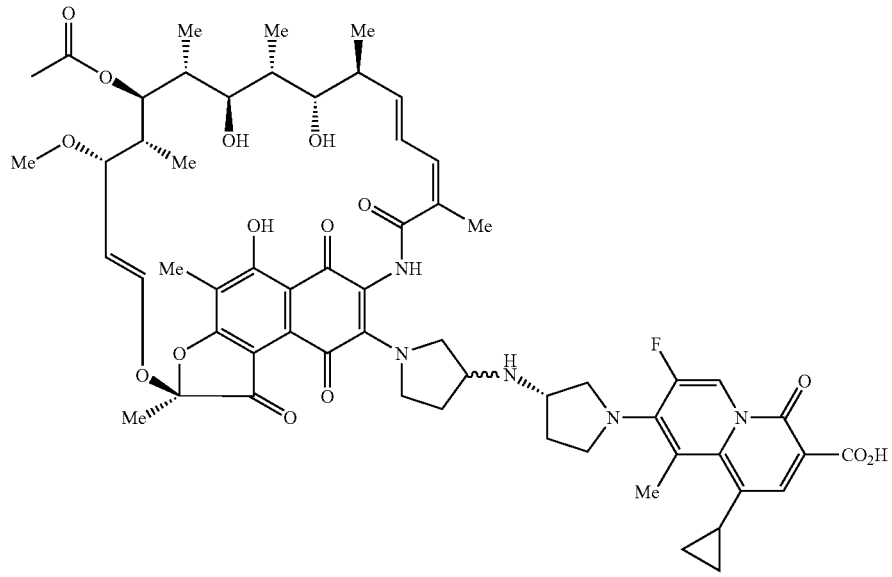

The title compounds were prepared as described in Example 18 except (S)-8-(3-amino-pyrrolidin-1-yl)-1-cyclopropyl-7-fluoro-9-methyl-4-oxo-4H-quinolizine-3-carboxylic acid was used in place of 1-cyclopropyl-7-fluoro-9-methyl-4-oxo-8-piperazin-1-yl-4H-quinolizine-3-carboxylic acid. Two diastereomers were separated by preparative thin layer chromatography. Stereochemistry is not defined. ESI MS m/z 1109.2 (M+H$^+$); $^1$H NMR (400 MHz, CDCl$_3$) δ (diastereomer 1) 13.69 (s, 1H), 8.91 (d, J=10.0 Hz, 1H), 8.05 (s, 1H), 7.48 (s, 1H), 6.84-6.72 (m, 1H), 6.19 (d, J=10.2 Hz, 1H), 6.04-5.95 (m, 2H), 5.08-5.00 (m, 1H), 4.94 (d, J=10.4 Hz, 1H), 4.00-3.32 (m, 15H), 2.99 (s, 3H), 2.96-2.89 (m, 1H), 2.51 (s, 3H), 2.28-2.20 (br s, 1H), 2.14 (s, 3H), 2.12-2.02 (m, 3H), 1.98 (s, 3H), 1.96 (s, 3H), 1.84-1.76 (m, 2H), 1.72-1.64 (m, 5H), 1.61 (s, 3H), 0.96-0.86 (m, 5H), 0.74 (d, J=7.1 Hz, 3H), 0.60-0.52 (m, 4H), 0.04-0.00 (m, 3H); (diastereomer 2) 13.90-13.66 (s, 1H), 8.99 (d, J=9.9 Hz, 1H), 8.15 (s, 1H), 7.67 (s, 1H), 6.96-6.84 (m, 1H), 6.27 (d, J=11.0 Hz, 1H), 6.16-6.04 (m, 2H), 5.20-5.08 (m, 1H), 5.01 (d, J=10.2 Hz, 1H), 4.00-3.32 (m, 15H), 2.99 (s, 3H), 2.96-2.89 (m, 1H), 2.51 (s, 3H), 2.28-2.20 (br s, 1H), 2.14 (s, 3H), 2.12-2.02 (m, 3H), 1.98 (s, 3H), 1.96 (s, 3H), 1.84-1.76 (m, 2H), 1.72-1.64 (m, 5H), 1.61 (s, 3H), 0.96-0.86 (m, 5H), 0.74 (d, J=7.1 Hz, 3H), 0.60-0.52 (m, 4H), 0.04-0.00 (m, 3H).

EXAMPLE 22

(R/S)-3-{4-[1-(3-Carboxy-1-cyclopropyl-7-fluoro-9-methyl-4-oxo-4H-quinolizin-8-yl)-pyrrolidin-3-yl]-piperazin-1-yl}-rifamycin S

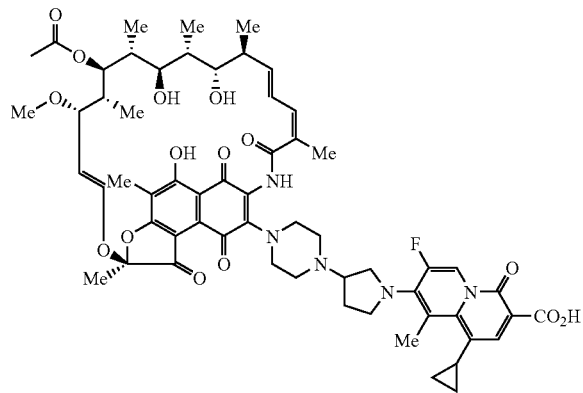

Synthesis: Step 1. (R/S)-4-(1-tert-Butoxycarbonyl-pyrrolidin-3-yl)-piperazine-1-carboxylic acid benzyl ester:

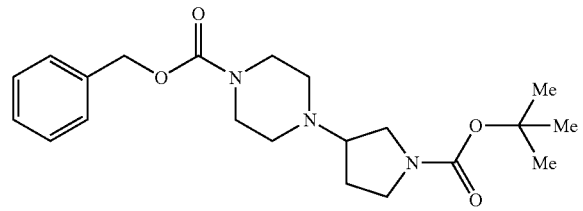

The titled compound was prepared as described for Step 1 of Example 9 (1974) except piperazine-1-carboxylic acid benzyl ester and 3-oxo-pyrrolidine-1-carboxylic acid tert-butyl ester were used in place of 4-oxo-piperidine-1-carboxylic acid tert-butyl ester and (8-(3-aminomethyl-pyrrolidin-1-yl)-1-cyclopropyl-7-fluoro-9-methyl-4-oxo-4H-quinolizine-3-carboxylic acid. ESI MS m/z 390.2 (M+H$^+$).

Step 2: (R/S)-8-[3-(4-Benzyloxycarbonyl-piperazin-1-yl)-pyrrolidin-1-yl]-1-cyclopropyl-7-fluoro-9-methyl-4-oxo-4H-quinolizine-3-carboxylic acid:

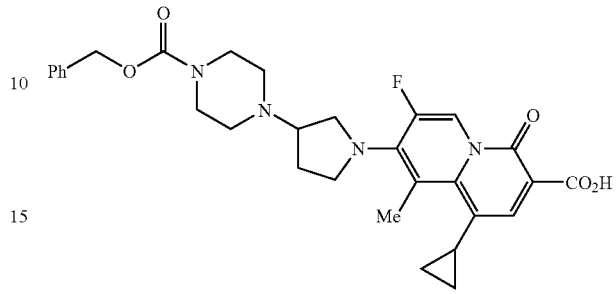

The title compound was prepared by using the same procedure as described in step 2-3 in example 8 except (R/S)-4-(1-tert-butoxycarbonyl-pyrrolidin-3-yl)-piperazine-1-carboxylic acid benzyl ester was used in place of (R/S)-4-[(1-tert-butoxycarbonyl-pyrrolidin-3-ylmethyl)-carbamoyl]-piperidine-1-carboxylic acid tert-butyl ester.

Step 3. (R/S)-1-Cyclopropyl-7-fluoro-9-methyl-4-oxo-8-(3-piperazin-1-yl-pyrrolidin-1-yl)-4H-quinolizine-3-carboxylic acid:

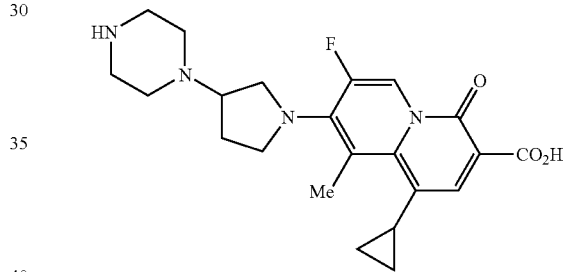

The product from step 2 (168 mg, 0.31 mmol) was dissolved in ethyl alcohol (1.5 mL). To this solution was added 10% Pd/C (100 mg). Heterogeneous solution was hydrogenated at 1 atm for two hours. Reaction mixture was then filtered through Celite and eluted with ethyl alcohol. Filtrate was concentrated in vacuo to give a pale yellow solid (125 mg, 100%).

Step 4: (R/S)-3-{4-[1-(3-Carboxy-1-cyclopropyl-7-fluoro-9-methyl-4-oxo-4H-quinolizin-8-yl)-pyrrolidin-3-yl]-piperazin-1-yl}-rifamycin S: The title compound was prepared by using the same procedure as described in step 8 of example 4 except (R/S)-1-cyclopropyl-7-fluoro-9-methyl-4-oxo-8-(3-piperazin-1-yl-pyrrolidin-1-yl)-4H-quinolizine-3-carboxylic acid was used in place of (R/S)-1-cyclopropyl-7-fluoro-9-methyl-4-oxo-8-(3-piperazin-1-ylmethyl-pyrrolidin-1-yl)-4H-quinolizine-3-carboxylic acid. ESI MS m/z 1109.2 (M+H$^+$); $^1$H NMR (400 MHz, CDCl$_3$) δ (~1:1 mixture of two diastereomers) 13.85 (two singlets, 1H), 13.22 (s, 1H), 9.06 (two doublets, J=5.09 Hz, 1H), 8.22 (two singlets, 1H), 7.50 (s, 1H), 7.24-7.14 (m, 1H), 6.34 (d, J=10.9 Hz, 1H), 6.13 (dd, J=15.7, 6.3 Hz, 1H), 6.04 (d, J=12.7 Hz, 1H), 5.14-5.08 (m, 1H), 4.02-3.32 (m, 13H), 3.08 (s, 3H), 3.05-2.95 (m, 2H), 2.88-2.64 (m, 3H), 2.59 (s, 3H), 2.58-2.54 (m, 1H), 2.36-2.28 (m, 1H), 2.25 (s, 3H), 2.20-2.12 (m, 1H), 2.11 (s, 3H), 2.06 (s, 3H), 2.00-1.75 (m, 3H), 1.72 (two singlets, 3H), 1.68-1.64 (m, 2H), 1.09-1.04 (m, 1H), 1.01 (d, J=7.0 Hz, 3H), 0.92-0.87 (m, 1H), 0.86 (d, J=6.3 Hz, 3H), 0.69 (d, J=7.0 Hz, 3H), 0.65-0.55 (m, 2H), 0.17 (d, J=7.0 Hz, 3H).

EXAMPLE 23

(R/S, S)-3-{3-[1-(3-Carboxy-1-cyclopropyl-7-fluoro-9-methyl-4-oxo-4H-quinolizin-8-yl)-pyrrolidin-3-ylamino]-piperidin-1-yl}-rifamycin S:

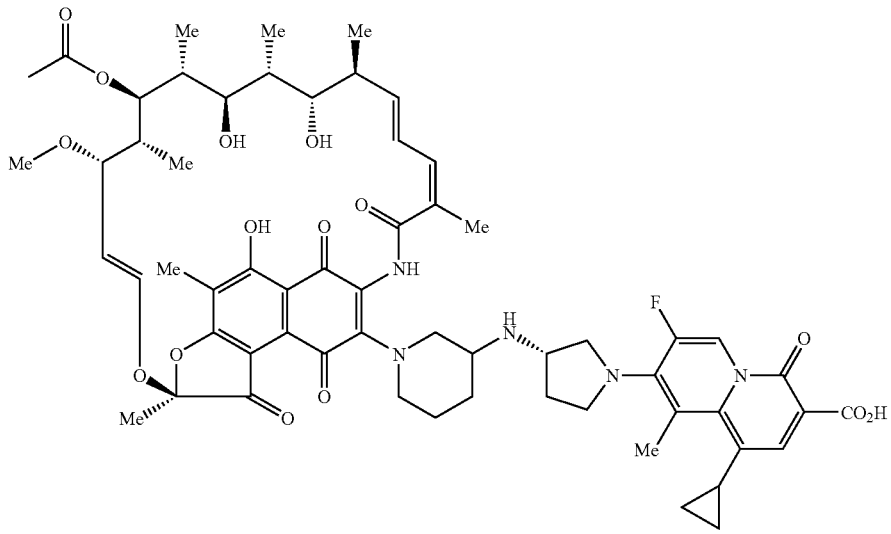

Synthesis: The title compound was prepared as described in Example 18 except (S)-8-(3-amino-pyrrolidin-1-yl)-1-cyclopropyl-7-fluoro-9-methyl-4-oxo-4H-quinolizine-3-carboxylic acid was used in place of 1-cyclopropyl-7-fluoro-9-methyl-4-oxo-8-piperazin-1-yl-4H-quinolizine-3-carboxylic acid and 3-oxo-piperidine-1-carboxylic acid tert-butyl ester was used in place of 3-oxo-pyrrolidine-1-carboxylic acid tert-butyl ester. ESI MS m/z 1123.3 (M+H$^+$); $^1$H NMR (400 MHz, CDCl$_3$) δ (~1:1 mixture of two diastereomers) 13.88 (br s, 1H), 13.20 (br s, 1H), 9.04-8.96 (m, 1H), 8.16 (two singlets, 1H), 7.54 (two singlets, 1H), 7.12-7.00 (m, 1H), 6.33 (app d, J=10.7 Hz, 1H), 6.18-6.08 (m, 1H), 6.06-5.98 (m, 1H), 5.10-4.94 (m, 2H), 4.00-3.00 (overlap with Me, m, 15H), 3.06 (two singlets, 3H), 2.74 (brs, 1H), 2.60 (two singlets, 3H), 2.36-1.52 (overlap with 4 Me, m, 11H), 2.23 (two singlets, 3H), 2.09 (brs, 3H), 2.06 (two singlets, 3H), 1.70 (two singlets, 3H), 1.01 (app d, J=7.0 Hz, 3H), 0.98-0.93 (m, 2H), 0.85 (app d, J=7.0 Hz, 3H), 0.69 (app d, J=7.0 Hz, 3H), 0.64-0.61 (m, 1H), 0.15 (app d, J=6.3 Hz, 3H).

EXAMPLE 24

(R)-3-(4-{[1-(3-Carboxy-1-cyclopropyl-7-fluoro-9-methyl-4-oxo-4H-quinolizine-8-yl)-pyrrolidin-3-ylmethyl]-amino}-piperidin-1-yl)-rifamycin S

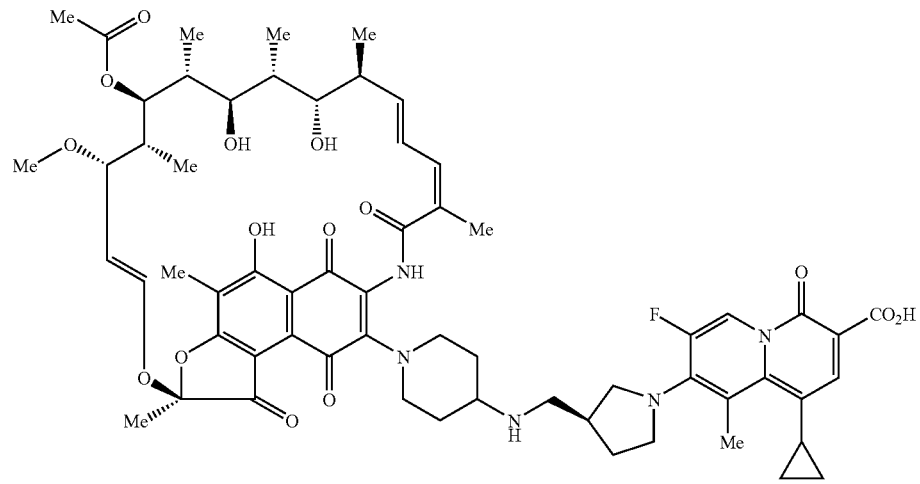

Synthesis: Step 1: 3-(4-oxopiperidin-1-yl)-rifamycin S:

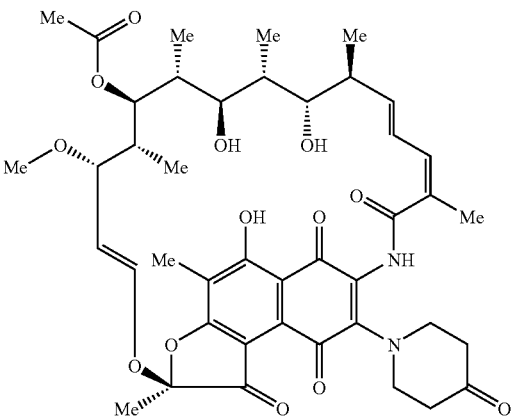

The solution of 4-piperidone monohydrate hydrochloride (757 mg, 4.92 mmol) in water (1.0 mL) and THF (8.0 mL) was added 3-bromorifamycin S (1.26 g, 1.63 mmol). The solution was stirred at room temperature for five hours. The reaction mixture was then partitioned between ethyl acetate and water. The separated organic layer was washed with brine, dried over sodium sulfate and concentrated in vacuo. The residue was purified by chromatography on silica gel (with 5% methanol in dichloromethane) to give the title compound as a dark brown solid (900 mg, 70%). ESI MS m/z 793.1 (M+H$^+$).

Step 2: (R)-3-(4-{[1-(3-Carboxy-1-cyclopropyl-7-fluoro-9-methyl-4-oxo-4H-quinolizine-8-yl)-pyrrolidin-3-ylmethyl]-amino}-piperidin-1-yl)-rifamycin S: To the solution of 3-(4-oxopiperidin-1-yl)-rifamycin S (101 mg, 0.13 mmol) and (R)-8-(3-aminomethyl-cyclopentyl)-1-cyclopropyl-7-fluoro-9-methyl-4-oxo-4H-quinolizine-3-carboxylic acid (trifluoroacetate salt, 73 mg, 0.15 mmol) in DMF (3.0 mL) was added acetic acid (40 μL, 0.64 mmol) followed by NaBH(OAc)$_3$ (124 mg, 0.58 mmol). The solution was heated at 40° C. for 1.5 hour. Then the reaction mixture was stirred with dichloromethane (10 mL) and 5% K$_3$Fe(CN)$_6$ phosphate buffer (0.2 N, PH=7.4, 10 mL) for one hour at room temperature. The separated organic layer was washed with water followed by brine, dried over sodium sulfate and concentrated in vacuo. The residue was purified by preparative thin layer chromatography (10% methanol in dichloromethane) to give the title compound as a dark brown solid (105 mg, 71%). ESI MS m/z 1136.6 (M+H$^+$). $^1$H NMR (400 MHz, CDCl$_3$) δ 9.00 (d, J=10.0 Hz, 1H), 8.07 (s, 1H), 7.57 (s, 1H), 7.12-7.02 (m, 1H), 6.35 (d, J=10.8 Hz, 1H), 6.17 (dd, J=6.0, 15.2 Hz, 1H), 6.06 (d, J=12.0 Hz, 1H), 5.10 (dd, J=2.4, 8.0 Hz, 1H), 5.07 (d, J=5.2 Hz, 1H), 3.97-3.91 (m, 3H), 3.88-3.75 (m, 5H), 3.65-3.57 (m, 2H), 3.47 (br s, 1H), 3.41-3.28 (m, 3H), 3.10 (s, 3H), 3.06-2.94 (m, 8H), 2.76-2.60 (m, 1H), 2.60 (s, 3H), 2.39-2.25 (m, 2H), 2.26 (s, 3H), 2.11 (s, 3H), 2.10-1.98 (overlap with Me, m, 12H), 2.09 (s, 3H), 1.85-1.79 (m, 3H), 1.74 (s, 3H), 1.72-1.58 (m, 2H), 1.04 (d, J=6.8 Hz, 3H), 1.00-0.89 (m, 2H), 0.88 (d, J=7.2 Hz, 3H), 0.78-0.73 (m, 1H), 0.71 (d, J=7.2 Hz, 3H), 0.66-0.61 (m, 1H), 0.17 (d, J=6.4 Hz, 3H).

EXAMPLE 25

(R/S)-3-(4-{[1-(3-Carboxy-1-cyclopropyl-7-fluoro-9-methyl-4-oxo-4H-quinolizine-8-yl)-pyrrolidin-3-ylmethyl]-amino}-piperidin-1-yl)-rifamycin S

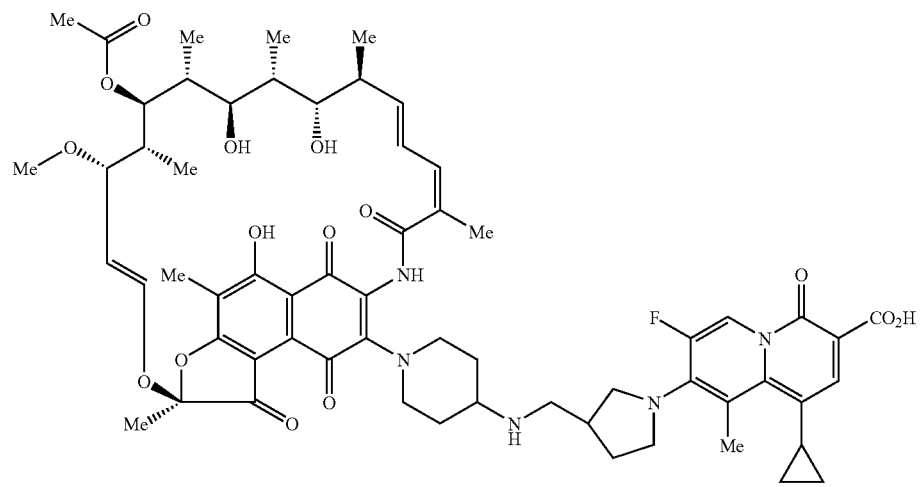

Synthesis: The title compound was prepared by using the same procedure as described for Example 21 except (R/S)-3-aminomethyl-pyrrolidine-1-carboxylic acid tert-butyl ester was used in place of (R)-3-aminomethyl-pyrrolidine-1-carboxylic acid tert-butyl ester ESI MS m/z 1136.6 (M+H$^+$). $^1$H NMR (400 MHz, CDCl$_3$) δ 9.00 (d, J=10.0 Hz, 1H), 8.07 (s, 1H), 7.57 (s, 1H), 7.12-7.02 (m, 1H), 6.35 (d, J=10.8 Hz, 1H), 6.17 (dd, J=6.0, 15.2 Hz, 1H), 6.06 (d, J=12.0 Hz, 1H), 5.10 (dd, J=2.4, 8.0 Hz, 1H), 5.07 (d, J=5.2 Hz, 1H), 3.97-3.91 (m, 3H), 3.88-3.75 (m, 5H), 3.65-3.57 (m, 2H), 3.47 (br s, 1H), 3.41-3.28 (m, 3H), 3.10 (s, 3H), 3.06-2.94 (m, 8H), 2.76-2.60 (m, 1H), 2.60 (s, 3H), 2.39-2.25 (m, 2H), 2.26 (s, 3H), 2.11 (s, 3H), 2.09 (s, 3H), 2.10-1.98 (m, 12H), 1.85-1.79 (m, 3H), 1.74 (s, 3H), 1.72-1.58 (m, 2H), 1.04 (d, J=6.8 Hz, 3H), 1.00-0.89 (m, 2H), 0.88 (d, J=7.2 Hz, 3H), 0.78-0.73 (m, 1H), 0.71 (d, J=7.2 Hz, 3H), 0.66-0.61 (m, 1H), 0.17 (d, J=6.4 Hz, 3H).

EXAMPLE 26

(S)-3-(4-{[1-(3-Carboxy-1-cyclopropyl-7-fluoro-9-methyl-4-oxo-4H-quinolizine-8-yl)-pyrrolidin-3-ylmethyl]-amino}-piperidin-1-yl)-rifamycin S

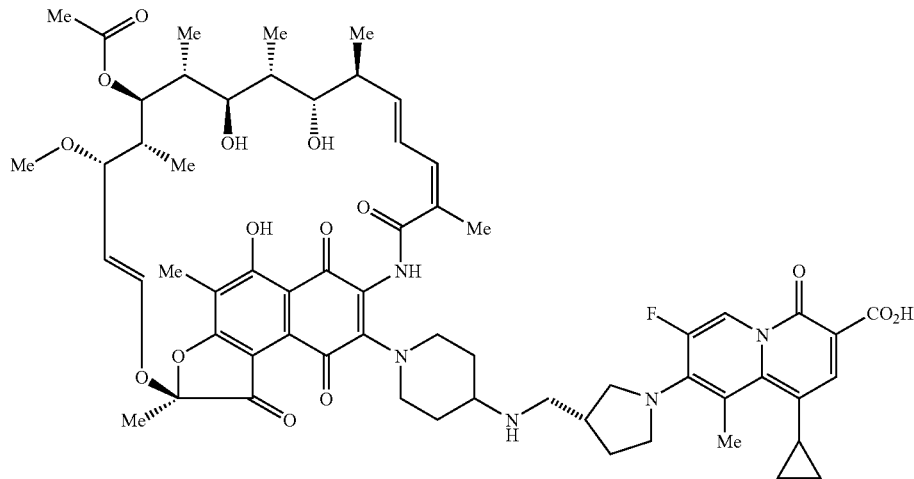

Synthesis: The title compound was prepared by using the same procedure as described for Example 21 except (S)-3-aminomethyl-pyrrolidine-1-carboxylic acid tert-butyl ester was used in place of (R)-3-aminomethyl-pyrrolidine-1-carboxylic acid tert-butyl ester. ESI MS m/z 1136.6 (M+H$^+$). $^1$H NMR (400 MHz, CDCl$_3$) δ 9.00 (d, J=10.0 Hz, 1H), 8.07 (s, 1H), 7.57 (s, 1H), 7.12-7.02 (m, 1H), 6.35 (d, J=10.8 Hz, 1H), 6.17 (dd, J=6.0, 15.2 Hz, 1H), 6.06 (d, J=12.0 Hz, 1H), 5.10 (dd, J=2.4, 8.0 Hz, 1H), 5.07 (d, J=5.2 Hz, 1H), 3.97-3.91 (m, 3H), 3.88-3.75 (m, 5H), 3.65-3.57 (m, 2H), 3.47 (br s, 1H), 3.41-3.28 (m, 3H), 3.10 (s, 3H), 3.06-2.94 (m, 8H), 2.76-2.60 (m, 1H), 2.60 (s, 3H), 2.39-2.25 (m, 2H), 2.26 (s, 3H), 2.11 (s, 3H), 2.09 (s, 3H), 2.10-1.98 (m, 12H), 1.85-1.79 (m, 3H), 1.74 (s, 3H), 1.72-1.58 (m, 2H), 1.04 (d, J=6.8 Hz, 3H), 1.00-0.89 (m, 2H), 0.88 (d, J=7.2 Hz, 3H), 0.78-0.73 (m, 1H), 0.71 (d, J=7.2 Hz, 3H), 0.66-0.61 (m, 1H), 0.17 (d, J=6.4 Hz, 3H).

EXAMPLE 27

(S)-3-{4-[1-(3-Carboxy-1-cyclopropyl-7-fluoro-9-methyl-4-oxo-4H-quinolizine-8-yl)-pyrrolidin-3-ylamino]-piperidin-1-yl}-rifamycin S

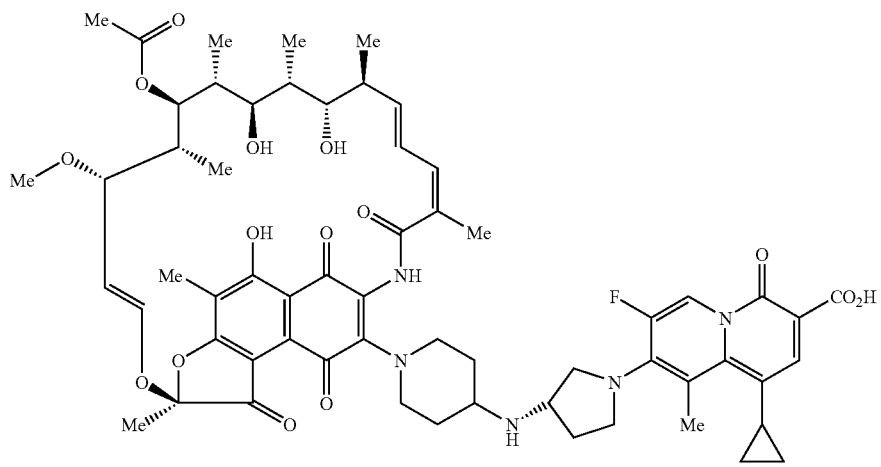

Step 1-3. (S)-8-(3-Amino-pyrrolidin-1-yl)-1-cyclopropyl-7-fluoro-9-methyl-4-oxo-4H-quinolizine-3-carboxylic acid (trifluoroacetate salt):

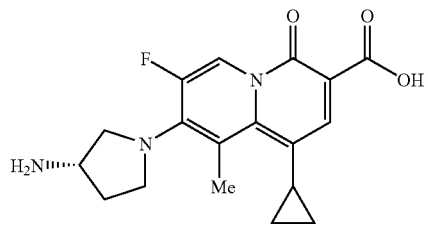

The title compound was prepared by using the same procedure as described in Step 5-7 of Example 1 except (S)-pyrrolidin-3-yl-carbamic acid tert-butyl ester was used in place of (R/S)-4-pyrrolidin-3-ylmethyl-piperazine-1-carboxylic acid tert-butyl ester. ESI MS m/z 346.1 (M+H⁺).

Step 4. (S)-3-{4-[1-(3-Carboxy-1-cyclopropyl-7-fluoro-9-methyl-4-oxo-4H-quinolizine-8-yl)-pyrrolidin-3-ylamino]-piperidin-1-yl}-rifamycin S: The title compound was prepared by using the same procedure as described for example 24 except (S)-8-(3-amino-pyrrolidin-1-yl)-1-cyclopropyl-7-fluoro-9-methyl-4-oxo-4H-quinolizine-3-carboxylic acid (trifluoroacetate salt) was used in place of (R)-8-(3-aminomethyl-pyrrolidin-1-yl)-1-cyclopropyl-7-fluoro-9-methyl-4-oxo-4H-quinolizine-3-carboxylic acid (trifluoroacetate salt). ESI MS m/z 1122.5 (M+H⁺). ¹H NMR (400 MHz, CDCl₃) δ 13.90 (br s, 1H), 13.28 (s, 1H), 9.05 (d, J=9.6 Hz, 1H), 8.20 (s, 1H), 7.58 (s, 1H), 7.09-7.00 (m, 1H), 6.78-6.72 (m, 1H), 6.36 (d, J=10.8 Hz, 1H), 6.18 (dd, J=6.0, 15.6 Hz, 1H), 6.07 (d, J=12.4 Hz, 1H), 5.10-5.04 (m, 2H), 4.00-3.28 (m, ~15H), 3.10 (s, 3H), 3.08-3.01 (m, 2H), 2.68-2.62 (overlap with Me, m, 1H), 2.64 (s, 3H), 2.38-2.28 (overlap with Me, m, 2H), 2.27 (s, 3H), 2.18-2.08 (overlap with 2 Me, m, 1H), 2.12 (s, 3H), 2.09 (s, 3H), 1.85-1.48 (m, 4H), 1.74 (s, 3H), 1.28-1.20 (m, 1H), 1.04 (d, J=6.8 Hz, 3H), 1.05-0.92 (m, 2H), 0.88 (d, J=7.2 Hz, 3H), 0.71 (d, J=6.4 Hz, 3H), 0.68-0.66 (m, 2H), 0.17 (d, J=6.4 Hz, 3H).

EXAMPLE 28

(R/S)-3-{4-[1-(3-Carboxy-1-cyclopropyl-7-fluoro-9-methyl-4-oxo-4H-quinolizine-8-yl)-pyrrolidin-3-ylamino]-piperidin-1-yl}-rifamycin S

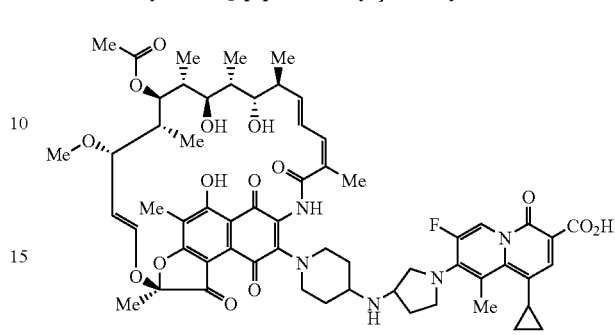

Synthesis: The title compound was prepared by using the same procedure as described for Example 24 except (R/S)-8-(3-amino-pyrrolidin-1-yl)-1-cyclopropyl-7-fluoro-9-methyl-4-oxo-4H-quinolizine-3-carboxylic acid (trifluoroacetate salt) was used in place of (R)-8-(3-aminomethyl-pyrrolidin-1-yl)-1-cyclopropyl-7-fluoro-9-methyl-4-oxo-4H-quinolizine-3-carboxylic acid (trifluoroacetate salt). ESI MS m/z 1122.5 (M+H⁺). ¹H NMR (400 MHz, CDCl₃) δ 13.90 (br s, 1H), 13.28 (s, 1H), 9.05 (d, J=9.6 Hz, 1H), 8.20 (s, 1H), 7.58 (s, 1H), 7.09-7.00 (m, 1H), 6.78-6.72 (m, 1H), 6.36 (d, J=10.8 Hz, 1H), 6.18 (dd, J=6.0, 15.6 Hz, 1H), 6.07 (d, J=12.4 Hz, 1H), 5.10-5.04 (m, 2H), 4.00-3.28 (m, ~15H), 3.10 (s, 3H), 3.08-3.01 (m, 2H), 2.68-2.62 (overlap with Me, m, 1H), 2.64 (s, 3H), 2.38-2.28 (overlap with Me, m, 2H), 2.27 (s, 3H), 2.18-2.08 (overlap with 2 Me, m, 1H), 2.12 (s, 3H), 2.09 (s, 3H), 1.85-1.48 (m, 4H), 1.74 (s, 3H), 1.28-1.20 (m, 1H), 1.04 (d, J=6.8 Hz, 3H), 1.05-0.92 (m, 2H), 0.88 (d, J=7.2 Hz, 3H), 0.71 (d, J=6.4 Hz, 3H), 0.68-0.66 (m, 2H), 0.17 (d, J=6.4 Hz, 3H).

EXAMPLE 29

(R/S)-3-(4-{[1-(3-Carboxy-1-cyclopropyl-7-fluoro-9-methyl-4-oxo-4H-quinolizine-8-yl)-pyrrolidin-3-yl]-methyl-amino}-piperidin-1-yl)-rifamycin S

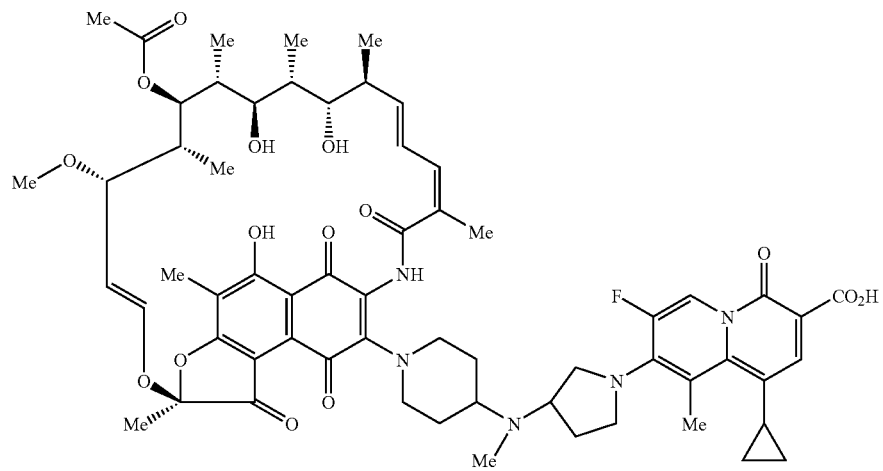

Synthesis: The title compound was prepared by using the same procedure as described for Example 24 except (R/S)-8-(3-methylamino-pyrrolidin-1-yl)-1-cyclopropyl-7-fluoro-9-methyl-4-oxo-4H-quinolizine-3-carboxylic acid (trfluoroacetate salt) was used in place of (R)-8-(3-aminomethyl-pyrrolidin-1-yl)-1-cyclopropyl-7-fluoro-9-methyl-4-oxo-4H-quinolizine-3-carboxylic acid (trfluoroacetate salt). ESI MS m/z 1136.5 (M+H$^+$). $^1$H NMR (400 MHz, CDCl$_3$) δ 13.90 (s, 1H), 13.30 (s, 1H), 9.11 (d, J=9.6 Hz, 1H), 8.24 (s, 1H), 7.58 (s, 1H), 7.09-7.00 (m, 1H), 6.42-6.36 (m, 1H), 6.22-6.16 (m, 1H), 6.07 (d, J=12.8 Hz, 1H), 5.12-5.08 (m, 2H), 4.05-3.32 (m, ~15H), 3.11 (s, 3H), 3.10-2.96 (m, 2H), 2.82-2.64 (m, 2H), 2.64 (s, 3H), 2.40-2.06 (overlap with 3 Me, m, 4H), 2.28 (s, 3H), 2.15, 2.13 (two singlets, 3H), 2.10, 2.09 (two singlets, 3H), 2.00-1.92 (m, 1H), 1.85-1.48 (overlap with Me, m, 4H), 1.76 (s, 3H), 1.28-1.20 (m, 1H), 1.16-1.08 (m, 1H), 1.05 (d, J=6.8 Hz, 3H), 0.98-0.86 (m, 4H), 0.74-0.68 (m, 5H), 0.17 (d, J=6.4 Hz, 3H).

EXAMPLE 30

3-{[4-(3-Carboxy-1-cyclopropyl-7-fluoro-9-methyl-4-oxo-4H-quinolizine-8-yl)-piperazin-1-yl-imino]-methyl}-rifamycin SV

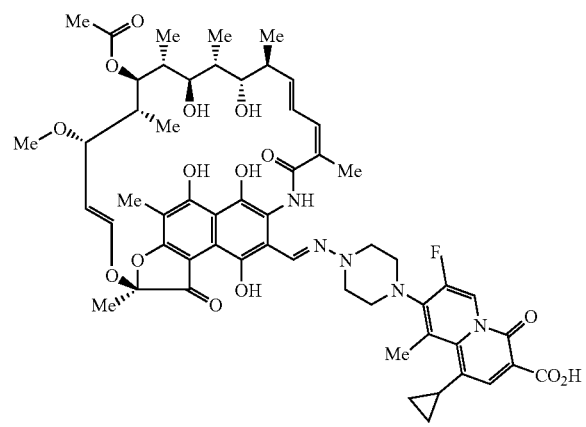

Synthesis: Step 1-3. 1-Cyclopropyl-7-fluoro-9-methyl-4-oxo-8-piperazin-1-yl-4H-quinolizine-3-carboxylic acid (trifluoroacetate salt):

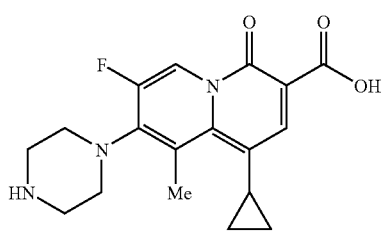

The title compound was prepared by using the same procedure as described in step 5-7 of example 4 except piperazine-1-carboxylic acid tert-butyl ester was used in place of 4-pyrrolidin-3-ylmethyl-piperazine-1-carboxylic acid tert-butyl ester. ESI MS m/z 346.1 (M+H$^+$).

Step 4. 1-Cyclopropyl-7-fluoro-9-methyl-8-(4-nitroso-piperazin-1-yl)-4-oxo-4H-quinolizine-3-carboxylic acid:

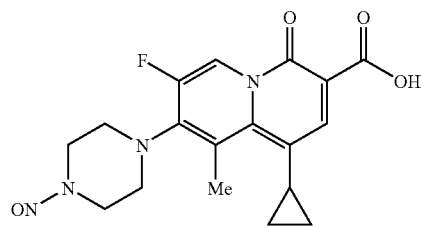

The suspension of product from step 4 (96 mg, 0.21 mmol) was suspended in THF (4.0 mL) and DMF (2.0 mL). tert-Butyl nitrite (0.1 mL, 0.84 mmol) was added into the suspension at room temperature. The resulting mixture was stirred at room temperature for 20 minutes and gradually became a clear yellow solution. The solution was evaporated to dryness to afford an orange solid. ESI MS m/z 375.2 (M+H$^+$).

Step 5: 3-{[4-(3-Carboxy-1-cyclopropyl-7-fluoro-9-methyl-4-oxo-4H-quinolizine-8-yl)-piperazin-1-yl-imino]-methyl}-rifamycin SV: The resulting orange solid in step 4 was suspended in acetic acid (2.5 mL) and H$_2$O (2.5 mL). Zinc dust (64 mg, 0.98 mmol) was added to the suspension and the mixture was stirred at room temperature for 20-30 minutes. During this time, the reactant became clear solution with some suspended Zinc dust. Filtered through Celite to remove the unreacted zinc and washed the reaction flask and Celite with methanol (5.0 mL). The combined methanol/acetic acid/water solution was added the sodium acetate (~1 g) to adjust the pH to 5-6. To this solution was added 3-formyl rifamycin SV (104 mg, 0.13 mmol). The resulting solution was stirred at room temperature for three hours and then partitioned between dichloromethane and water. The separated organic layer was washed with brine, dried over sodium sulfate and concentrated in vacuo. The residue was purified by preparative thin layer chromatography (10% methanol in dichloromethane) to give the title compound as an orange solid (97 mg, 43% in step 4 and 5). ESI MS m/z 1068.4 (M+H$^+$). $^1$H NMR (400 MHz, CDCl$_3$) δ 13.80 (br s, 1H), 13.45 (s, 1H), 13.22 (s, 1H), 13.05 (s, 1H), 12.14 (s, 1H), 9.23 (d, J=8.8 Hz, 1H), 8.45 (s, 1H), 8.38 (s, 1H), 6.62 (dd, J=11.6, 14.4 Hz, 1H), 6.45 (d, J=11.2 Hz, 1H), 6.22 (d, J=12.8 Hz, 1H), 5.99 (dd, J=5.2, 15.2 Hz, 1H), 5.12 (dd, J=6.4, 12.8 Hz, 1H), 4.96 (d, J=10.4 Hz, 1H), 3.81 (d, J=9.6 Hz, 1H), 3.69 (d, J=4.8 Hz, 1H), 3.66-3.56 (m, 4H), 3.55 (s, 1H), 3.51 (d, J=6.8 Hz, 1H), 3.39-3.28 (m, 4H), 3.06 (s, 3H), 3.06-3.02 (m, 1H), 2.86 (s, 3H), 2.46-2.38 (m, 1H), 2.32-2.27 (m, 1H), 2.25 (s, 3H), 2.11 (s, 3H), 2.08 (s, 3H), 1.82 (s, 3H), 1.77-1.71 (m, 1H), 1.60-1.55 (m, 1H), 1.42-1.36 (m, 1H), 1.06 (d, J=5.2 Hz, 2H), 1.04 (d, J=7.2 Hz, 3H), 0.93 (d, J=6.8 Hz, 3H), 0.72 (d, J=5.2 Hz, 2H), 0.64 (d, J=6.8 HZ, 3H), −0.27 (d, J=6.8 Hz, 3H).

EXAMPLE 31

(R/S)-3-({4-[1-(3-Carboxy-1-cyclopropyl-7-fluoro-9-methyl-4-oxo-4H-quinolizine-8-yl)-pyrrolidin-3-ylmethyl]-piperazin-1-ylimino}-methyl)-rifamycin SV

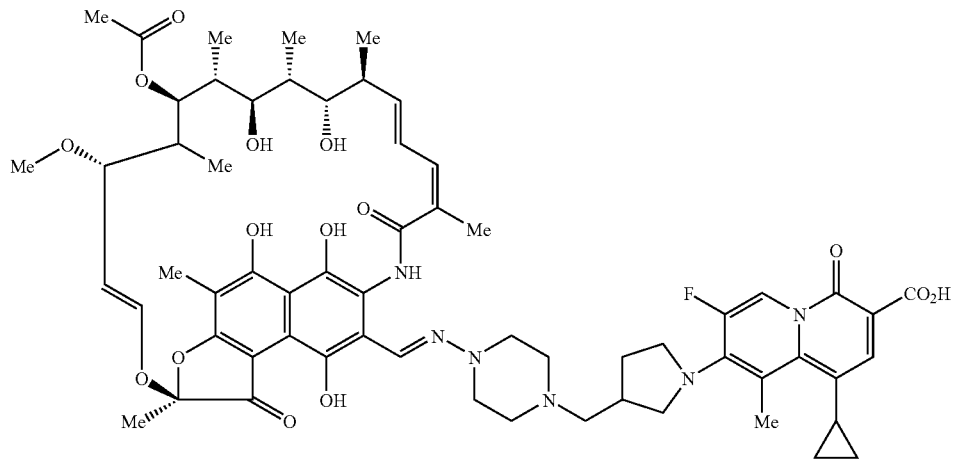

Synthesis: The title compound was prepared by using the same procedure as described in Step 4-5 of Example 30 except (R/S)-1-cyclopropyl-7-fluoro-9-methyl-4-oxo-8-(3-piperazin-1-ylmethyl-pyrrolidin-1-yl)-4H-quinolizine-3-carboxylic acid (trifluoroacetate salt) was used in place of 1-cyclopropyl-7-fluoro-9-methyl-4-oxo-8-piperidin-4-yl-4H-quinolizine-3-carboxylic acid (trifluoroacetate salt). ESI MS m/z 1151.5 (M+H$^+$). $^1$H NMR (400 MHz, CDCl$_3$) δ 13.22 (br s, 1H), 13.19 (s, 1H), 12.05 (s, 1H), 9.08 (d, J=10.4 Hz, 1H), 8.31 (s, 1H), 8.24 (s, 1H), 6.59 (dd, J=11.6, 15.2 Hz, 1H), 6.39 (d, J=11.2 Hz, 1H), 6.22 (d, J=12.4 Hz, 1H), 5.93 (dd, J=4.8, 15.2 Hz, 1H), 5.11 (dd, J=6.4, 12.4 Hz, 1H), 4.95 (d, J=10.4 Hz, 1H), 3.88-3.68 (m, 4H), 3.63-3.57 (m, 1H), 3.49 (d, J=6.8 Hz, 1H), 3.21-3.09 (m, 4H), 3.05 (s, 3H), 3.05-3.01 (m, 1H), 2.71-2.52 (m, 10H), 2.42-2.38 (m, 1H), 2.24 (s, 3H), 2.22-2.04 (overlap with 2 Me, m, 4H), 2.09 (s, 3H), 2.08 (s, 3H), 1.81 (s, 3H), 1.76-1.70 (m, 1H), 1.58-1.52 (m, 1H), 1.42-1.26 (m, 2H), 1.03 (d, J=7.2 Hz, 3H), 0.98-0.87 (m, 2H), 0.89 (d, J=6.8 Hz, 3H), 0.70-0.62 (m, 2H), 0.61 (d, J=7.2 Hz, 3H), −0.29 (d, J=6.8 Hz, 3H).

EXAMPLE 32

(S)-3-({4-[1-(3-Carboxy-1-cyclopropyl-7-fluoro-9-methyl-4-oxo-4H-quinolizine-8-yl)-pyrrolidin-3-yl-oxycarbonyl]-piperazin-1-yl-imino}-methyl)-rifamycin SV

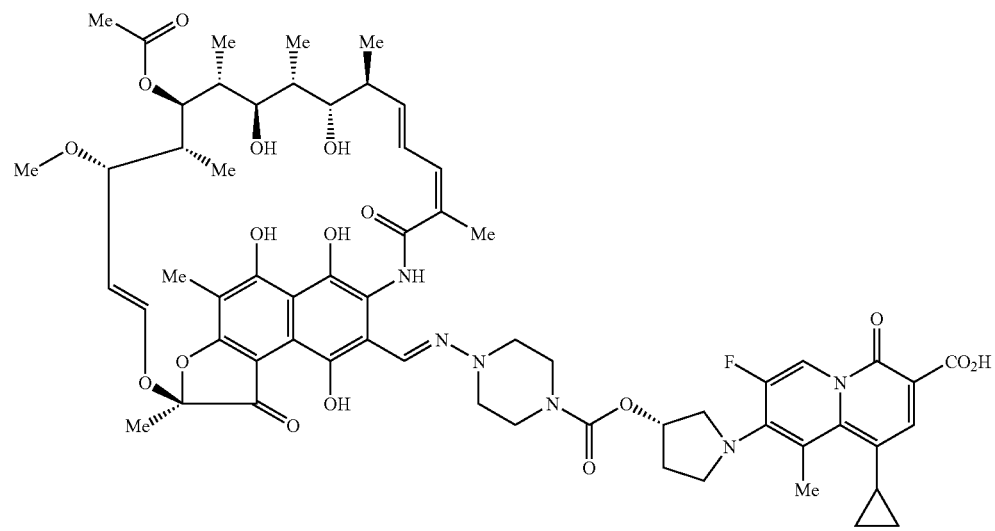

Synthesis: The title compound was prepared by using the same procedure as described in Step 4-5 in Example 30 except (S)-1-cyclopropyl-7-fluoro-9-methyl-4-oxo-8-[3-(piperazine-1-carbonyloxy)-pyrrolidin-1-yl]-4H-quinolizine-3-carboxylic acid (trifluoroacetate salt) was used in place of 1-cyclopropyl-7-fluoro-9-methyl-4-oxo-8-piperidin-4-yl-4H-quinolizine-3-carboxylic acid (trifluoroacetate salt). ESI MS m/z 1181.5 (M+H$^+$). $^1$H NMR (400 MHz, CDCl$_3$) δ 13.80 (s, 1H), 13.41 (br s, 1H), 13.22 (s, 1H), 13.00 (s, 1H), 12.09 (s, 1H), 9.10 (d, J=10.0 Hz, 1H), 8.35 (s, 1H), 8.24 (s, 1H), 6.59 (dd, J=11.2, 15.6 Hz, 1H), 6.40 (d, J=11.2 Hz, 1H), 6.21 (d, J=12.4 Hz, 1H), 5.95 (dd, J=5.2, 15.2 Hz, 1H), 5.44 (s, 1H), 5.10 (dd, J=6.4, 12.8 Hz, 1H), 4.93 (d, J=9.6 Hz, 1H), 4.20-4.05 (m, 2H), 3.76-3.48 (m, ~9H), 3.18-3.02 (overlap with Me, m, 4H), 3.05 (s, 3H), 2.65 (s, 3H), 2.42-2.36 (m, 1H), 2.32-2.28 (m, 2H), 2.24 (s, 3H), 2.20-2.16 (m, 1H), 2.07 (app s, 6H), 1.81 (s, 3H), 1.70-1.50 (m, 4H), 1.38-1.32 (m, 1H), 1.11-1.06 (m, 1H), 1.10 (d, J=7.2 Hz, 3H), 0.98-0.92 (m, 1H), 0.85 (d, J=7.2 Hz, 3H), 0.71-0.64 (m, 2H), 0.59 (d, J=7.2 Hz, 3H), −0.31 (d, J=7.2 Hz, 3H).

Synthesis: The title compound was prepared by using the same procedure as described in Step 4-5 in Example 30 except (R/S)-1-cyclopropyl-7-fluoro-9-methyl-8-{3-[(methyl-piperidin-4-yl-amino)-methyl]-pyrrolidin-1-yl}-4-oxo-4H-quinolizine-3-carboxylic acid (trifluoroacetate salt) was used in place of 1-cyclopropyl-7-fluoro-9-methyl-4-oxo-8-piperidin-4-yl-4H-quinolizine-3-carboxylic acid (trifluoroacetate salt). ESI MS m/z 1179.5 (M+H$^+$). $^1$H NMR (400 MHz, CDCl$_3$) δ 13.84 (s, 1H), 13.42 (br s, 1H), 13.21 (s, 1H), 11.99 (s, 1H), 9.05 (d, J=10.4 Hz, 1H), 8.21 (app s, 2H), 6.53 (dd, J=11.2, 15.6 Hz, 1H), 6.36 (d, J=11.2 Hz, 1H), 6.18 (d, J=12.8 Hz, 1H), 5.90 (dd, J=5.2, 15.2 Hz, 1H), 5.04 (dd, J=7.2, 12.4 Hz, 1H), 4.89 (d, J=10.8 Hz, 1H), 3.81-3.54 (m, ~8H), 3.52-3.49 (m, 1H), 3.45-3.42 (m, 2H), 3.00 (s, 3H), 3.00-2.96 (m, 1H), 2.62-2.40 (m, ~6H), 2.57 (s, 3H), 2.38-2.32 (m, 1H), 2.26 (s, 3H), 2.19 (s, 3H), 2.19-2.00 (overlap with 2 Me, m, ~4H), 2.04 (s, 3H), 2.02 (s, 3H), 1.88-1.70 (overlap with Me, m, ~3H), 1.76 (s, 3H), 1.36-1.23 (m, 2H), 0.97 (d, J=6.8 Hz, 3H), 0.92-0.88 (m, 2H), 0.82 (d, J=6.8 Hz, 3H), 0.62-0.57 (m, 2H), 0.56 (d, J=6.4 Hz, 3H), −0.34 (d, J=7.2 Hz, 3H).

EXAMPLE 33

(R/S)-3-[(4-{[1-(3-Carboxy-1-cyclopropyl-7-fluoro-9-methyl-4-oxo-4H-quinolizine-8-yl)-pyrrolidin-3-ylmethyl]-methyl-amino}-piperidin-1-ylimino)-methyl]-rifamycin SV

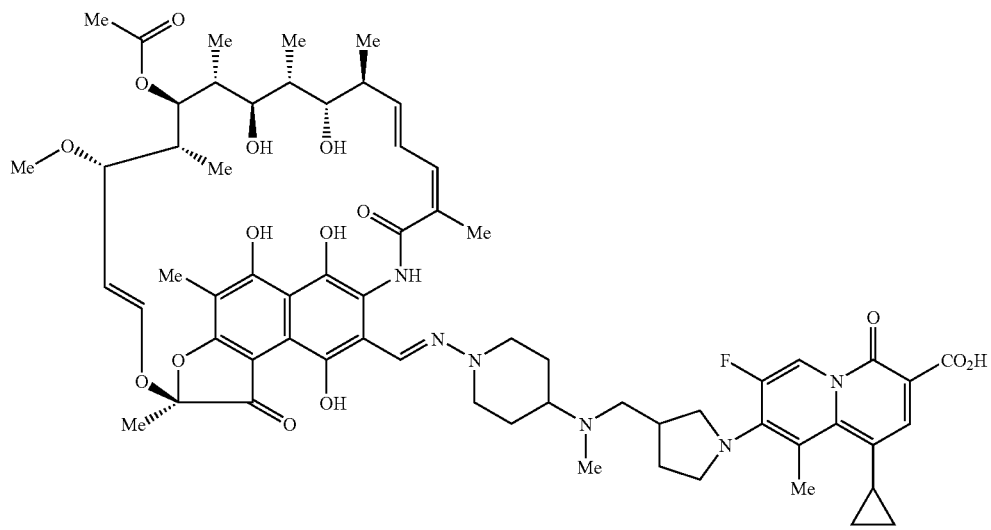

EXAMPLE 34

(R/S)-3-({4-[1-(3-Carboxy-1-cyclopropl-7-fluoro-9-methyl-4-oxo-4H-quinolizine-8-yl)-pyrrolidin-3-ylmethoxy]-piperidin-1-ylimino}-methyl)-rifamycin SV

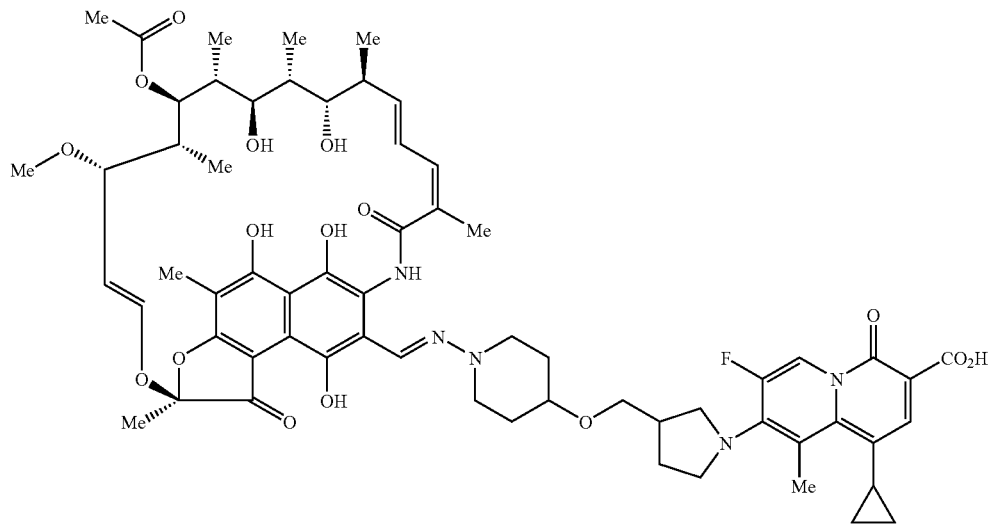

Synthesis: The title compound was prepared by using the same procedure as described in Step 4-5 in Example 30 except (R/S)-1-cyclopropyl-7-fluoro-9-methyl-4-oxo-8-[3-(piperidin-4-yloxymethyl)-pyrrolidin-1-yl]-4H-quinolizine-3-carboxylic acid (trifluoroacetate salt) was used in place of 1-cyclopropyl-7-fluoro-9-methyl-4-oxo-8-piperidin-4-yl-4H-quinolizine-3-carboxylic acid (trifluoroacetate salt). ESI MS m/z 1188.5 (M+Na$^+$). $^1$H NMR (400 MHz, CDCl$_3$) δ 13.82 (s, 1H), 13.42 (br s, 1H), 13.21 (s, 1H), 11.98 (two singlets, 1H), 9.05 (two pair of doublets, J=10.4 Hz, 1H), 8.22-8.18 (m, 2H), 6.54 (dd, J=11.2, 15.6 Hz, 1H), 6.36 (d, J=11.2 Hz, 1H), 6.18 (d, J=11.2 Hz, 1H), 5.90 (dd, J=5.2, 15.2 Hz, 1H), 5.03 (dd, J=7.2, 12.4 Hz, 1H), 4.88 (d, J=10.8 Hz, 1H), 4.28-4.18 (m, 3H), 3.78-3.06 (m, ~15H), 3.00 (s, 3H), 3.00-2.96 (m, 1H), 2.56 (s, 3H), 2.38-2.30 (m, 1H), 2.19 (s, 3H), 2.19-1.70 (overlap with 3 Me, m, ~6H), 2.03 (s, 3H), 2.00 (s, 3H), 1.76 (two singlets, 3H), 1.32-1.18 (m, 2H), 0.96 (d, J=6.8 Hz, 3H), 0.92-0.88 (m, 2H), 0.81 (d, J=6.4 Hz, 3H), 0.62-0.57 (m, 2H), 0.55 (d, J=6.4 Hz, 3H), −0.36 (d, J=6.8 Hz, 3H).

EXAMPLE 35

(S)-3-{[1-(3-Carboxy-1-cyclopropyl-7-fluoro-9-methyl-4-oxo-4H-quinolizine-8-yl)-pyrrolidin-3-yl]-hydrazinomethyl}-rifamycin SV

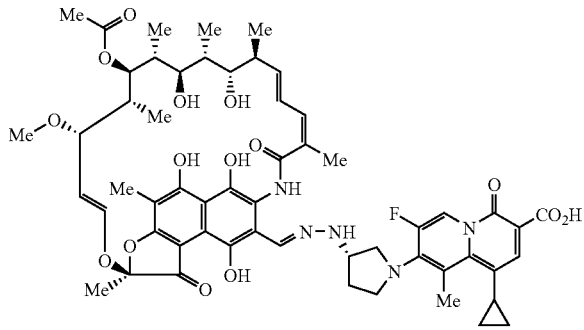

Synthesis: To a solution of (S)-8-(3-amino-pyrrolidin-1-yl)-1-cyclopropyl-7-fluoro-9-methyl-4-oxo-4H-quinolizine-3-carboxylic acid (trifluoroacetate salt) (38 mg, 0.08 mmol) in 1N aq NaOH (0.5 mL) was added the solution of hydroxylamine-O-sulfonic acid (14 mg, 0.12 mmol) in water (0.08 mL) at 0° C. The solution was stirred at same temperature for three hours. Acetic acid (0.5 mL) was added followed by 3-formyl rifamycin SV (5.0 mg, 0.007 mmol). After stirring at room temperature for 30 minutes, the solution was partitioned between dichloromethane and water. The separated organic layer was washed with brine, dried over sodium sulfate, concentrated in vacuo. The residue was purified by preparative thin layer chromatography (10% methanol in dichloromethane) to give the title compound as an orange solid (4.5 mg, 5%). ESI MS m/z 1090.6 (M+Na$^+$). $^1$H NMR (400 MHz, CDCl$_3$) δ 13.82 (br s, 1H), 13.38 (br s, 1H), 13.16 (br s, 1H), 12.62 (s, 1H), 12.06 (s, 1H), 8.99 (d, J=10.4 Hz, 1H), 8.51 (s, 1H), 8.15 (s, 1H), 6.58 (dd, J=11.6, 15.2 Hz, 1H), 6.41 (d, J=10.8 Hz, 1H), 6.20 (d, J=12.4 Hz, 1H), 5.98 (dd, J=5.2, 14.0 Hz, 1H), 5.84 (app s, 1H), 5.09 (dd, J=6.4, 12.8 Hz, 1H), 4.94 (d, J=10.8 Hz, 1H), 4.14 (brs 1H), 4.04-3.96 (m, 2H), 3.80 (d, J=9.6 Hz, 1H), 3.72-3.66 (m, 3H), 3.56 (app s, 1H), 3.51 (d, J=6.8 Hz, 1H), 3.06 (s, 3H), 3.06-3.02 (m, 1H), 2.64 (s, 3H), 2.64-2.60 (m, 1H), 2.46-2.38 (m, 1H), 2.32-2.27 (m, 1H), 2.24 (s, 3H), 2.19-2.11 (m, 1H), 2.10 (s, 3H), 2.08 (s, 3H), 1.80 (s, 3H), 1.76-1.54 (m, 2H), 1.41-1.35 (m, 1H), 1.04 (d, J=6.8 Hz, 3H), 1.04-0.94 (m, 2H), 0.91 (d, J=6.8 Hz, 3H), 0.71-0.66 (m, 2H), 0.62 (d, J=6.8 Hz, 3H), −0.28 (d, J=6.4 Hz, 3H).

EXAMPLE 36

(R/S)-3-{[1-(3-Carboxy-1-cyclopropyl-7-fluoro-9-methyl-4-oxo-4H-quinolizine-8-yl)-pyrrolidin-3-yl]-hydrazinomethyl}-rifamycin SV

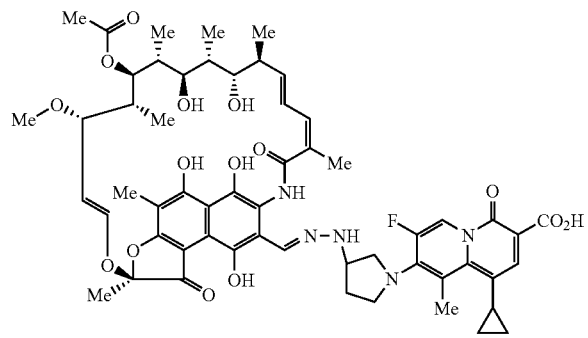

Synthesis: Step 1. (R/S)-N'-(1-Benzyl-pyrrolidin-3-yl)-N'-(tert-butoxycarbonyl)-hydrazinecarboxylic acid tert-butyl ester:

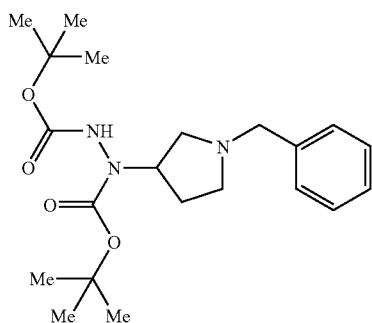

To a stirred solution of 1-benzyl-pyrrolidin-3-one (500 mg, 2.9 mmol) in methanol (10 mL) was added hydrazinecarboxylic acid tert-butyl ester (380 mg, 2.9 mmol) followed by acetic acid (0.2 mL). The mixture was allowed to stir at room temperature for one hour, cooled to 0° C. and then p-toluene-4-sulfonic acid monohydrate (1.1 g, 6.0 mmol) was added, followed by NaBH$_3$CN (200 mg, 3.18 mmol). When the hydrazine was all consumed, the reaction was quenched by saturated aq NaHCO$_3$ (5.0 mL). Methanol was removed in vacuo and the residue was partitioned between dichloromethane and 15% aq NaOH. The organic layer was separated, and aqueous layer was extracted with dichloromethane once. The combined extracts were dried over Na$_2$SO$_4$ and concentrated to give an oil, which was dissolved in THF (15 mL). To this solution was added di-tert-butyl dicarbonate (932 mg, 4.35 mmol), and the mixture was allowed to stir at room temperature for four hours and heated at 65° C. for two hours. The reaction mixture was condensed and purified by flash chromatography on silica gel (50% ethyl acetate in hexanes) to give an oily product (500 mg, ~40%).

Step 2. (R/S)-N'-(Pyrrolidin-3-yl)-N'-(tert-butoxycarbonyl)-hydrazinecarboxylic acid tert-butyl ester:

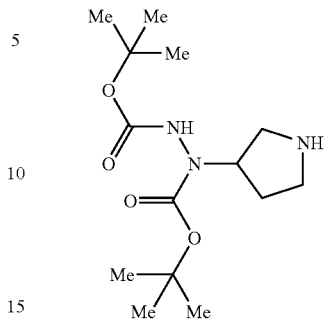

The oily compound from step 1 (500 mg, 1.7 mmol) was dissolved in acetic acid (10 mL), and 20% Pd(OH)$_2$/C (200 mg) was added. The mixture was allowed to stir at room temperature under hydrogen balloon (1 atm) for 18 hours. The catalyst was filtered, and acetic acid was removed in vacuo. The residue was partitioned between dichloromethane and 15% aq NaOH. The aqueous layer was extracted with dichloromethane, and the combined organic extracts were dried over Na$_2$SO$_4$ and concentrated to give an oily product (250 mg, 65%).

Step 4-6: (R/S)-1-Cyclopropyl-7-fluoro-8-(3-hydrazino-pyrrolidin-1-yl)-9-methyl-4-oxo-4H-quinolizine-3-carboxylic acid (trifluoroacetate salt):

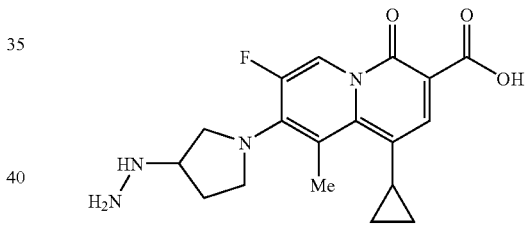

The title compound was prepared by using the same procedure as described in step 5-7 of example 7 except (R/S)-N'-(pyrrolidin-3-yl)-N-(tert-butoxycarbonyl)-hydrazinecarboxylic acid tert-butyl ester was used in place of (R/S)-4-pyrrolidin-3-ylmethyl-piperazine-1-carboxylic acid tert-butyl ester. ESI MS m/z 361.1 (M+H$^+$).

Step 7: 3-{[1-(3-Carboxy-1-cyclopropyl-7-fluoro-9-methyl-4-oxo-4H-quinolizine-8-yl)-pyrrolidin-3-yl]-hydrazonomethyl}-rifamycin SV: The crude product from step 6 (trifluoroacetate salt, 95 mg, ~0.12 mmol) was dissolved in MeOH (2.0 mL) at 0° C. NaOAc (54 mg, 0.66 mmol) was added and stirred for 5 min. Then 3-formyl rifamycin SV (87 mg, 0.12 mmol) was added in one portion at 0° C. and the reaction mixture was stirred at same temperature for one hour. The mixture was partitioned between dichloromethane and water, the separated organic layer was washed with brine, dried over sodium sulfate. After concentration, crude sample was purified by preparative thin layer chromatography (10% methanol in dichloromethane) to give as orange solid (90 mg, 70%). ESI MS m/z 1090.6 (M+Na$^+$). $^1$H NMR (400 MHz, CDCl$_3$) δ 13.82 (br s, 1H), 13.38 (br s, 1H), 13.16 (br s, 1H), 12.62 (s, 1H), 12.06 (s, 1H), 8.99 (d, J=10.4

Hz, 1H), 8.51 (s, 1H), 8.15 (s, 1H), 6.58 (dd, J=11.6, 15.2 Hz, 1H), 6.41 (d, J=10.8 Hz, 1H), 6.20 (d, J=12.4 Hz, 1H), 5.98 (dd, J=5.2, 14.0 Hz, 1H), 5.84 (app s, 1H), 5.09 (dd, J=6.4, 12.8 Hz, 1H), 4.94 (d, J=10.8 Hz, 1H), 4.14 (br s, 1H), 4.04-3.96 (m, 2H), 3.80 (d, J=9.6 Hz, 1H), 3.72-3.66 (m, 3H), 3.56 (app s, 1H), 3.51 (d, J=6.8 Hz, 1H), 3.06 (s, 3H), 3.06-3.02 (m, 1H), 2.64 (s, 3H), 2.64-2.60 (m, 1H), 2.46-2.38 (m, 1H), 2.32-2.27 (m, 1H), 2.24 (s, 3H), 2.19-2.11 (m, 1H), 2.10 (s, 3H), 2.08 (s, 3H), 1.80 (s, 3H), 1.76-1.54 (m, 2H), 1.41-1.35 (m, 1H), 1.04 (d, J=6.8 Hz, 3H), 1.04-0.94 (m, 2H), 0.91 (d, J=6.8 Hz, 3H), 0.71-0.66 (m, 2H), 0.62 (d, J=6.8 Hz, 3H), −0.28 (d, J=6.4 Hz, 3H).

EXAMPLE 37

(R/S)-3-{[1-(3-Carboxy-1-cyclopropl-7-fluoro-9-methyl-4-oxo-4H-quinolizine-8-yl)-pyrrolidin-3-ylmethyl]-hydrazinomethyl}-rifamycin SV

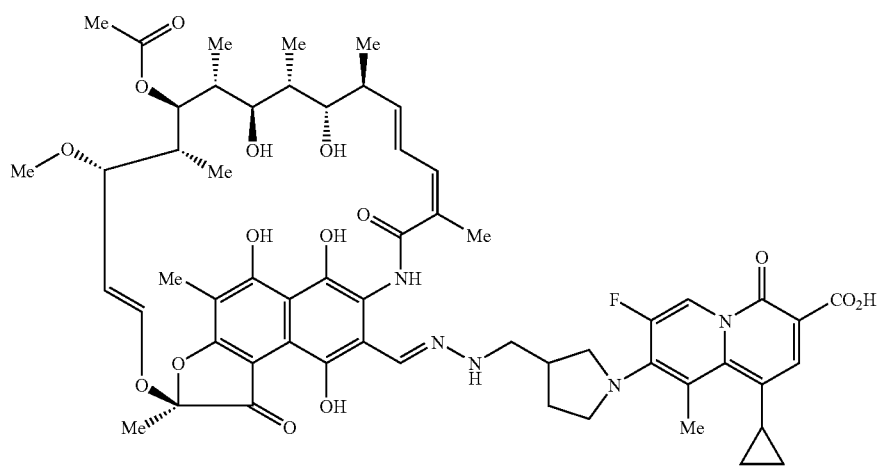

Synthesis: The title compound was prepared by using the same procedure as described for Example 36 except (R/S)-1-benzyl-pyrrolidine-3-carbaldehyde was used in place of 1-benzyl-pyrrolidin-3-one. ESI MS m/z 1082.4 (M+H$^+$). $^1$H NMR (400 MHz, CDCl$_3$) δ (~1:1 mixture of two diastereomers) 13.78, 13.72 (two singlets, 1H), 13.36, 13.22 (two singlets, 1H), 13.11, 13.04 (two singlets, 1H), 12.69, 12.68 (two singlets, 1H), 12.02 (s, 1H), 9.02, 8.99 (two doublets, J=10.4 Hz, 1H), 8.38, 8.32 (two singlets, 1H), 8.14, 8.07 (two singlets, 1H), 6.56-5.99 (m, 1H), 6.41-6.36 (m, 1H), 6.17 (d, J=13.2 Hz, 1H), 5.92 (dd, J=5.2, 14.0 Hz, 1H), 5.78-5.62 (m, 1H), 5.08-5.01 (m, 1H), 4.91-4.85 (m, 1H), 3.82-3.24 (m, ~13H), 3.00, 2.99 (two singlets, 3H), 2.57, 2.56 (two singlets, 3H), 2.40-2.32 (m, 1H), 2.20 (s, 3H), 2.19-2.06 (m, 2H), 2.06, 2.04 (two singlets, 3H), 2.03, 2.02 (two singlets, 3H), 1.79-1.77 (two singlets, 3H), 1.76-1.60 (m, 2H), 1.38-1.30 (m, 1H), 0.99-0.90 (m, 5H), 0.83 (d, J=6.0 Hz, 3H), 0.70-0.52 (m, 5H), −0.34, −0.37 (two doublets, J=6.8 Hz, 3H).

EXAMPLE 38

(R/S)-3-{[1-(3-Carboxy-1-cyclopropyl-7-fluoro-9-methyl-4-oxo-4H-quinolizine-8-yl)-pyrrolidin-3-yl]-(N-methyl-hydrazino)-methyl}-rifamycin SV

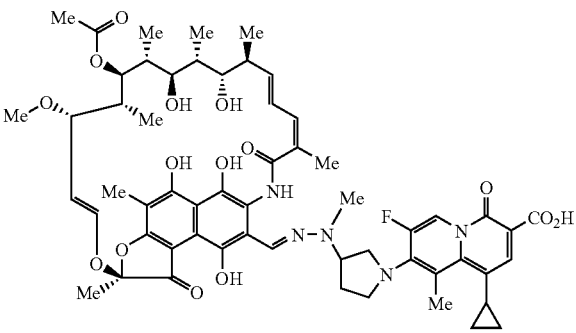

Step 1-3. (R/S)-1-Cyclopropyl-7-fluoro-9-methyl-8-(3-methylamino-pyrrolidin-1-yl)-4-oxo-4H-quinolizine-3-carboxylic acid (trifluoroacetate salt):

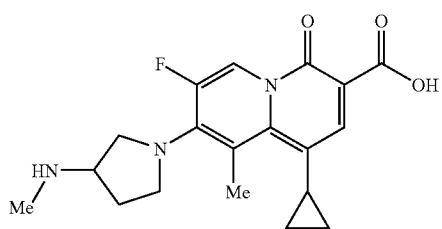

The title compound was prepared by using the same procedure as described in step 5-7 of example 7 except (R/S)-methyl-pyrrolidin-3-yl-carbamic acid tert-butyl ester was used in place of (R/S)-4-pyrrolidin-3-ylmethyl-piperazine-1-carboxylic acid tert-butyl ester. ESI MS m/z 360.1 (M+H$^+$).

Step 4-5. (R/S)-3-{[1-(3-Carboxy-1-cyclopropyl-7-fluoro-9-methyl-4-oxo-4H-quinolizine-8-yl)-pyrrolidin-3-yl]-methyl-hydrazonomethyl}-rifamycin SV: The title compound was prepared by using the same procedure as described in Step 4-5 in Example 33 except (R/S)-1-cyclopropyl-7-fluoro-9-methyl-8-(3-methylamino-pyrrolidin-1-yl)-4-oxo-4H-quinolizine-3-carboxylic acid (trifluoroacetate salt) was used in place of 1-cyclopropyl-7-fluoro-9-methyl-4-oxo-8-piperidin-4-yl-4H-quinolizine-3-carboxylic acid (trifluoroacetate salt). ESI MS m/z 1082.3 (M+H$^+$).

EXAMPLE 39

(R/S)-3-({3-[1-(3-Carboxy-1-cyclopropyl-7-fluoro-9-methyl-4-oxo-4H-quinolizine-8-yl)-piperidin-4-yl]-pyrrolidin-1-ylimino}-methyl)-rifamycin SV and (R/S)-3-({4-[1-(3-Carboxy-1-cyclopropyl-7-fluoro-9-methyl-4-oxo-4H-quinolizine-8-yl)-pyrrolidin-3-yl]-piperidin-1-ylimino}-methyl)-rifamycin SV

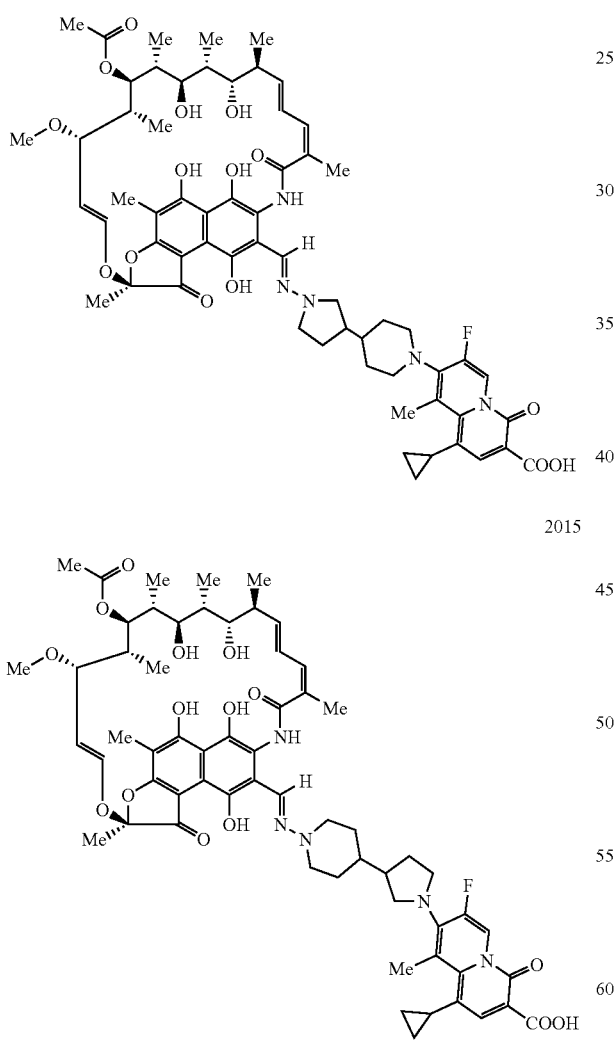

2014

2015

Synthesis: The title compounds were prepared by using the same procedure as described in Step 4-5 in Example 30 except the regioisomers mixture from Step 4 of Example 17 was used in place of 1-cyclopropyl-7-fluoro-9-methyl-4-oxo-8-piperidin-4-yl-4H-quinolizine-3-carboxylic acid (trifluoroacetate salt). Compound 2014: ESI MS m/z 1136.5 (M+H$^+$); $^1$H NMR (400 MHz, CDCl$_3$) δ 13.82 (s, 1H), 13.15 (2 s, 1H), 13.18 (s, 1H), 13.10 (2 s, 1H), 11.89 (s, 1H), 9.14 (d, J=8.6 Hz, 1H), 8.30 (s, 1H), 7.72 (s, 1H), 6.48 (m, 1H), 6.31 (d, J=7.0 Hz, 1H), 6.18 (d, J=12.5 Hz, 1H), 5.85 (dd, J=5.5, 15.6 Hz, 1H), 5.04 (dd, J=7.1, 13.5 Hz, 1H), 4.87 (d, J=9.9 Hz, 1H), 3.72 (d, J=9.5 Hz, 1H), 3.58 (d, J=4.6 Hz, 1H), 3.53-3.20 (m, 4H), 2.98 (s, 3H), 2.95 (m, 1H), 2.72 (s, 3H), 2.32 (m, 2H), 2.20 (m, 2H), 2.16 (s, 3H), 2.07 (m, 2H), 2.03 (s, 3H), 2.00 (s, 3H), 1.86 (d, J=7.0 Hz, 1H), 1.79 (m, 1H), 1.72 (s, 3H), 1.65 (m, 1H), 1.50 (m, 4H), 1.31 (m, 1H), 0.95 (d, J=7.0 Hz, 3H), 0.80 (m, 1H), 0.75 (d, J=7.0 Hz, 3H), 0.63 (d, J=5.7 Hz, 3H), 0.58 (d, J=6.4 Hz, 3H), −0.32 (d, J=6.9 Hz, 3H); Compound 2015: ESI MS m/z 1136.5 (M+H$^+$); $^1$H NMR (400 MHz, CDCl$_3$) δ 13.81 (s, 1H), 13.43 (s, 1H), 13.20 (s, 1H), 13.18 (s, 1H), 11.97 (s, 1H), 9.04 (d, J=10.3 Hz, 1H), 8.23 (s, 1H), 8.20 (s, 1H), 6.52 (dd, J=10.8, 15.8 Hz, 1H), 6.32 (d, J=11.8 Hz, 1H), 6.16 (d, J=13.5 Hz, 1H), 5.86 (d, J=14.9 Hz, 1H), 5.04 (dd, J=7.2, 12.4 Hz, 1H), 4.87 (d, J=11.3 Hz, 1H), 3.91 (m, 1H), 3.70 (d, J=9.4 Hz, 1H), 3.68-3.40 (m, 6H), 2.97 (s, 3H), 2.95 (m, 1H), 2.56 (m, 2H), 2.55 (s, 3H), 2.32 (m, 1H), 2.20 (m, 1H), 2.16 (s, 3H), 2.11 (m, 1H), 2.01 (s, 3H), 2.00 (s, 3H), 1.82 (m, 1H), 1.73 (s, 1H), 1.63 (m, 2H), 1.40 (m, 2H), 1.30 (m, 1H), 1.02 (m, 1H), 0.95 (d, J=7.1 Hz, 3H), 0.80 (d, J=5.2 Hz, 3H), 0.64 (m, 1H), 0.55 (d, J=6.4 Hz, 3H), −0.36 (d, J=7.2 Hz, 3H).

EXAMPLE 40

3-{[5-(3-Carboxy-1-cyclopropyl-7-fluoro-9-methyl-4-oxo-4H-quinolizin-8-yl)-hexahydro-pyrrolo[3,4-c]pyrrol-2-ylimino]-methyl}-rifamycin SV

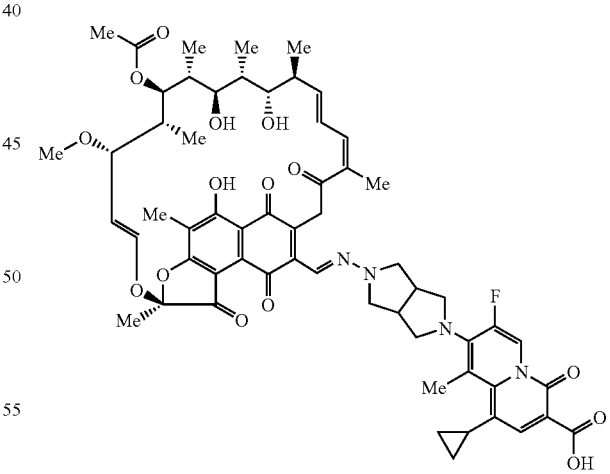

Synthesis: The title compound was prepared by using the same procedure as described in Step 4-5 in Example 30 except 1-cyclopropyl-7-fluoro-8-(hexahydro-pyrrolo[3,4-c]pyrrol-2-yl)-9-methyl-4-oxo-4H-quinolizine-3-carboxylic acid (trifluoroacetate salt) was used in place of 1-cyclopropyl-7-fluoro-9-methyl-4-oxo-8-piperidin-4-yl-4H-quinolizine-3-carboxylic acid (trifluoroacetate salt). ESI MS m/z 1092.4 (M+H$^+$).

EXAMPLE 41

(R/S, R/S)-3-({3-[1-(3-Carboxy-1-cyclopropyl-7-fluoro-9-methyl-4-oxo-4H-quinolizine-8-yl)-piperidin-3-yl]-pyrrolidin-1-ylimino}-methyl)-rifamycin SV

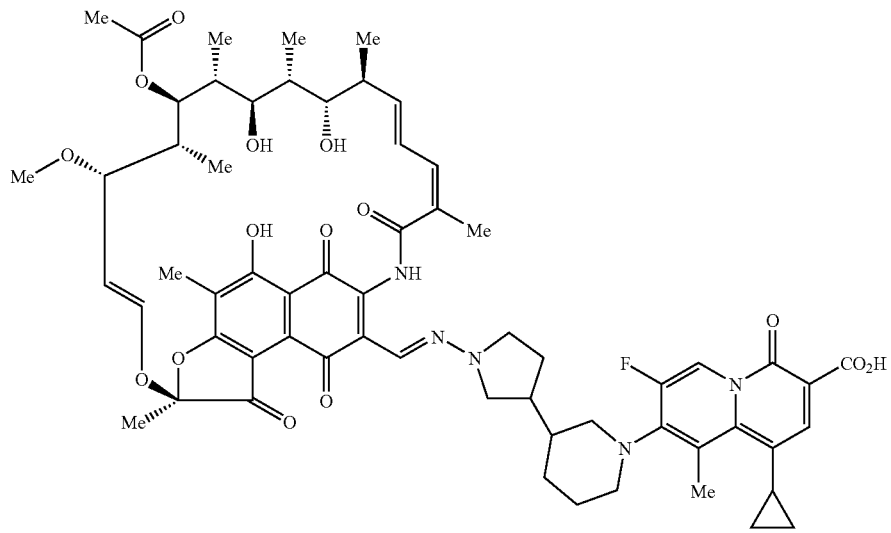

Synthesis: The title compound was prepared by using the same procedure as described in Step 4-5 in Example 30 except (R/S, R/S)-1-cyclopropyl-7-fluoro-9-methyl-4-oxo-8-(3-pyrrolidin-3-yl-piperidin-1-yl)-4H-quinolizine-3-carboxylic acid (trifluoroacetate salt) was used in place of 1-cyclopropyl-7-fluoro-9-methyl-4-oxo-8-piperidin-4-yl-4H-quinolizine-3-carboxylic acid (trifluoroacetate salt). ESI MS m/z 1118.5 (M+H$^+$), 1150.3 (M+Na$^+$). $^1$H NMR (400 MHz, CDCl$_3$) δ 11.94 (s, 1H), 9.20 (m, 1H), 8.35 (d, J=7.04 Hz, 1H), 7.79 (s, 1H), 6.54 (m, 1H), 6.35 (m, 1H), 6.23 (d, J=12.52 Hz, 1H), 5.92 (m, 1H), 5.11 (dd, J=7.04, 12.52 Hz, 1H), 4.95 (d, J=10.95 Hz, 1H), 3.77 (t, J=7.82 Hz, 1H), 3.65 (m, 1H), 3.53 (m, 1H), 3.47 (m, 4H), 3.32 (m, 1H), 3.04 (s, 3H), 3.09-3.01 (m, 3H), 2.77 (s, 3H), 2.38 (m, 1H), 2.26 (m, 1H), 2.21 (s, 3H), 2.09 (m, 5H), 2.06 (s, 3H), 1.90 (m, 5H), 1.79 (s, 3H), 1.75-1.50 (m, 5H), 1.02 (m, 5H), 0.81 (m, 3H), 0.69 (m, 2H) 0.64 (m, 3H), −0.26 (m, 3H).

EXAMPLE 42

(R/S)-3-({4-[1-(3-Carboxy-1-cyclopropyl-7-fluoro-9-methyl-4-oxo-4H-quinolizine-8-yl)-pyrrolidin-3-yl]-piperazin-1-ylimino}-methyl)-rifamycin SV

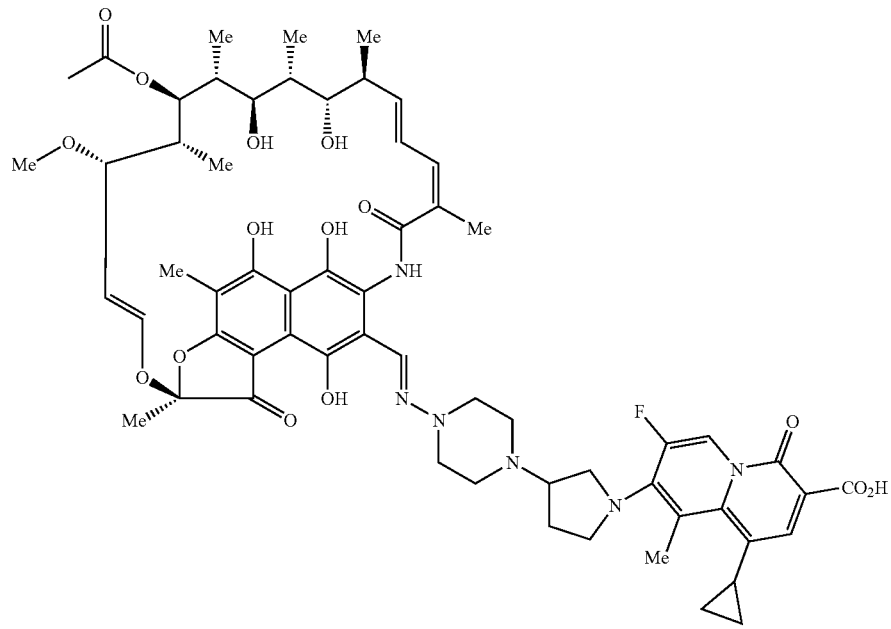

Synthesis: The title compound was prepared by using the same procedure as described in Step 4-5 in Example 30 except (R/S)-1-cyclopropyl-7-fluoro-9-methyl-4-oxo-8-(3-piperazin-1-yl-pyrrolidin-1-yl)-4H-quinolizine-3-carboxylic acid was used in place of 1-cyclopropyl-7-fluoro-9-methyl-4-oxo-8-piperidin-4-yl-4H-quinolizine-3-carboxylic acid (trifluoroacetate salt). ESI MS m/z 1138.3 (M+H$^+$); $^1$H NMR (400 MHz, CDCl$_3$) δ (1:1 mixture of two diastereomers) 13.84 (br s, 1H), 13.46 (brs, 1H), 13.22 (s, 1H), 13.15 (br s, 1H), 12.05 (s, 1H), 9.08 (d, J=10.2 Hz, 1H), 8.30 (s, 1H), 8.24 (s, 1H), 6.62-6.54 (m, 1H), 6.42-6.36 (m, 1H), 6.20 (app d, J=12.5 Hz, 1H), 5.96-5.88 (m, 1H), 5.08 (dd, J=12.5, 7.0 Hz, 1H), 4.92 (d, J=11.0 Hz, 1H), 4.04-3.60 (m, 6H), 3.47 (s, 3H), 3.24-3.05 (m, 3H), 3.03 (s, 3H), 2.80-2.64 (m, 2H), 2.61 (s, 3H), 2.60-1.48 (overlap with 3 Me, m, 13H), 2.22 (s, 3H), 2.05 (two singlets, 3H), 1.78 (s, 3H), 1.30-1.04 (m, 3H), 1.00 (d, J=6.3 Hz, 3H), 0.87 (d, J=7.0 Hz, 3H), 0.72-0.62 (m, 2H), 0.58 (d, J=7.0 Hz, 3H), −0.32 (d, J=6.3 Hz, 3H).

EXAMPLE 43

(S)-3-{[1-(3-Carboxy-1-cyclopropl-7-fluoro-9-methyl-4-oxo-4H-quinolizine-8-yl)-pyrrolidin-3-yloxyimino]-methyl}-rifamycin SV

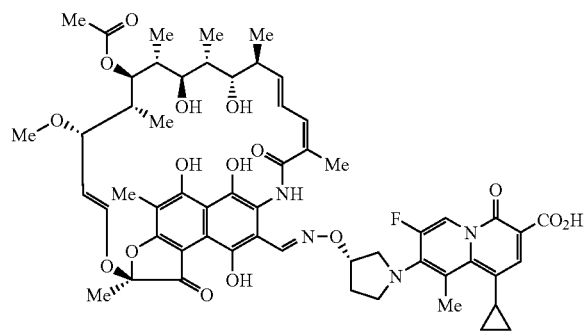

Synthesis: Step 1. (R)-1-Cyclopropyl-7-fluoro-8-(3-hydroxy-pyrrolidin-1-yl)-9-methyl-4-oxo-4H-quinolizine-3-carboxylic acid:

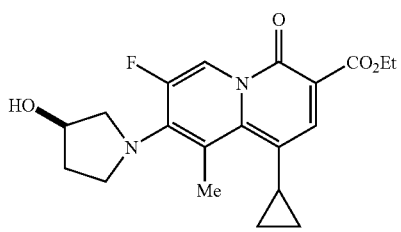

The title compound was prepared by using the same procedure as described in Step 5 in Example 7 except (R)-3-hydroxy pyrrolidine was used in place of 4-pyrrolidin-3-ylmethyl-piperazine-1-carboxylic acid tert-butyl ester. ESI MS m/z: 375.2 (M+H$^+$).

Step 2. (S)-1-Cyclopropyl-8-[3-(1,3-dioxo-1,3-dihydro-isoindol-2-yloxy)-pyrrolidin-1-yl]-7-fluoro-9-methyl-4-oxo-4H-quinolizine-3-carboxylic acid ethyl ester:

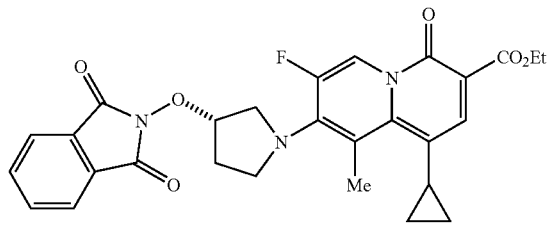

To the solution of the product from step 1 (180 mg, 0.48 mmol), N-hydroxyphthalimide (118 mg, 0.72 mmol) and triphenylphosphine (188 mg, 0.72 mmol) in THF (5.0 mL) was added diisopropyl diazodicarboxylate (0.15 mL, 0.72 mmol) dropwise at 0° C. under nitrogen atmosphere. The reaction mixture was allowed to warm up to room temperature and stirred overnight. The resulting solution was diluted with water and extracted with dichloromethane trice. Combined organic layer was dried over sodium sulfate and concentrated in vacuo. The residue was purified by silica gel column chromatography (40-100% ethyl acetate in hexanes) to provide the title compound (133 mg, 54%) as a yellow solid. ESI MS m/z 520.1 (M+H$^+$).

Step 3. (S)-8-(3-Aminooxy-pyrrolidin-1-yl)-1-cyclopropyl-7-fluoro-9-methyl-4-oxo-4H-quinolizine-3-carboxylic acid ethyl ester:

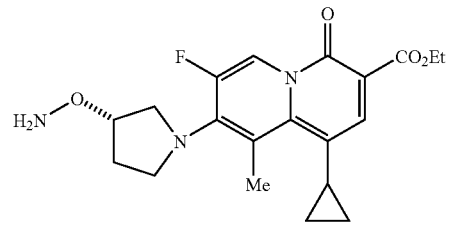

The solution of product from step 2 (70 mg, 0.13 mmol) in ethanol (1.5 mL) was added hydrazine monohydrate (0.13 mL, 2.70 mmol) and heated at 90° C. for 30 minutes under nitrogen atmosphere. The reaction mixture was diluted with dichloromethane. The precipitation was filtered off and rinsed with dichloromethane. The combined filtrate was concentrated in vacuo. The resulting oil was redissolved in small amount of dichloromethane and insoluble solid was filtered off. The filtrate was concentrated again in vacuo to give the title compound as yellow solid (48 mg, 95%), which was used in next step without purification. ESI MS m/z 390.2 (M+H$^+$).

Step 4. (S)-3-{[1-(3-Carboxy-1-cyclopropyl-7-fluoro-9-methyl-4-oxo-4H-quinolizine-8-yl)-pyrrolidin-3-yloxyimino]-methyl}-rifamycin SV: The solution of the product from step 3 (48 mg, 0.12 mmol) in ethanol (2.0 mL) was added the solution of LiOH.H$_2$O (60 mg, 1.43 mmol) in water (1.0 mL). The mixture was heated at 60° C. for one hour and cooled down to room temperature. To the reaction mixture, acetic acid (346 mg, 5.58 mmol) was added followed by 3-formyl rifamycin SV (24 mg, 0.033 mmol). The resulting solution was stirred at room temperature for one hour and partitioned between dichloromethane and water. The separated organic layer was washed with water, brine and dried over sodium sulfate. The solution was concentrated in vacuo and the residue was purified by preparative thin layer chromatography (5% methanol in dichloromethane) to give the title compound as an orange solid (5 mg, 4%). ESI MS m/z 1037.8, 1069.6 (M+H$^+$), 1091.6 (M+Na$^+$). $^1$H NMR (400 MHz, CDCl$_3$) δ 14.16 (br s, 1H), 13.38 (br s, 1H), 12.56 (s, 1H), 11.88 (br s, 1H), 9.38 (d, J=10.2 Hz, 1H), 9.14 (s, 1H), 8.54 (s, 1H), 6.84(dd, J=11.7, 14.1 Hz, 1H), 6.72 (d, J=11.0 Hz, 1H), 6.46 (d, J=12.5 Hz, 1H), 6.28 (dd, J=3.9, 14.9 Hz, 1H), 5.38 (dd, J=6.3, 12.5 Hz, 1H), 5.22 (d, J=11.4 Hz, 1H), 5.20 (m, 1H), 4.45-4.36 (m, 1H), 4.36-4.28 (m, 1H), 4.12-4.04 (m, 2H), 3.94-3.76 (m, 3H), 3.34 (s, 3H), 3.34-3.30 (overlap with Me, m, 1H), 2.93 (s, 3H), 2.78-2.70 (m, 1H), 2.62-1.50 (overlap with 4Me, m, 10H), 2.51 (s, 3H), 2.40 (s, 3H), 2.37 (s, 3H), 2.08 (s, 3H), 1.40-1.30 (overlap with Me, m, 1H), 1.32 (d, J=7.0 Hz, 3H), 1.18 (d, J=6.3 Hz, 3H), 1.12-0.94 (overlap with Me, m, 1H), 0.92 (d, J=7.0 Hz, 3H), 0.01 (d, J=7.0 Hz, 3H).

EXAMPLE 44

(R)-3-{4-[1-(3-Carboxy-1-cyclopropyl-7-fluoro-9-methyl-4-oxo-4H-quinolizine-8-yl)-pyrrolidin-3-yloxyimino]-piperidin-1-yl}-rifamycin S

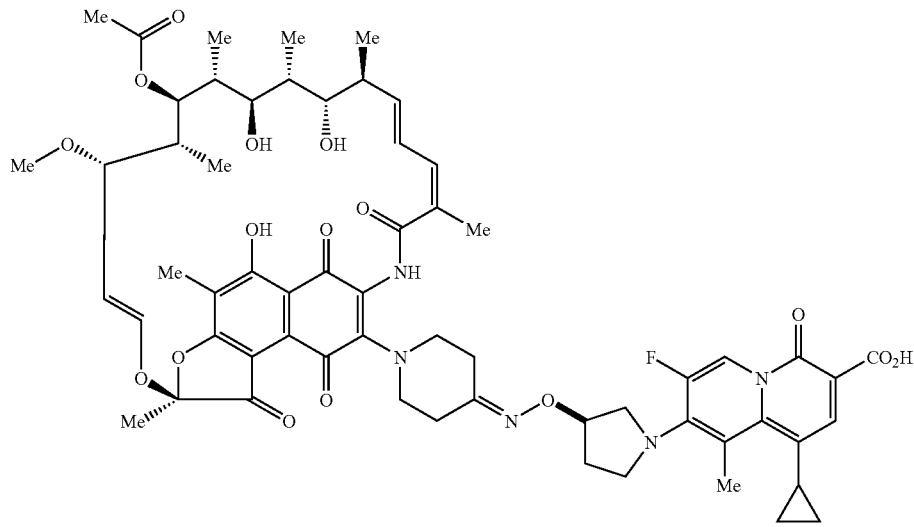

Synthesis: The title compound was prepared by using the same procedures as described for Example 43 except (S)-3-hydroxypyrrolidine hydrochloride salt was used in place of (R)-3-hydroxypyrrolidine hydrochloride salt in Step 1 and 3-(4-oxo-piperidin-1-yl)-rifamycin S was used in place of 3-formyl rifamycin SV in Step 4. The final product was obtained as a greenish solid after purified by preparative thin layer chromatography (10% methanol in dichloromethane). ESI MS m/z 1136.4 (M+H$^+$), 1158.4 (M+Na$^+$). $^1$H NMR (400 MHz, CDCl$_3$) δ 13.92 (s, 1H), 13.15 (s, 1H), 9.12 (d, J=10.2 Hz, 1H), 8.28 (s, 1H), 7.59 (s, 1H), 7.03 (dd, J=11.0, 16.4 Hz, 1H), 6.35 (d, J=11.0 Hz, 1H), 6.19 (d, J=12.5 Hz, 1H), 6.03 (d, J=12.5 Hz, 1H), 5.10 (d, J=9.4 Hz, 1H), 5.07 (dd, J=4.7, 12.5 Hz, 1H), 4.89-4.85 (m, 1H), 4.12-4.06 (m, 2H), 4.02 (d, J=4.7 Hz, 1H), 3.91 (d, J=9.4 Hz, 1H), 3.72-3.56 (m, 4H), 3.50-3.36 (m, 4H), 3.09 (s, 3H), 3.07-3.01 (m, 1H), 2.94-2.86 (m, 1H), 2.64 (s, 3H), 2.56-2.50 (m, 1H), 2.43-2.30 (m, 2H), 2.26 (s, 3H), 2.23-2.16 (m, 1H), 2.13-2.06 (overlap with 2 Me, m, 1H), 2.10 (s, 3H), 2.08 (s, 3H), 1.85-1.78 (m, 2H), 1.74 (s, 3H), 1.69-1.64 (m, 1H), 1.59 (app s, 1H), 1.10-1.04 (m, 1H), 1.02 (d, J=7.0 Hz, 3H), 0.95-0.84 (overlap with Me, m, 2H), 0.84 (d, J=7.0 Hz, 3H), 0.72-0.62 (overlap with Me, m, 2H), 0.68 (d, J=7.0 Hz, 3H), 0.15 (d, J=7.0 Hz, 3H).

EXAMPLE 45

(S)-3-({[1-(3-Carboxy-1-cyclopropyl-7-fluoro-9-methyl-4-oxo-4H-quinolizine-8-yl)-pyrrolidin-3-ylmethyl]-amino}-methyl)-rifamycin S

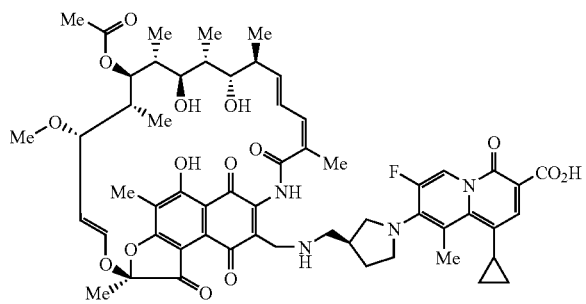

Synthesis: The solution of (S)-8-(3-aminomethyl-pyrrolidin-1-yl)-1-cyclopropyl-7-fluoro-9-methyl-4-oxo-4H-quinolizine-3-carboxylic acid (25 mg, 0.053 mmol) and 3-formylrifamycin SV (50 mg, 0.068 mmol) in methanol (1.0 mL) and acetic acid (0.16 mL) was added sodium acetate (37 mg, 0.46 mmol). The solution was stirred at room temperature for two hours. NaBH$_3$CN (8 mg, 0.12 mmol) was added and the mixture was continuously stirred at room temperature for three hours. The reaction mixture was then partitioned between dichloromethane and water. The separated organic layer was washed with water followed by brine, dried over sodium sulfate and concentrated in vacuo to give the title compound as an orange solid (40 mg, 71%). ESI MS m/z 1069.6 (M+H$^+$).

$^1$H NMR (400 MHz, CDCl$_3$) δ 13.30 (s, 1H), 9.55 (br s, 1H), 9.24 (s, 1H), 9.13 (d, J=10.8 Hz, 1H), 7.72 (s, 1H), 6.86 (dd, J=4.8, 10.8 Hz, 1H), 6.73 (d, J=10.8 Hz, 1H), 6.59 (dd, J=7.2, 14.4 Hz, 1H), 6.42 (d, J=8.4 Hz, 1H), 5.33 (dd, J=6.4, 13.2 Hz, 1H), 5.18 (d, J=9.6 Hz, 1H), 4.88 (d, J=10.8 Hz,

1H), 4.40-4.18 (m, ~7H), 4.02-3.96 (m, 2H), 3.80-3.72 (m, 2H), 3.60-3.50 (m, 1H), 3.33 (s, 3H), 3.03 (s, 3H), 3.02-2.96 (m, 1H), 2.74-2.66 (m, 3H), 2.46 (s, 3H), 2.40-2.00 (overlap with 3 Me, m, 3H), 2.36 (s, 3H), 2.25 (s, 3H), 2.18 (s, 3H), 1.78-1.60 (m, 2H), 1.32 (d, J=6.8 Hz, 3H), 1.17 (d, J=6.0 Hz, 3H), 1.12-1.05 (m, 2H), 0.97-0.88 (m, 2H), 0.87 (d, J=6.8 Hz, 3H), −0.01 (d, J=6.8 Hz, 3H).

EXAMPLE 46

(R)-3-({[1-(3-Carboxy-1-cyclopropyl-7-fluoro-9-methyl-4-oxo-4H-quinolizine-8-yl)-pyrrolidin-3-ylmethyl]-amino}-methyl)-rifamycin S

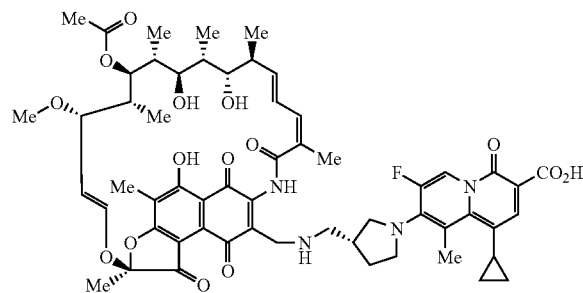

Synthesis: The title compound was prepared by using the same procedure as described for Example 45 except (R)-3-aminomethyl-pyrrolidine-1-carboxylic acid tert-butyl ester was used in place of (S)-3-aminomethyl-pyrrolidine-1-carboxylic acid tert-butyl ester. ESI MS m/z 1069.4 (M+H$^+$). $^1$H NMR (400 MHz, CDCl$_3$) δ 13.30 (s, 1H), 9.55 (br s, 1H), 9.24 (s, 1H), 9.13 (d, J=10.8 Hz, 1H), 7.72 (s, 1H), 6.86 (dd, J=4.8, 10.8 Hz, 1H), 6.73 (d, J=10.8 Hz, 1H), 6.59 (dd, J=7.2, 14.4 Hz, 1H), 6.42 (d, J=8.4 Hz, 1H), 5.33 (dd, J=6.4, 13.2 Hz, 1H), 5.18 (d, J=9.6 Hz, 1H), 4.88 (d, J=10.8 Hz, 1H), 4.40-4.18 (m, ~7H), 4.02-3.96 (m, 2H), 3.80-3.72 (m, 2H), 3.60-3.50 (m, 1H), 3.33 (s, 3H), 3.03 (s, 3H), 3.02-2.96 (m, 1H), 2.74-2.66 (m, 3H), 2.46 (s, 3H), 2.40-2.00 (overlap with 3 Me, m, 3H), 2.36 (s, 3H), 2.25 (s, 3H), 2.18 (s, 3H), 1.78-1.60 (m, 2H), 1.32 (d, J=6.8 Hz, 3H), 1.17 (d, J=6.0 Hz, 3H), 1.12-1.05 (m, 2H), 0.97-0.88 (m, 2H), 0.87 (d, J=6.8 Hz, 3H), −0.01 (d, J=6.8 Hz, 3H).

EXAMPLE 47

(S)-3-[1-(3-Carboxy-1-cyclopropyl-7-fluoro-9-methyl-4-oxo-4H-quinolizine-8-yl)-pyrrolidin-3-yl-aminomethyl]-rifamycin SV

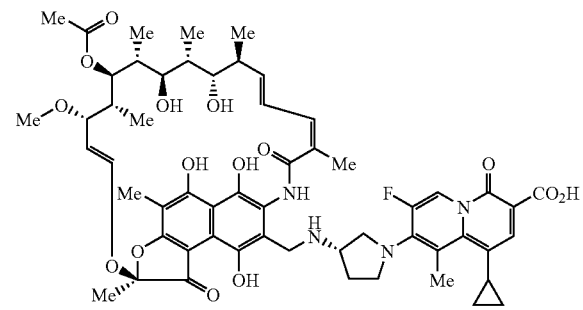

Synthesis: The title compound was prepared by using the similar procedure as described for Example 45 except (S)-3-aminopyrrolidine-1-carboxylic acid tert-butyl ester was used in place of (S)-3-aminomethyl-pyrrolidine-1-carboxylic acid tert-butyl ester. ESI MS m/z 1055.2 (M+H$^+$); $^1$H NMR (400 MHz, CD$_3$OD) δ 8.94 (d, J=9.4 Hz, 1H), 7.89 (s, 1H), 6.66 (dd, J=12.5, 4.7 Hz, 1H), 6.28-6.12 (m, 3H), 4.64-3.80 (m, 6H), 3.76 (d, J=9.9 Hz, 1H), 3.36 (d, J=7.0 Hz, 1H), 3.08 (d, J=10.4 Hz, 1H), 2.98 (s, 3H), 2.72-2.28 (m, 6H), 2.44-2.36 (m, 1H), 2.03 (s, 3H), 1.96-1.76 (m, 3H), 1.92 (s, 3H), 1.75 (s, 3H), 1.47-1.38 (m, 2H), 1.29 (s, 3H), 1.22-0.88 (m, 4H), 0.98 (d, J=7.0 Hz, 3H), 0.93 (d, J=6.3 Hz, 3H), 0.85-0.74 (m, 2H), 0.72-0.60 (m, 2H), 0.65 (d, J=6.3 Hz, 3H), −0.30 (d, J=6.3 Hz, 3H).

EXAMPLE 48

(R/S)-3-{[1-(3-Carboxy-1-cyclopropyl-7-fluoro-9-methyl-4-oxo-4H-quinolizine-8-yl)-pyrrolidin-3-ylamino]-methyl}-rifamycin SV

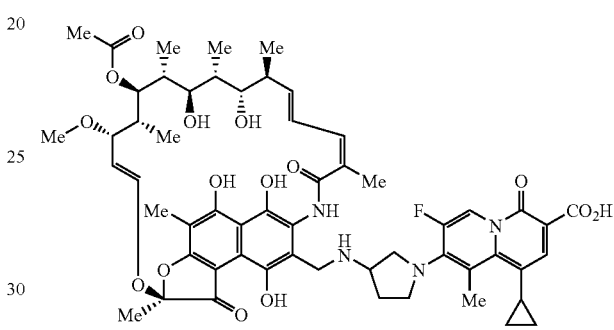

Synthesis: The title compound was prepared by using the similar procedure as described for Example 45 except (R/S)-3-aminopyrrolidine-1-carboxylic acid tert-butyl ester was used in place of (S)-3-aminomethyl-pyrrolidine-1-carboxylic acid tert-butyl ester. ESI MS m/z 1055.2 (M+H$^+$).

EXAMPLE 49

(R/S)-3-({[1-(3-Carboxy-1-cyclopropyl-7-fluoro-9-methyl-4-oxo-4H-quinolizine-8-yl)-pyrrolidin-3-yl]-methyl-amino}-methyl)-rifamycin SV

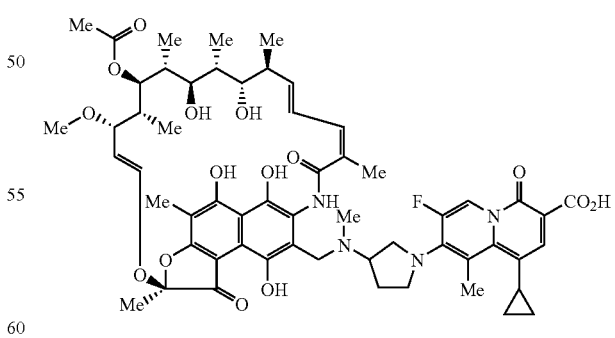

Synthesis: The title compound was prepared by using the same procedure as described for Example 45 except (R/S)-3-methylaminopyrrolidine-1-carboxylic acid tert-butyl ester was used in place of (S)-3-aminomethyl-pyrrolidine-1-carboxylic acid tert-butyl ester. ESI MS m/z 1069.2 (M+H$^+$).

EXAMPLE 50

3-[2-(3-Carboxy-1-cyclopropyl-7-fluoro-9-methyl-4-oxo-4H-quinolizine-8-yl)-2,8-diaza-spiro[4.5]dec-8-ylmethyl]-rifamycin SV

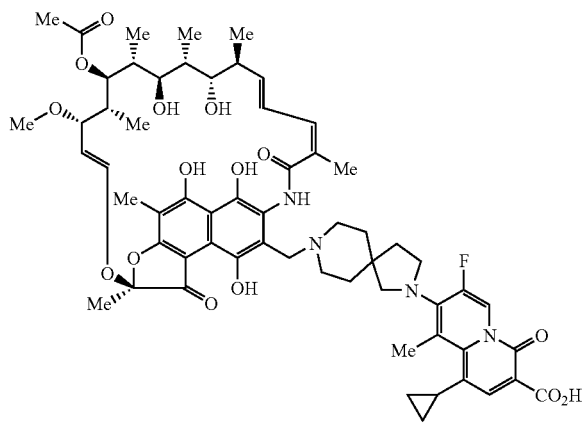

Step 1. 4-Methoxycarbonylmethylene-piperidine-1-carboxylic acid tert-butyl ester:

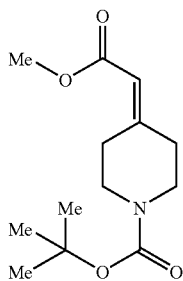

To a solution of 4-oxo-piperidine-1-carboxylic acid tert-butyl ester (5 g, 25.1 mmol) in toluene (50 mL) was added methyl(triphenylphosphoranylidene)acetate (10.5 g, 31.4 mmol) at room temperature and the mixture was refluxed overnight. The reaction mixture was cooled to room temperature and filtered through a short pad of silica gel column (20% ethyl acetate in hexane). The filtrate was evaporated in vacuo to give a white solid (6.2 g, 97%). $^1$H NMR (400 MHz, CDCl$_3$) δ 5.72 (s, 1H), 3.69 (s, 3H), 3.52-3.46 (m, 4H), 2.93 (br, t, J=6.4 Hz, 2H), 2.28 (br t, J=6.0 Hz, 2H), 1.47 (s, 9H).

Step 2. 4-Methoxycarbonylmethyl-4-nitromethyl-piperidine-1-carboxylic acid tert-butyl ester:

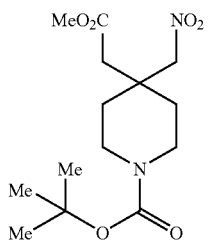

To a solution of 4-methoxycarbonylmethylene-piperidine-1-carboxylic acid tert-butyl ester (6.2 g, 24.3 mmol) in nitromethane (225 mL) was added tetramethylguanidine (1.2 mL, 9.6 mmol) at room temperature and the mixture was refluxed for one day. The reaction mixture was cooled to room temperature and diluted with ethyl acetate and washed with 2 N aq HCl twice. The organic layer was washed with brine and dried over anhydrous MgSO$_4$. The solution was evaporated in vacuo and the residue was purified with silica gel column chromatography (10% ethyl acetate/hexanes) to give the desired product (3.2 g, 42%). $^1$H NMR (400 MHz, CDCl$_3$) δ 4.73 (br s, 2H), 3.70 (s, 3H), 3.54-3.48 (m, 2H), 3.42-3.35 (m, 2H), 2.59 (s, 2H), 1.65-1.62 (m, 4H), 1.44 (s, 9H).

Step 3. 3-Oxo-2,8-diaza-spiro[4.5]decane-8-carboxylic acid tert-butyl ester:

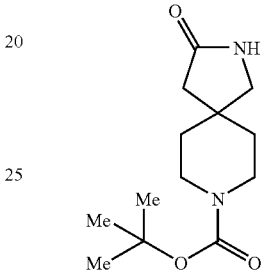

To a solution of 4-methoxycarbonylmethyl-4-nitromethyl-piperidine-1-carboxylic acid tert-butyl ester (1.0 g, 3.2 mmol) in ethanol (10 mL) was added Raney Ni (1 g). The resulting suspension was hydrogenated at 1 atm overnight. The mixture was filtered through Celite and evaporated in vacuo. The residue was purified with silica gel column chromatography (10% methanol in dichloromethane) to give the desired lactam (694 mg, 86%). $^1$H NMR (400 MHz, CD$_3$OD) δ 3.54-3.48 (m, 2H), 3.37-3.32 (m, 2H), 3.23 (s, 2H), 2.26 (s, 2H), 1.62-1.59 (m, 4H), 1.45 (s, 9H).

Step 4. 2,8-Diaza-spiro[4.5]decane-8-carboxylic acid tert-butyl ester:

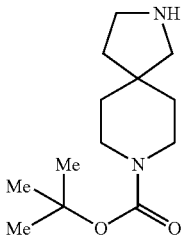

To a solution of 3-oxo-2,8-diaza-spiro[4.5]decane-8-carboxylic acid tert-butyl ester (3 g, 11.8 mmol) in THF (65 mL) was added BH$_3$.THF (1 N in THF, 35 mL) at 0° C. and stirred for 5 minutes. The reaction mixture was heated to reflux overnight and then cooled to 0° C. The mixture was quenched with methanol (30 mL) and evaporated in vacuo. The residue was dissolved in THF (50 mL) and 1 N aq HCl (50 mL) was added to it. The mixture was stirred at room temperature for one hour, cooled to 0° C. and basified with 3 N aq NaOH. The aqueous phase was extracted with dichloromethane twice. The combined organic layer was dried over MgSO$_4$, filtered and evaporated under reduced pressure to give the desired amine (2.8 g, 100%), which was used for next step without further purification. $^1$H NMR (400 MHz, CD$_3$OD) δ 3.48-3.35 (m, 4H), 3.06 (t, J=6.8 Hz, 2H), 2.80 (s, 2H), 1.73 (t, J=6.8 Hz, 2H), 1.53-1.50 (m, 4H), 1.44 (s, 9H).

Step 5. 8-(8-tert-Butoxycarbonyl-2,8-diaza-spiro[4.5] dec-2-yl)-1-cyclopropyl-7-fluoro-9-methyl-4-oxo-4H-quinolizine-3-carboxylic acid ethyl ester:

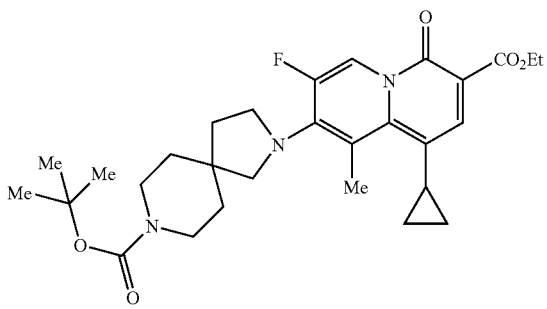

To a solution of 2,8-diaza-spiro[4.5]decane-8-carboxylic acid tert-butyl ester (150 mg, 0.6 mmol) in acetonitrile (5.0 mL) were added 8-chloro-1-cyclopropyl-7-fluoro-9-methyl-4-oxo-4H-quinolizine-3-carboxylic acid ethyl ester (160 mg, 0.5 mmol) and NaHCO$_3$ (300 mg, 3.6 mmol) and the mixture was refluxed overnight. The reaction mixture was cooled to 0° C., quenched with 0.5 N aq HCl (5 mL) and partitioned between dichloromethane and water. The combined organic layer was dried over anhydrous MgSO$_4$ and evaporated under reduced pressure. The residue was purified with preparative thin layer chromatography (50% ethyl acetate in hexanes) to give the desired product (150 mg, 47%) as a yellow solid. ESI MS m/z 528 (M+H$^+$); $^1$H NMR (400 MHz, CDCl$_3$) δ 9.25 (d, J=10.8 Hz, 1H), 8.18 (s, 1H), 4.38 (q, J=7.6 Hz, 2H), 3.77-3.72 (m, 2H), 3.53-3.51 (m, 2H), 3.49-3.43 (m, 4H), 2.58 (s, 3H), 2.18-2.14 (m, 1H), 1.91 (t, J=7.2 Hz, 2H), 1.64-1.61 (m, 4H), 1.45 (s, 9H), 1.42 (t, J=7.6 Hz, 3H), 0.96-0.91 (m, 2H), 0.62-0.58 (m, 2H).

Step 6. 1-Cyclopropyl-8-(2,8-diaza-spiro[4.5]dec-2-yl)-7-fluoro-9-methyl-4-oxo-4H-quinolizine-3-carboxylic acid:

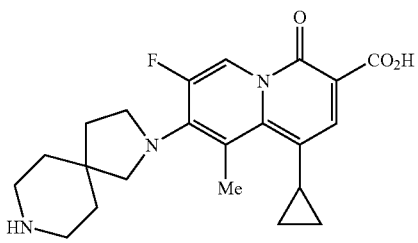

To a solution of 8-(8-tert-butoxycarbonyl-2,8-diaza-spiro [4.5]dec-2-yl)-1-cyclopropyl-7-fluoro-9-methyl-4-oxo-4H-quinolizine-3-carboxylic acid ethyl ester (120 mg, 0.2 mmol) in ethanol (6.0 mL) and water (3.0 mL) was added LiOH.H$_2$O (84 mg, 2 mmol) and refluxed for one hour. The reaction mixture was cooled to 0° C. and quenched with 0.5 N aq HCl (15 mL). The solution was diluted with water and extracted with dichloromethane trice. The combined organic layer was dried over anhydrous MgSO$_4$ and evaporated under reduced pressure. The residue was dissolved in dichloromethane (2.0 mL) and trifluoroacetic acid (2.0 mL) was added to it. The mixture was stirred for one hour and evaporated under reduced pressure. The residue was purified by preparative thin layer chromatography (dichloromethane: methanol:acetic acid=140:20:0.3) to give the desired product (80 mg, 78%) as a yellow solid. ESI MS m/z 528 (M+H$^+$); $^1$H NMR (400 MHz, CDCl$_3$+CD$_3$OD) δ 8.95 (d, J=10.4 Hz, 1H), 8.03 (s, 1H), 3.73-3.70 (m, 2H), 3.57 (br s, 2H), 3.12 (m, 4H), 2.53 (s, 3H), 2.12 (m, 3H), 1.95-1.91 (m, 2H), 1.83-1.76 (m, 2H), 0.92 (brd, J=7.2 Hz, 2H), 0.56 (brd, J=4.4 Hz, 2H).

Step 7. 3-[2-(3-Carboxy-1-cyclopropyl-7-fluoro-9-methyl-4-oxo-4H-quinolizine-8-yl)-2,8-diaza-spiro[4.5]dec-8-ylmethyl]-rifamycin SV: To a solution of the product from step 6 (25 mg, 0.05 mmol) in DMSO (1.0 mL) were added 3-formyl-rifamycin SV (36 mg, 0.05 mmol), NaOAc (41 mg, 0.5 mmol) and acetic acid (0.02 mL, 0.3 mmol) and stirred for one hours, followed by the addition of sodium triacetoxyborohydride (32 mg, 0.15 mmol) and stirred for two days at room temperature. The reaction mixture was diluted with 20% isopropyl alcohol in dichloromethane and washed with water. The organic layer was dried over anhydrous Na$_2$SO$_4$ and evaporated under reduced pressure. The residue was purified with preparative thin layer chromatography (dichloromethane:methanol:acetic acid=100:10:0.3) to give the desired product (10 mg, 18%) as a brownish yellow solid. ESI MS m/z 1109 (M+H$^+$); $^1$H NMR (400 MHz, CDCl$_3$) δ 12.9 (br s, 1H), 9.06 (d, J=10.8 Hz, 1H), 9.01 (s, 1H), 8.98 (s, 1H), 8.20 (s, 1H), 6.49-6.17 (m, 3H), 5.12-4.94 (m, 3H), 3.92-3.41 (m, 14H), 3.03 (s, 3H), 2.64 (s, 3H), 2.41 (m, 2H), 2.19-1.83 (m, 9H), 2.13 (s, 3H), 2.07 (s, 3H), 2.05 (s, 3H), 1.78 (s, 3H), 1.02 (d, J=6.8 Hz, 3H), 0.89-0.85 (m, 2H), 0.86 (d, J=6.8 Hz, 3H), 0.14 (d, J=14.4 Hz, 2H), −0.27 (d, J=6.8 Hz, 3H).

REFERENCES CITED

The content of each of the following documents is hereby incorporated by reference.

Patent Documents

U.S. Pat. No. 5,786,350.
International Patent Application No. WO 03/045319 A2
International Patent Application No. WO 94/280002

Other Publications

Farr, B. M. Rifamycins, in *Principles and Practice of Infectious Diseases*; Mandell, G. L., Bennett, J. E., Dolin, R., Eds.; Churchhill Livingstone: Philadelphia, pp. 348-361.
Li, Q.; Chu, D. T. W.; et al. *J. Med. Chem.* Vol. 39, pp. 3070-3088, 1996.
Li, Q.; Mitscher, L. A.; Shen, L. *Med. Res. Rev.* Vol. 20, pp. 231-293, 2000.
Marsili, L.; Pasqualucci, C. R.; et al. *J. Antibiot.* Vol. 34, pp. 1033-1038, 1981.
National Committee for Clinical Laboratory Standards, 2000, Methods for dilution antimicrobial susceptibility tests for bacteria that grow aerobically, 5th ed. M7-A5, Wayne, Pa.
Yamane, T.; Hashizumi, T.; et al. *Chem. Pharm Bull.* Vol. 41, pp. 148-155, 1993.

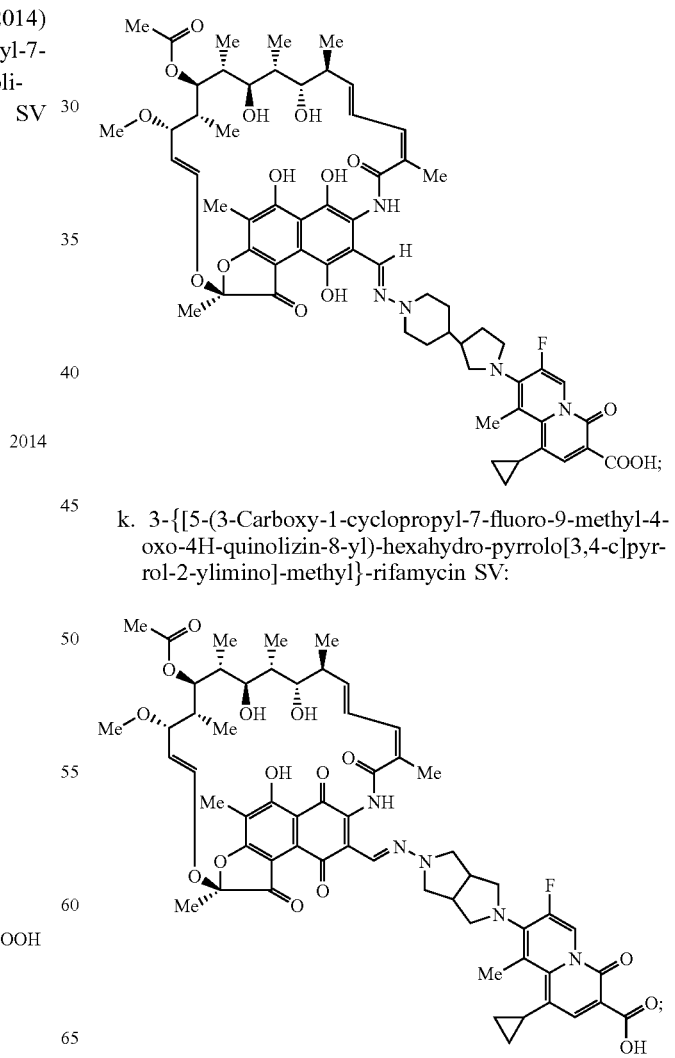

l. (R/S, R/S)-3-({3 -[1-(3-Carboxy-1-cyclopropyl-7-fluoro-9-methyl-4-oxo-4H-quinolizine-8-yl)-piperidin-3-yl]-pyrrolidin-1-ylimino}-methyl)-rifamycin SV:
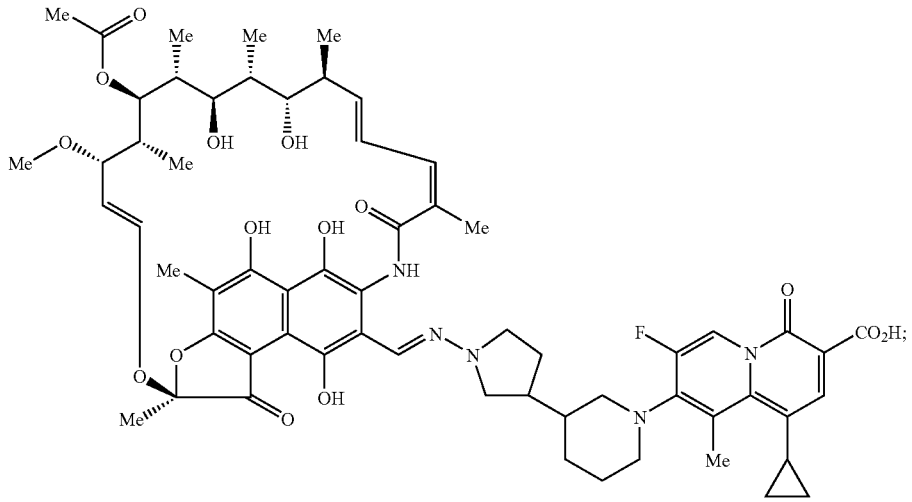
m. (R/S)-3-({4-[1-(3-Carboxy-1-cyclopropyl-7-fluoro-9-methyl-4-oxo-4H-quinolizine-8-yl)-pyrrolidin-3-yl]-piperazin-1-ylimino}-methyl)-rifamycin SV:
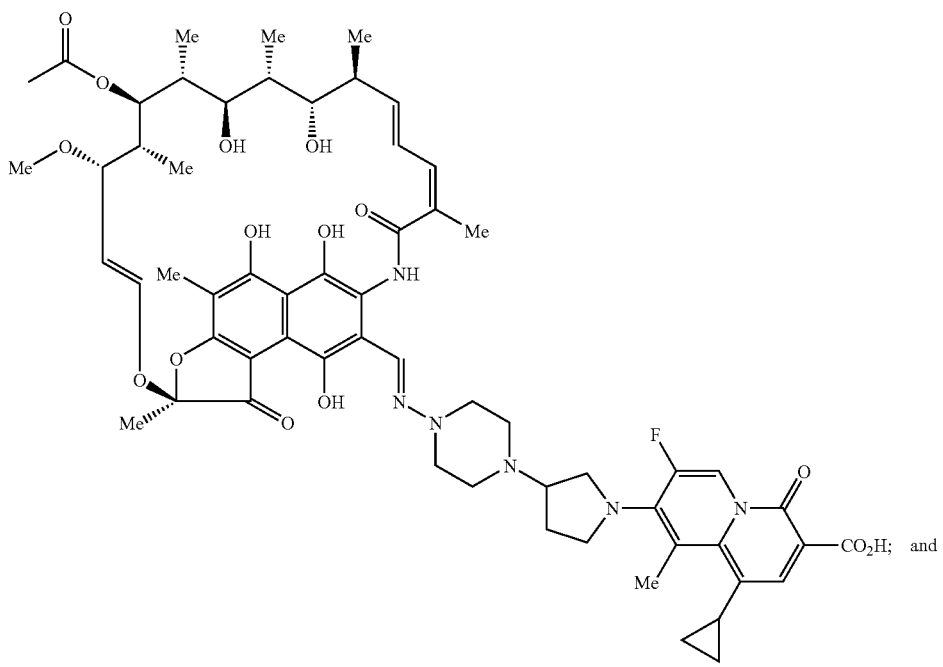
and n. (S)-3-{[1-(3-Carboxy-1-cyclopropl-7-fluoro-9-methyl-4-oxo-4H-quinolizine-8-yl)-pyrrolidin-3-yloxyimino]-methyl}-rifamycin SV:
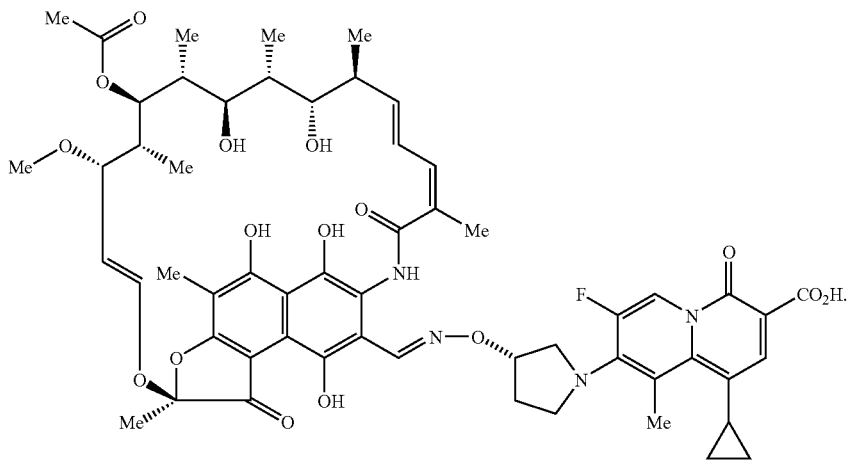
8. A compound having a formula selected from the group consisting of:
   a. (S)-3-({[1-(3-Carboxy-1-cyclopropyl-7-fluoro-9-methyl-4-oxo-4H-quinolizine-8-yl)-pyrrolidin-3-ylmethyl]-amino}-methyl)-rifamycin S:
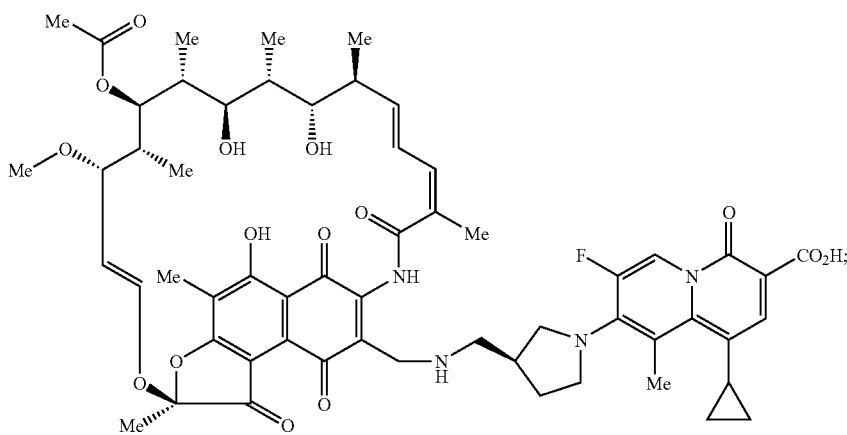

b. (R)-3-({[1-(3-Carboxy-1-cyclopropyl-7-fluoro-9-methyl-4-oxo-4H-quinolizine-8-yl)-pyrrolidin-3-yl-methyl]-amino}-methyl)-rifamycin S:
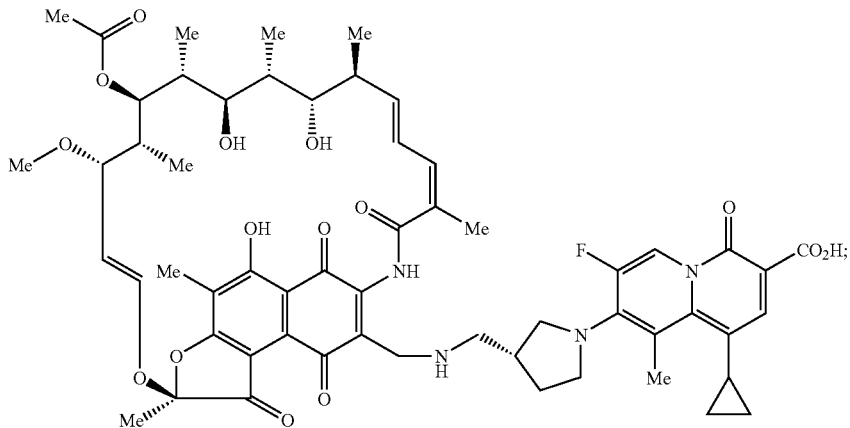
c. (S)-3-[1-(3-Carboxy-1-cyclopropyl-7-fluoro-9-methyl-4-oxo-4H-quinolizine-8-yl)-pyrrolidin-3-yl-aminomethyl]-rifamycin SV:
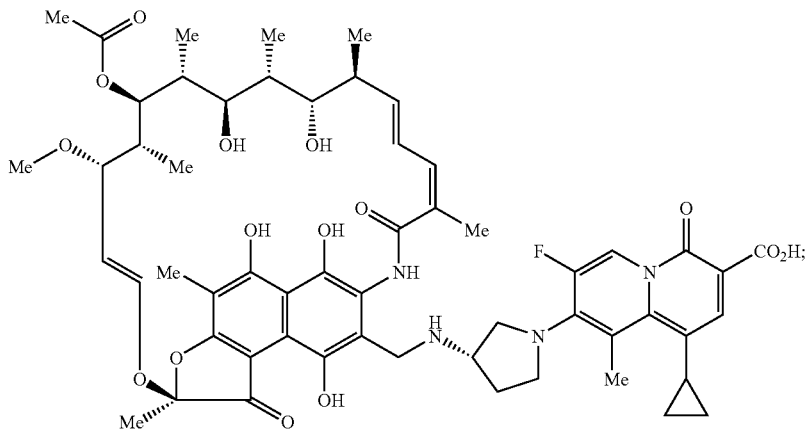
d. (R/S)-3-{[1-(3-Carboxy-1-cyclopropyl-7-fluoro-9-methyl-4-oxo-4H-quinolizine-8-yl)-pyrrolidin-3-ylamino]-methyl}-rifamycin SV:
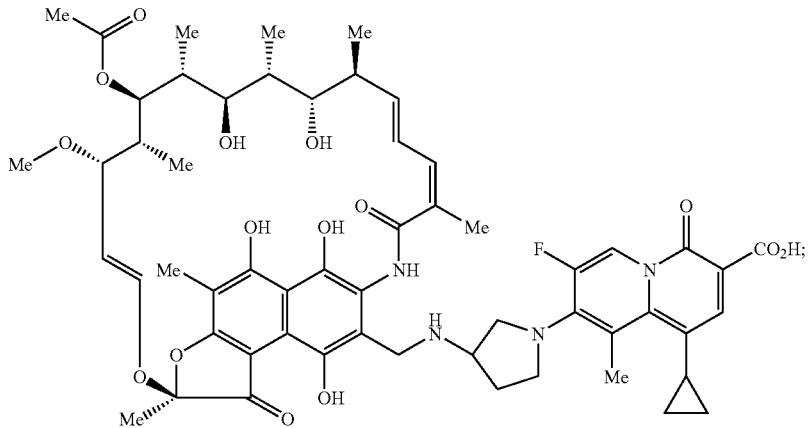

e. (R/S)-3-({[1-(3-Carboxy-1-cyclopropyl-7-fluoro-9-methyl-4-oxo-4-H-quinolizine-8-yl)-pyrrolidin-3-yl]-methyl-amino}-methyl)-rifamycin SV:
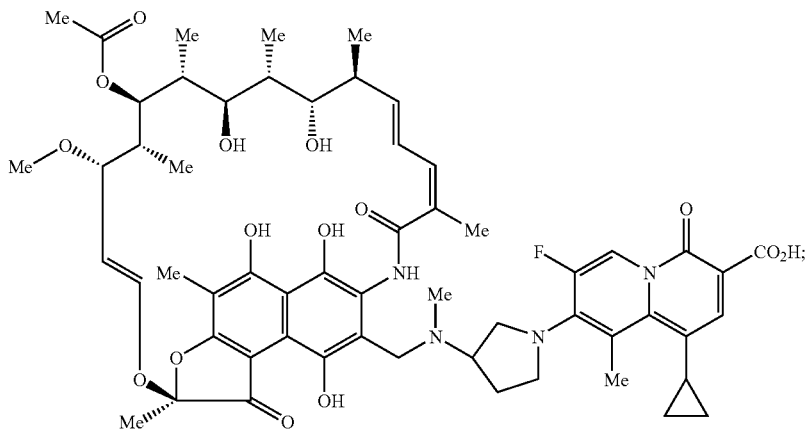
f. (S)-3-({[1-(3-Carboxy-1-cyclopropyl-7-fluoro-9-methyl-4-oxo-4H-quinolizine-8-yl)-pyrrolidin-3-ylmethyl]-amino}-methyl)-rifamycin SV:
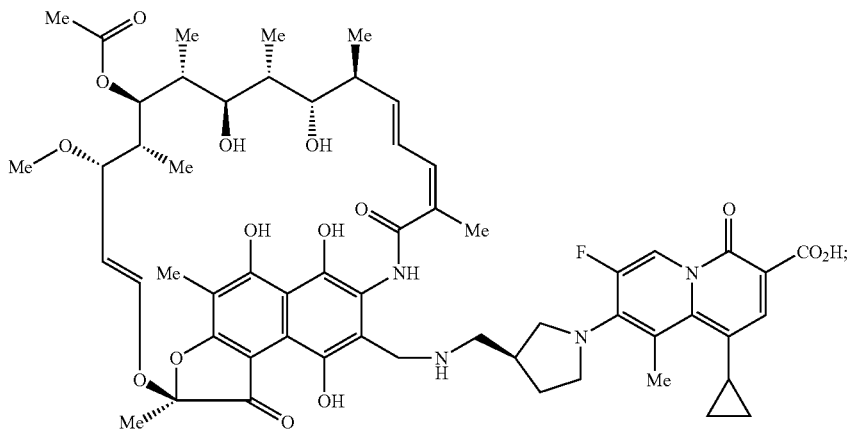
g. (R)-3-({[1-(3-Carboxy-1-cyclopropyl-7-fluoro-9-methyl-4-oxo-4-H-quinolizine-8-yl)-pyrrolidin-3-ylmethyl]-amino}-methyl)-rifamycin SV:
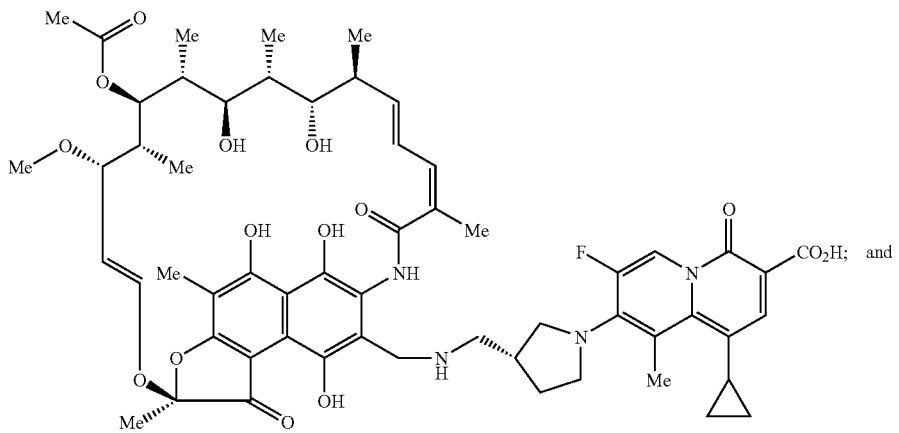

h. 3-[2-(3-Carboxy-1-cyclopropyl-7-fluoro-9-methyl-4-oxo-4H-quinolizine-8-yl)-2,8-diaza-spiro[4.5]dec-8-ylmethyl]-rifamycin SV:
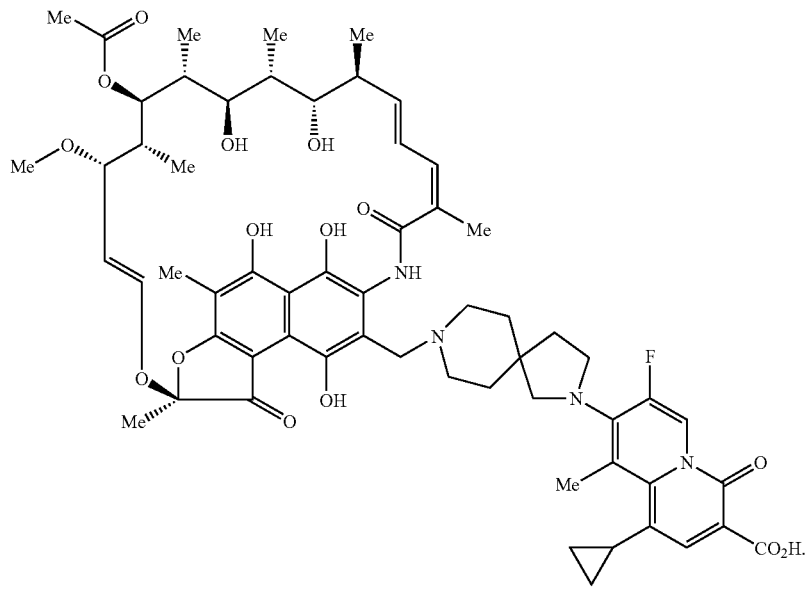

What is claimed is:

1. A compound having a structural formula I:

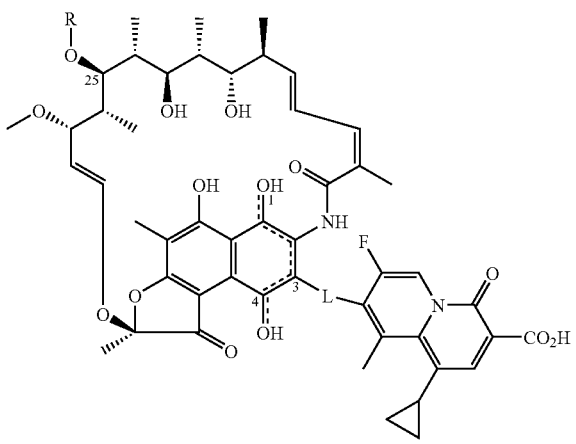

a pharmaceutically acceptable salt thereof, wherein:
R is hydrogen or acetyl,
L is a linker selected from one or any combination of two or three of the following:
(a) $(C_1-C_6)$alkylene,
(b) $(C_3-C_8)$cycloalkylene,
(c) arylene,
(d) heteroarylene,
(e) bivalent heterocyclic group containing 1 to 3 heteroatoms,
(f) —(=O)—,
(g) —C(=N—O—$R_{11}$)—, wherein $R_{11}$ represents hydrogen, $(C_1-C_6)$alkyl, or substituted $(C_1-C_6$alkyl),
(h) —C=N—,
(i) —O—,
(j) —S(O)$_n$—, wherein n is number between 0 and 2, and
(k) —N($R_{12}$)—, wherein $R_{12}$ represents hydrogen, $(C_1-C_6)$alkyl. or substituted $(C_1-C_6$ alkyl),
wherein the carbon or nitrogen atoms of the linker group are substituted by 0 to 3 substituents selected from $(C_1-C_6)$alkyl, substituted $(C_1-C_6)$alkyl, heterocycloalkyl, amino, $(C_1-C_6)$alkylamino, di$(C_1-C_6)$alkylamino. hydroxyl, or $(C_1-C_6)$alkoxy; and provided L is not

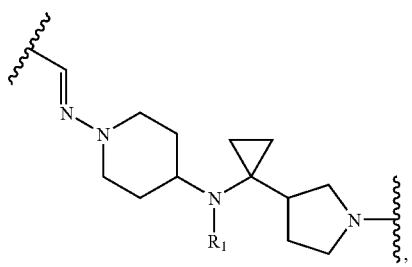

wherein $R_1$ is H, $C_1-C_6$)alkyl, or substituted $(C_1-C_6)$alkyl.

2. The compound of claim 1, wherein L is a linker group selected from one or any combination of two to three of the following structural elements:

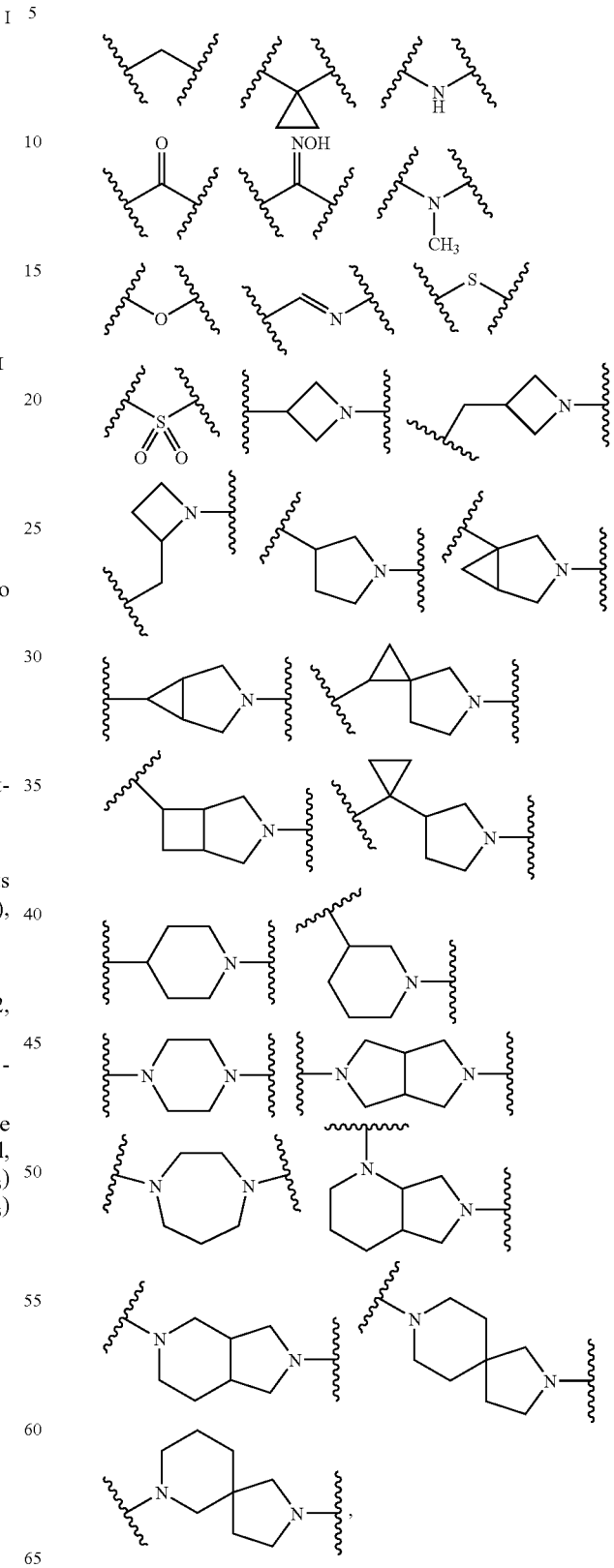

3. A method of treating a bacterial infection in a subject comprising administering to the subject an effective amount of the compound of claim 1.

4. The method of claim 3, wherein the bacterial infection is caused by a drug-resistant bacterium.

5. A compound having a formula selected from the group consisting of:

a. (R/&)-3-{[1-(3-Carboxy-1-cyclopropyl-7-fluoro-9-methyl-4-oxo-4H-quinolizine-8-yl)-pyrrolidin-3-ylmethyl]-amino}-rifamycin S:

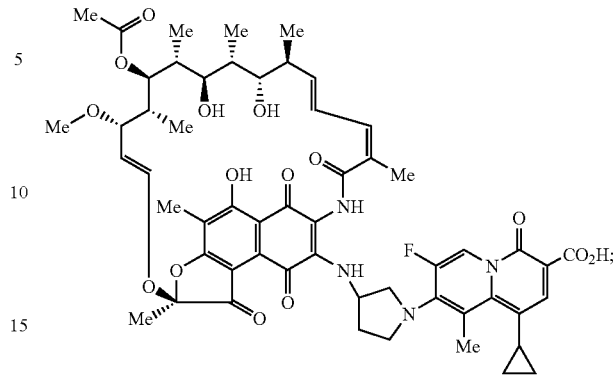

b. (R/S)-3-{[1-(3-Carboxy-1-cyclopropyl-7-fluoro-9-methyl-4-oxo-4H-quinolizine-8-yl)-pyrrolidin-3-yl]-amino}-rifamycin S:

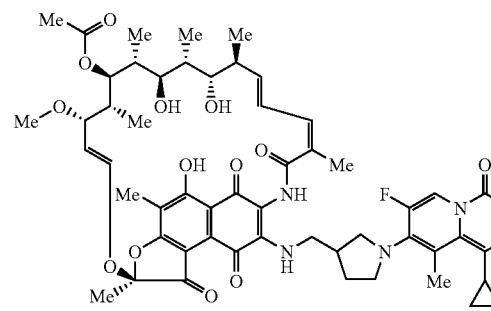

c. (R/S)-3-{[1-(3-Carboxy-1-cyclopropyl-7-fluoro-9-methyl-4-oxo-4H-quinolizine-8-yl)-pyrrolidin-3-yl]-methyl-amino}-rifamycin S:

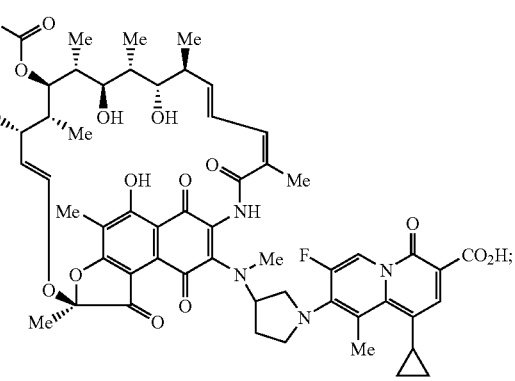

d. (R/S)-3-{4-[1-(3-Carboxy-1-cyclopropyl-7-fluoro-9-methyl-4-oxo-4H-quinolizine-8-yl)-pyrrolidin-3-ylmethyl]-piperazin-1-yl}-rifamycin S:

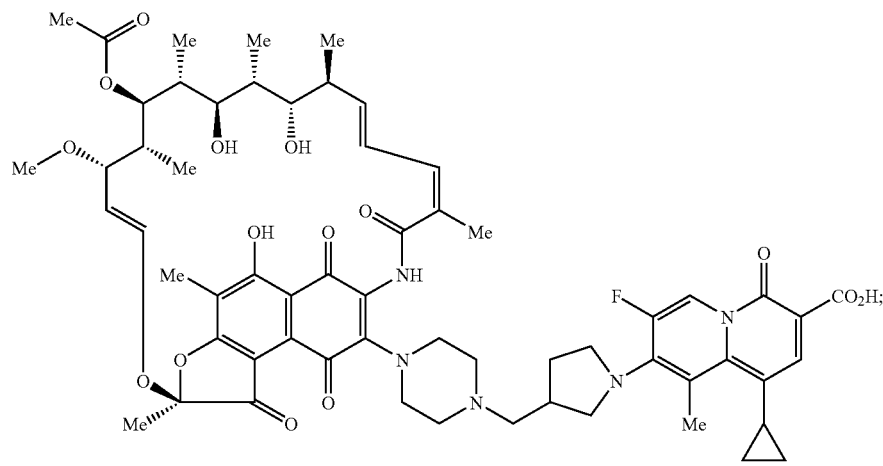

e. (S)-3-{4-[1-(3-Carboxy-1-cyclopropyl-7-fluoro-9-methyl-4-oxo-4H-quinolizine-8-yl)-pyrrolidin-3-yl-oxy-carbonyl]-piperazin-1-yl}-rifamycin S:
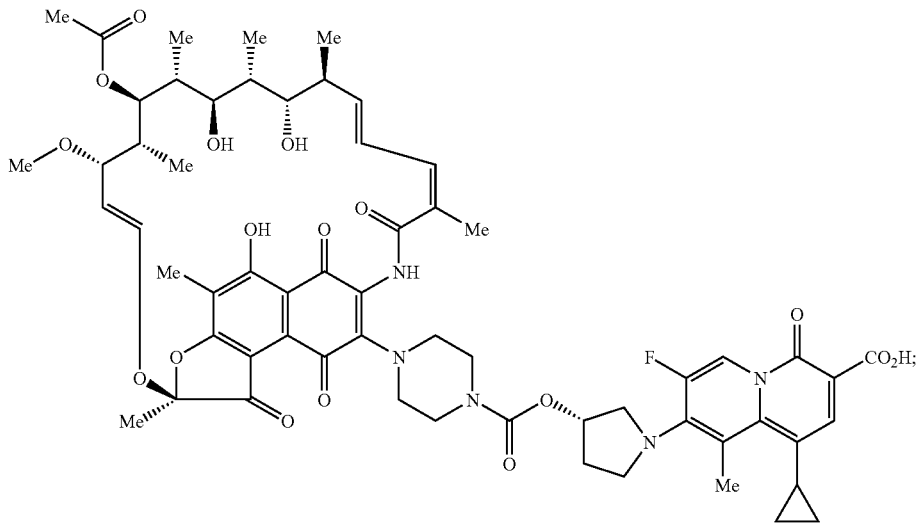
f. (R/S)-3-4-{[1-(3-Carboxy-1-cyclopropyl-7-fluoro-9-methyl-4-oxo-4H-quinolizine-8-yl)-pyrrolidin-3-yl-carbonyl]-amino}-piperidin-1-yl)-rifamycin S:
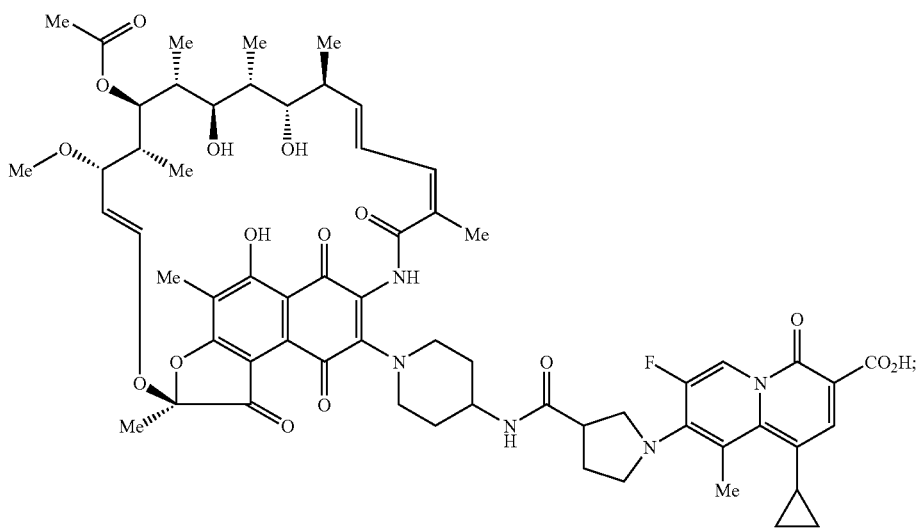

g. (S)-3-(4-{[1-(3-Carboxy-1-cyclopropyl-7-fluoro-9-methyl-4-oxo-4H-quinolizine-8-yl)-pyrrolidin-3-yl]-carbamoyl}-piperidin-1-yl)-rifamycin S:
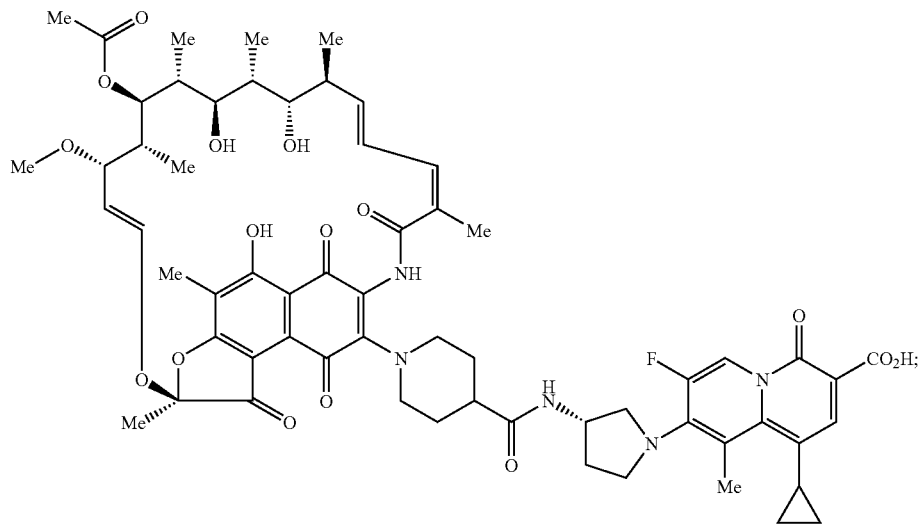
h. (R/S)-3-(4-{[1-(3-Carboxy-1-cyclopropyl-7-fluoro-9-methyl-4-oxo-4H-quinolizine-8-yl)-pyrrolidin-3-ylmethyl]-carbamoyl}-piperidin-1-yl)-rifamycin S:
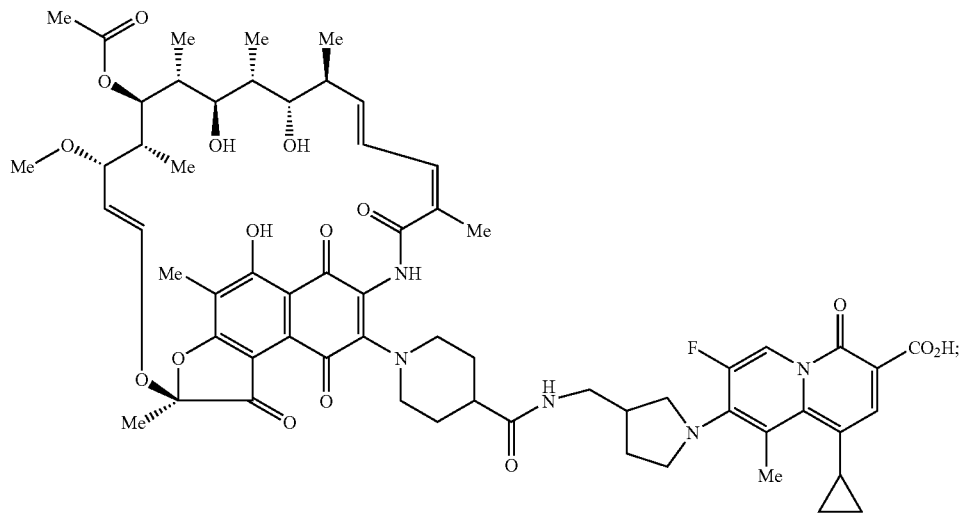

i. (R/S)-3-{4-[1-(3-Carboxy-1-cyclopropyl-7-fluoro-9-methyl-4-oxo-4H-quinolizine-8-yl)-pyrrolidin-3-yl]-piperidin-1-yl}-rifamycin S:

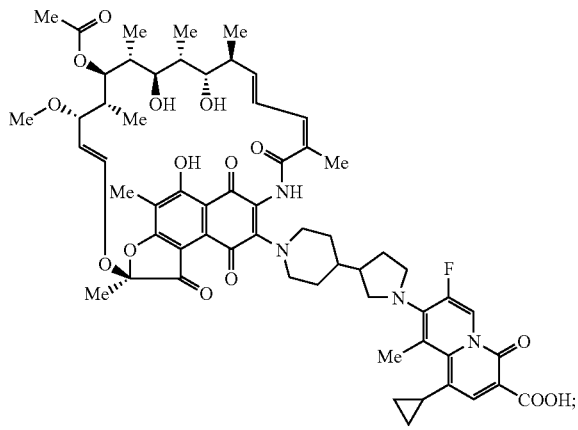

j. 3-[5-(3-Carboxy-1-cyclopropyl-7-fluoro-9-methyl-4-oxo-4H-quinolizin-8-yl)-hexahydro-pyrrolo[3,4-c]pyrrol-2-yl]-rifamycin S:

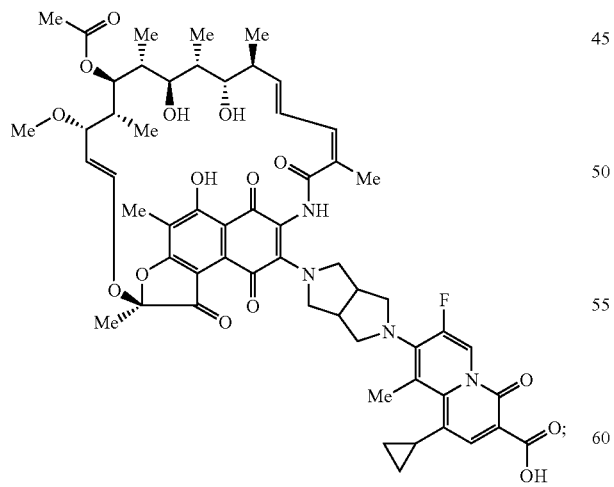

k. 3-[7-(3-Carboxy-1-cyclopropyl-7-fluoro-9-methyl-4-oxo-4H-quinolizin-8-yl)-2,7-diaza-spiro[4.4]non-2-yl]-rifamycin S:

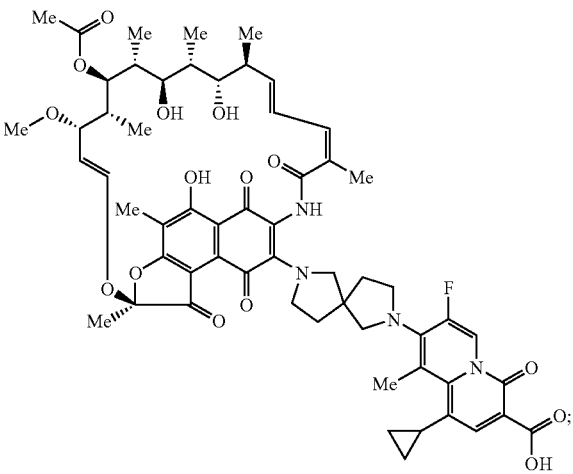

l. (R/S,R/S)-3-{3-[1-(3-Carboxy-1-cyclopropyl-7-fluoro-9-methyl-4-oxo-4H-quinolizine-8-yl)-piperidin-3-yl]-pyrrolidin-1-yl}-rifamycin S:

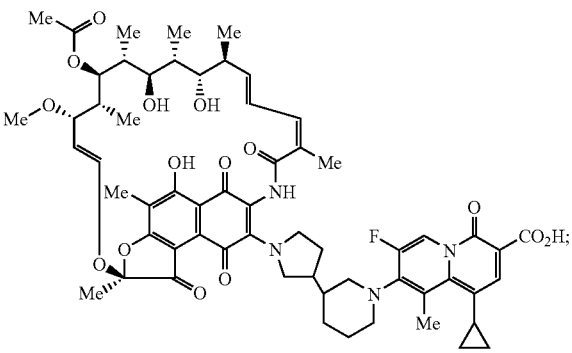

m. (R/S)-3-{3-[4-(3-Carboxy-1-cyclopropyl-7-fluoro-9-methyl-4-oxo-4H-quinolizin-8-yl)-piperazin-1-yl]-pyrrolidin-1-yl}-rifamycin S:
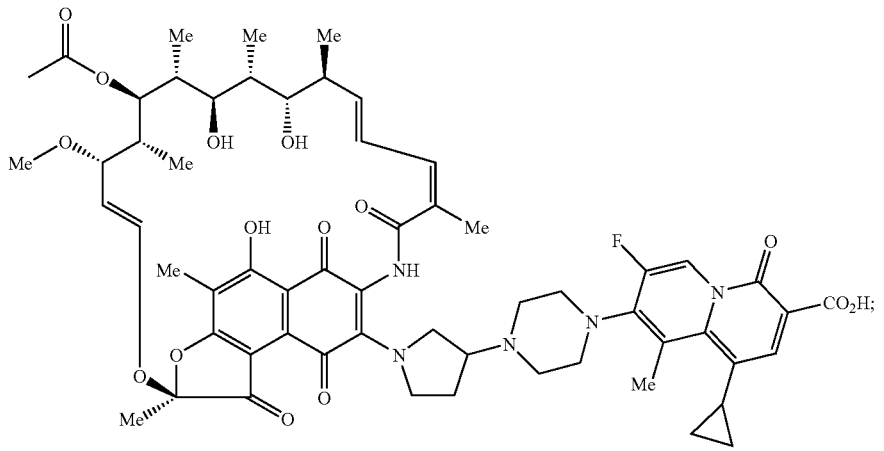
n. (R/S, R/S)-3-{3-[1-(3-Carboxy-1-cyclopropyl-7-fluoro-9-methyl-4-oxo-4H-quinolizine-8-yl)-piperidin-3-ylamino]-pyrrolidin-1-yl}-rifamycin S:
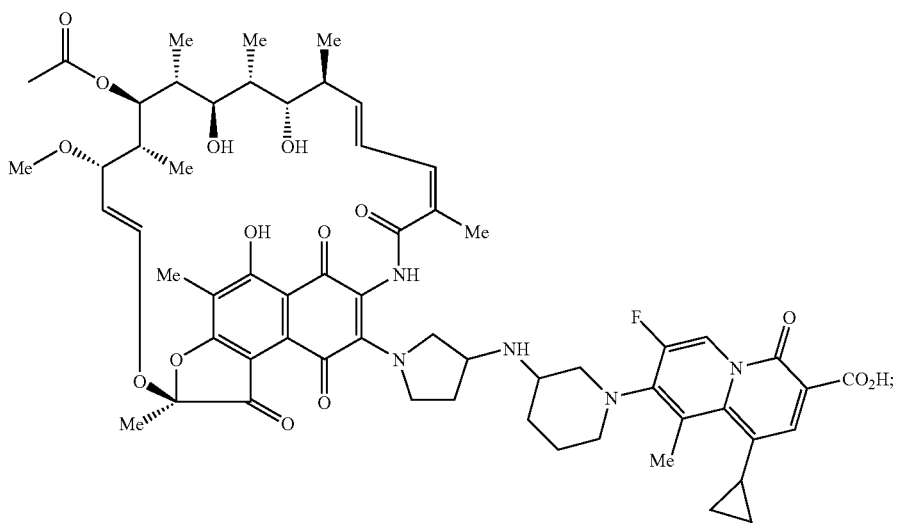

o. (R, S)-3-{3-[1-(3-Carboxy-1-cyclopropyl-7-fluoro-9-methyl-4-oxo-4H-quinolizin-8-yl)-pyrrolidin-3-ylamino]-pyrrolidin-1-yl}-rifamycin S and (S, S)-3-{3-[1-(3-Carboxy-1-cyclopropyl-7-fluoro-9-methyl-4-oxo-4H-quinolizin-8-yl)-pyrrolidin-3-ylamino]-pyrrolidin-1-yl}-rifamycin S:
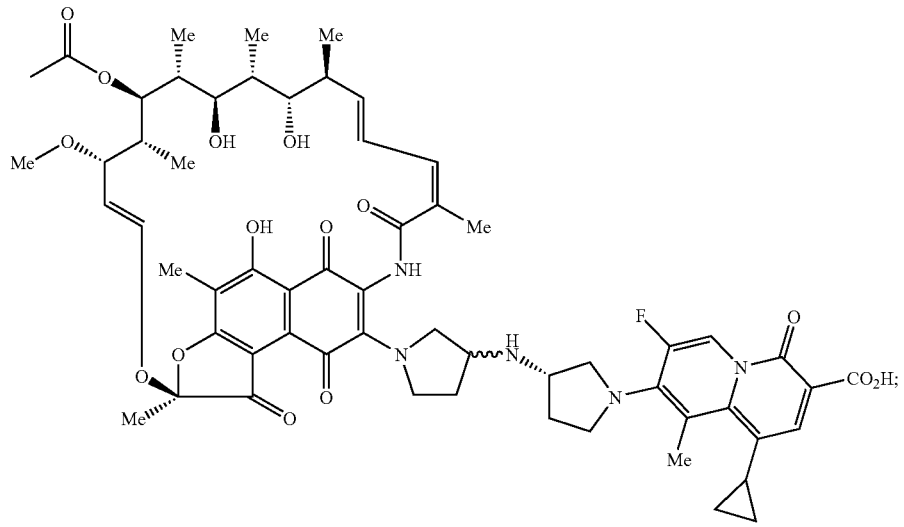
p. (R/S)-3-{4-[1-(3-Carboxy-1-cyclopropyl-7-fluoro-9-methyl-4-oxo-4H-quinolizin-8-yl)-pyrrolidin-3-yl]-piperazin-1-yl}-rifamycin S:
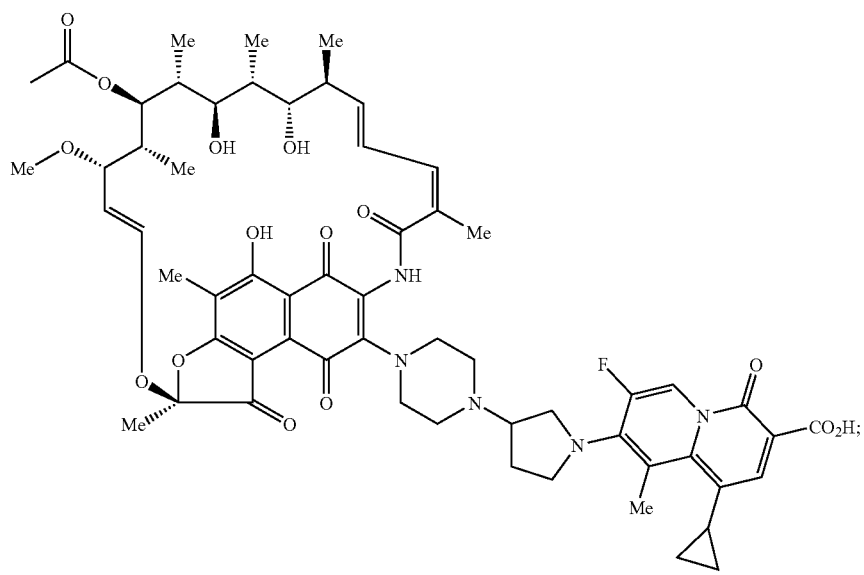

q. (R/S, S)-3-{3-[1-(3-Carboxy-1-cyclopropyl-7-fluoro-9-methyl-4-oxo-4H-quinolizin-8-yl)-pyrrolidin-3-ylamino]-piperidin-1-yl}-rifamycin S:
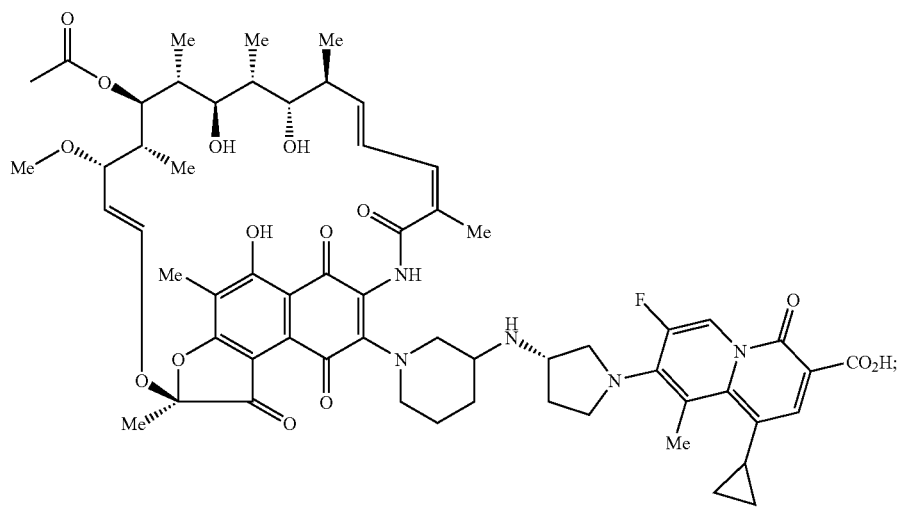
r. (S)-3-{4-[1-(3-Carboxy-1-cyclopropyl-7-fluoro-9-methyl-4-oxo-4H-quinolizine-8-yl)-pyrrolidin-3-ylamino]-piperidin-1-yl}-rifamycin S:
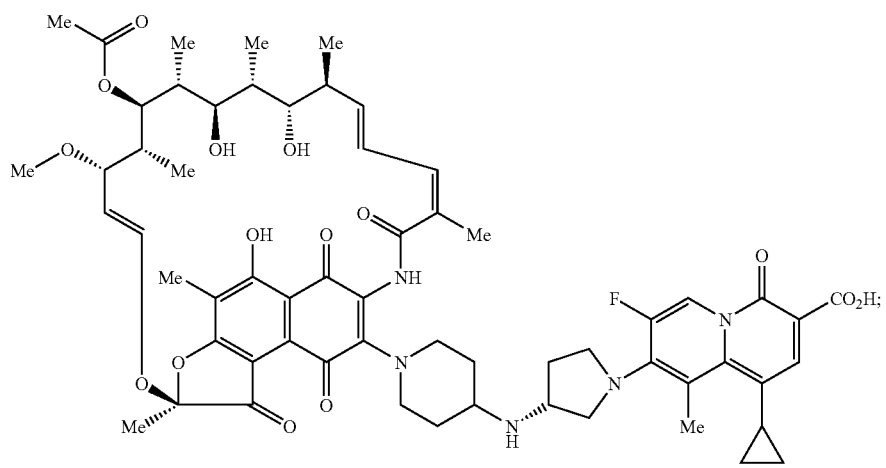

s. (R/S)-3-{4-[1-(3-Carboxy-1-cyclopropyl-7-fluoro-9-methyl-4-oxo-4H-quinolizine-8-yl)-pyrrolidin-3-ylamino]-piperidin-1-yl}-rifamycin S:
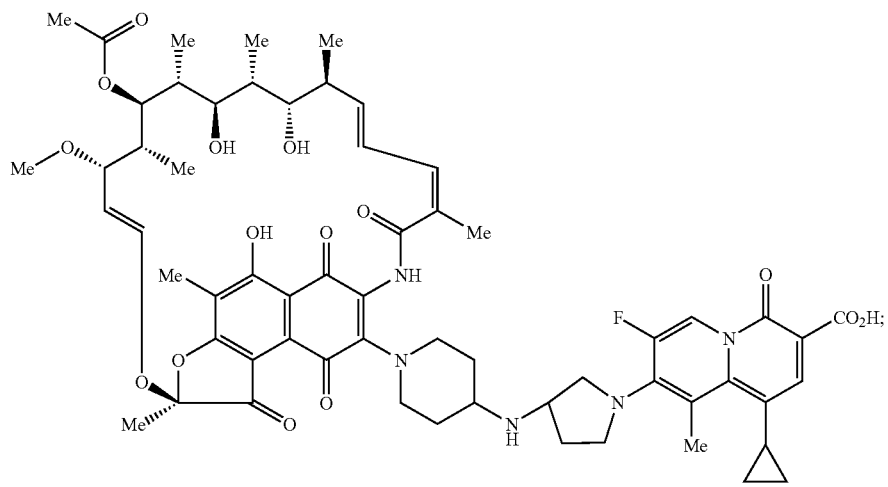
t. (R/S)-3-(4-{[1-(3-Carboxy-1-cyclopropl-7-fluoro-9-methyl-4-oxo-4H-quinolizine-8-yl)-pyrrolidin-3-yl]-(N-methyl-amino)}-piperidin-1-yl)-rifamycin S:
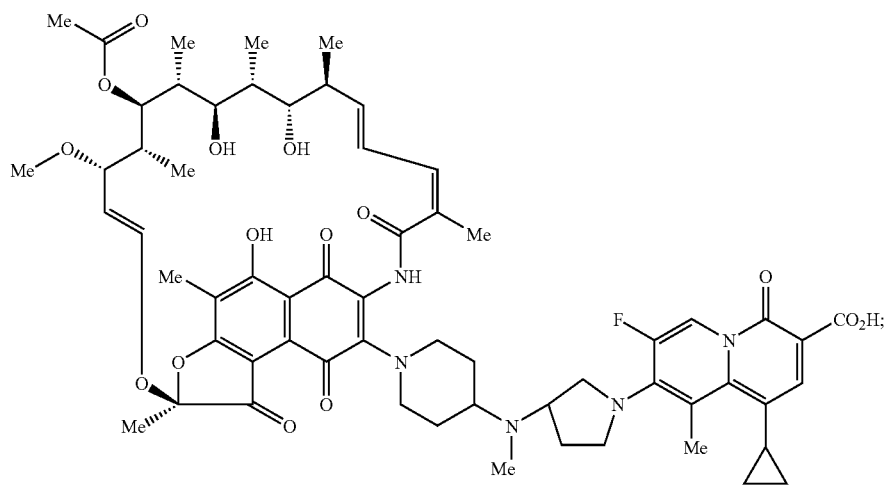

u. (R)-3-{4-[1-(3-Carboxy-1-cyclopropyl-7-fluoro-9-methyl-4-oxo-4H-quinolizin-8-yl)-pyrrolidin-3-yloxyimino]-piperidin-1-yl}-rifamycin S:
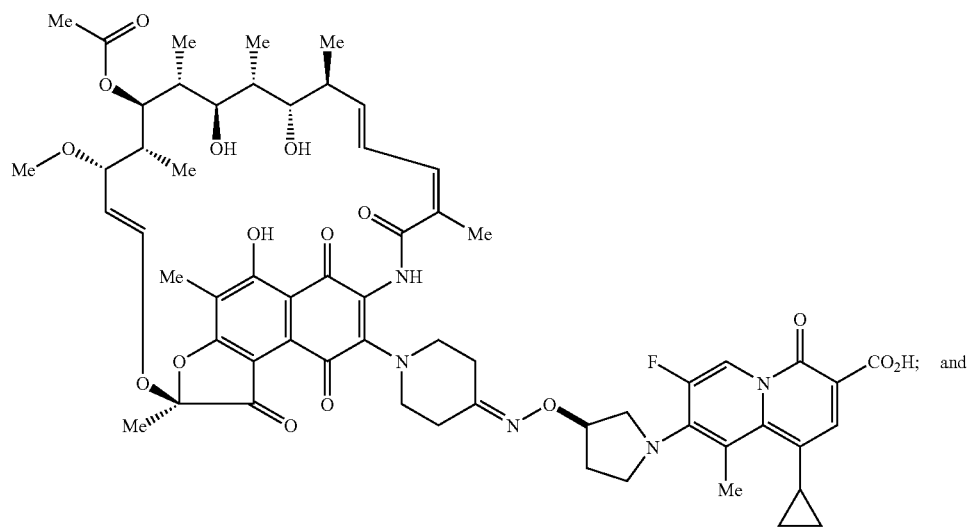
and
v. (S)-3-(4-{[1-(3-Carboxy-1-cyclopropyl-7-fluoro-9-methyl-4-oxo-4H-quinolizin-8-yl)-pyrrolidin-3-ylamino]-methyl}-piperidin-1-yl)-rifamycin S:
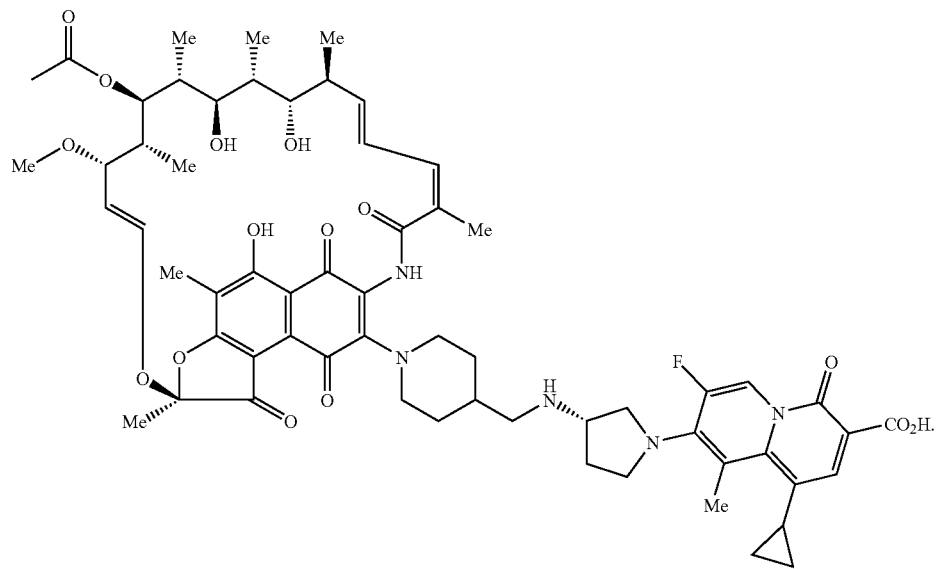

6. A compound having a formula selected from the group consisting of:
  a. (R/S)-3-{4-[1-(3-Carboxy-1-cyclopropyl-7-fluoro-9-methyl-4-oxo-4H-quinolizine-8-yl)-pyrrolidin-3-yl-methoxy]-piperidin-1-yl}-rifamycin S:
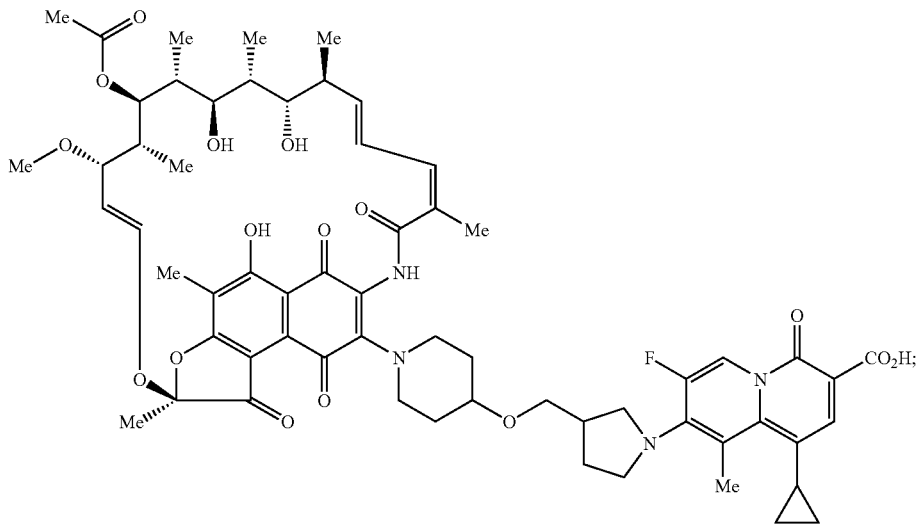
  b. (R/S)-3-(4-{[1-(3-Carboxy-1-cyclopropyl-7-fluoro-9-methyl-4-oxo-4H-quinolizine-8-yl)-pyrrolidin-3-ylmethyl]-methyl-amino}-piperidin-1-yl)-rifamycin S:
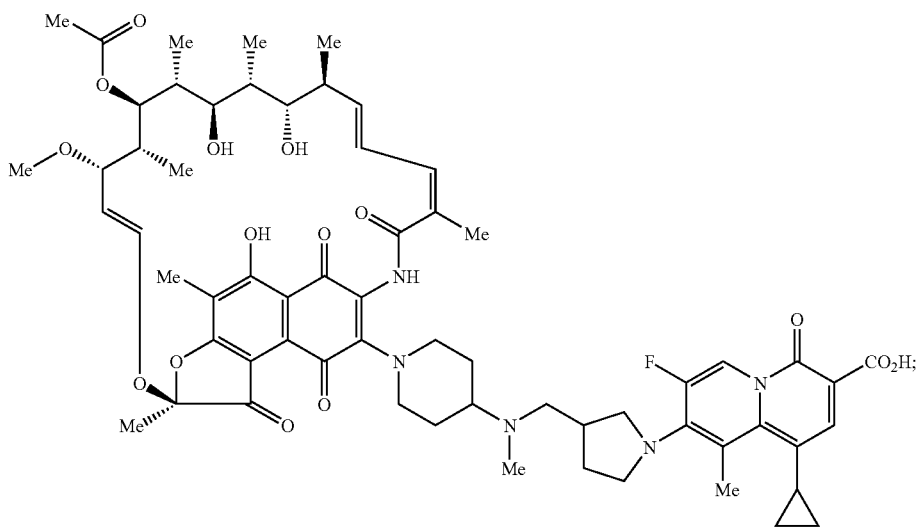

c. (R)-3-(4-{[1-(3-Carboxy-1-cyclopropyl-7-fluoro-9-methyl-4-oxo-4H-quinolizine-8-yl)-pyrrolidin-3-ylmethyl]-methyl-amino}-piperidin-1-yl)-rifamycin S:
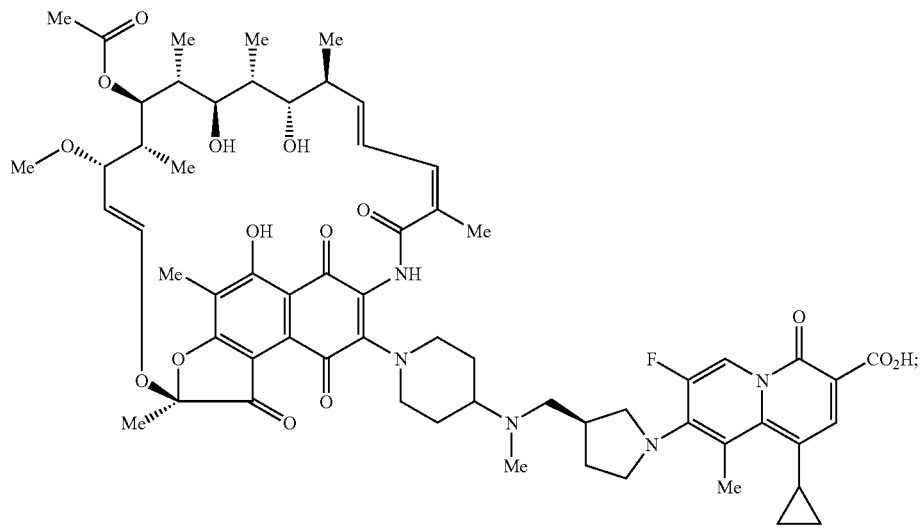
d. (R/S)-3-(4-{1-[1-(3-Carboxy-1-cyclopropyl-7-fluoro-9-methyl-4-oxo-4H-quinolizine-8-yl)-pyrrolidin-3-yl]-cyclopropylamino}-piperidin-1-yl)-rifamycin S:
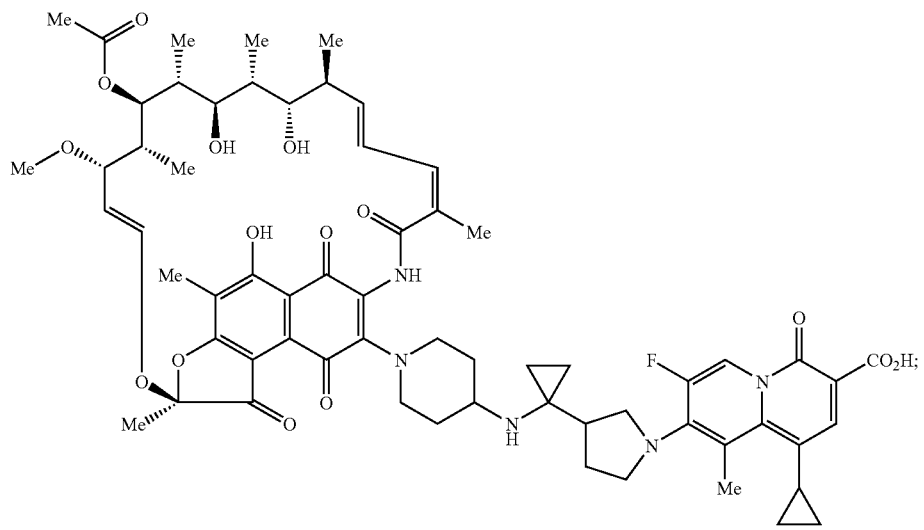

e. (R/S)-3-(4-{[1-(3-Carboxy-1-cyclopropyl-7-fluoro-9-methyl-4-oxo-4H-quinolizine-8-yl)-3-trifluoromethyl-pyrrolidin-3-ylmethyl]-amino}-piperidin-1-yl)-rifamycin S:
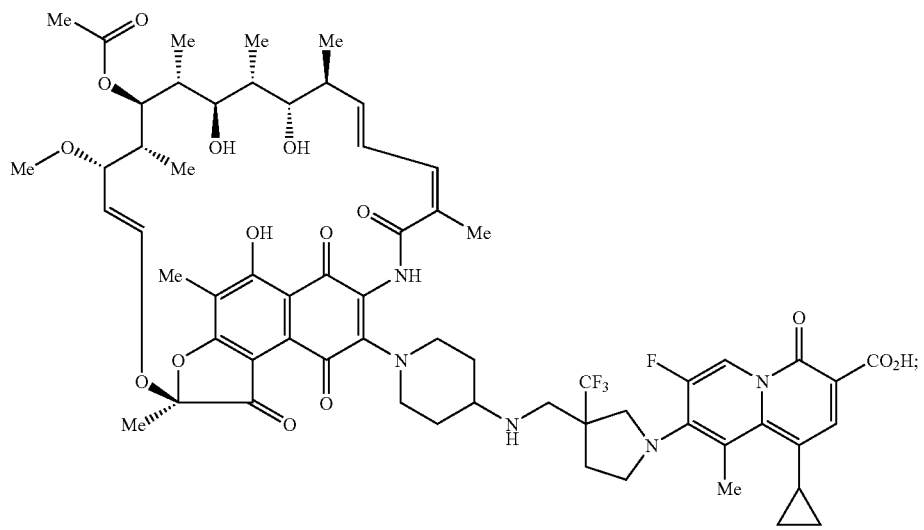
f. (R)-3-(4-{[1-(3-Carboxy-1-cyclopropyl-7-fluoro-9-methyl-4-oxo-4H-quinolizine-8-yl)-pyrrolidin-3-ylmethyl]-amino}-piperidin-1-yl)-rifamycin S:
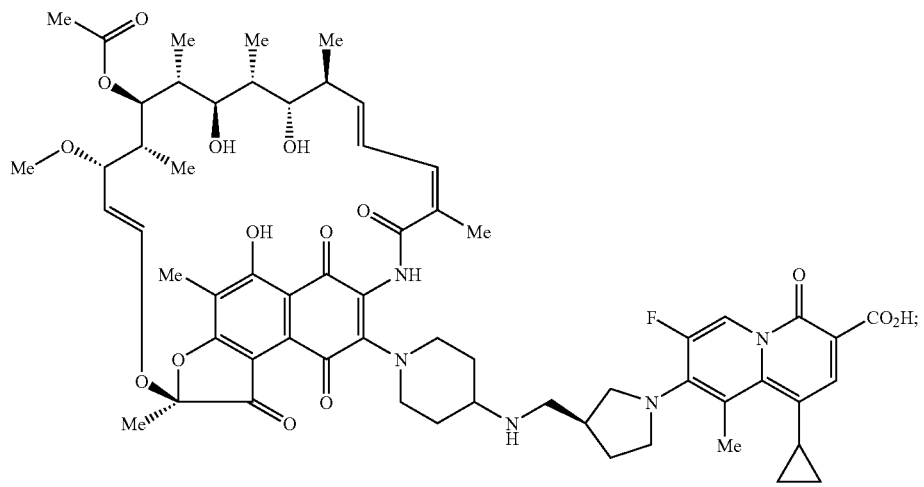

g. (R/S)-3-(4-{[1-(3-Carboxy-1-cyclopropyl-7-fluoro-9-methyl-4-oxo-4H-quinolizine-8-yl)-pyrrolidin-3-ylmethyl]-amino}-piperidin-1-yl)-rifamycin S:
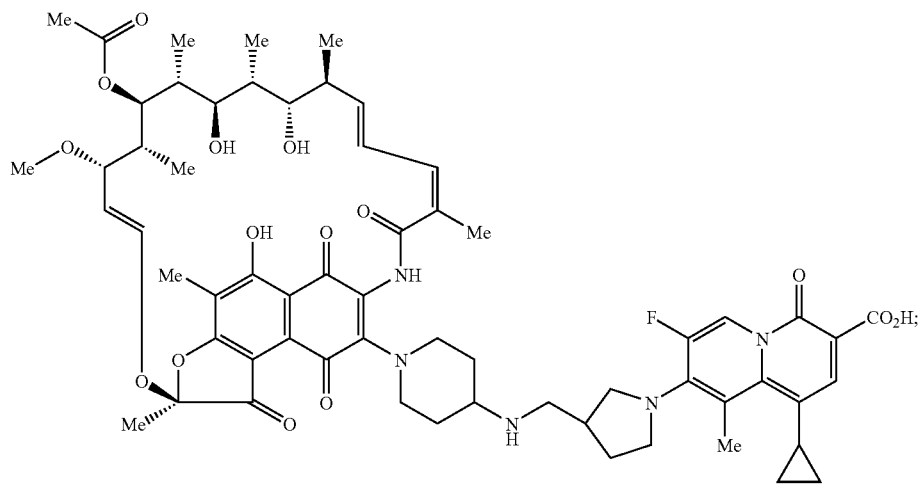
h. (S)-3-(4-{[1-(3-Carboxy-1-cyclopropyl-7-fluoro-9-methyl-4-oxo-4H-quinolizine-8-yl)-pyrrolidin-3-ylmethyl]-amino}-piperidin-1-yl)-rifamycin S:
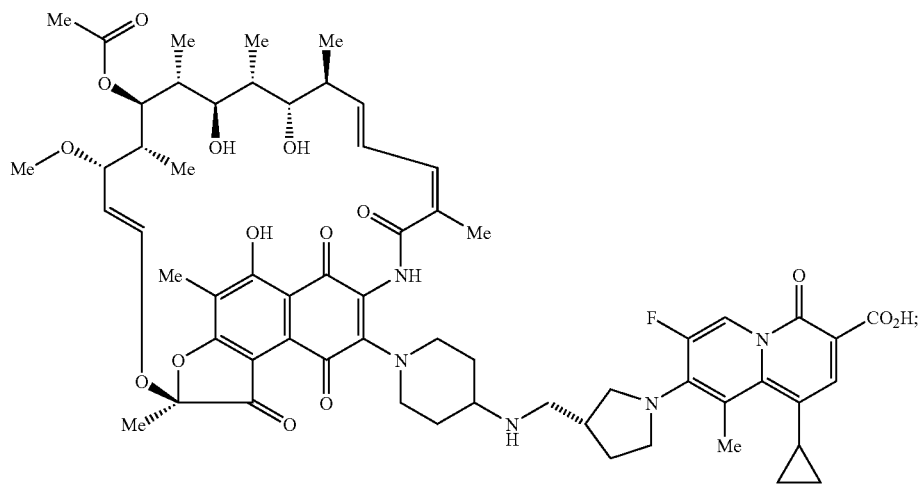

i. (R)-3-(4-{[1-(3-Carboxy-1-cyclopropyl-7-fluoro-9-methyl-4-oxo-4H-quinolizine-8-yl)-pyrrolidin-3-ylmethyl]-amino}-piperidin-1-yl)-rifamycin SV:

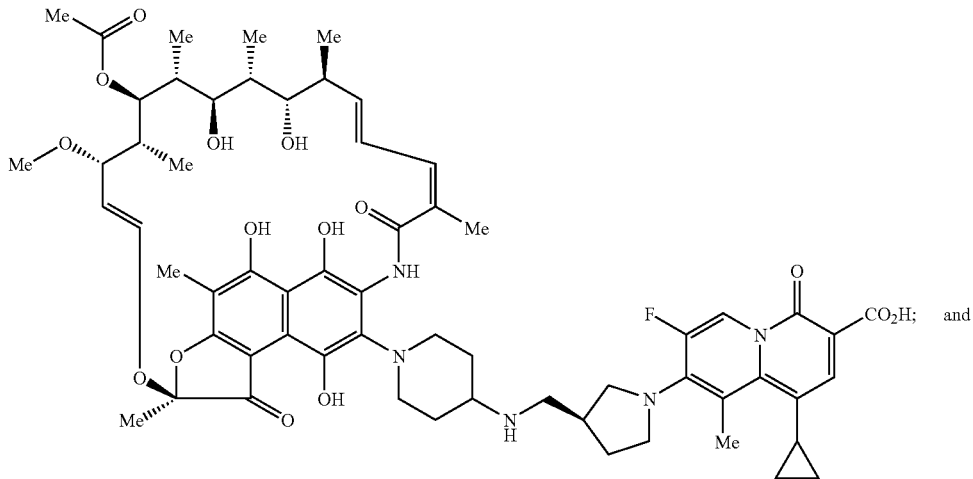

j. (R)-3-(4-{1-[1-(3-Carboxy-1-cyclopropyl-7-fluoro-9-methyl-4-oxo-4H-quinolizine-8-yl)-pyrrolidin-3-yl]-cyclopropylamino}-piperidin-1-yl)-rifamycin SV:

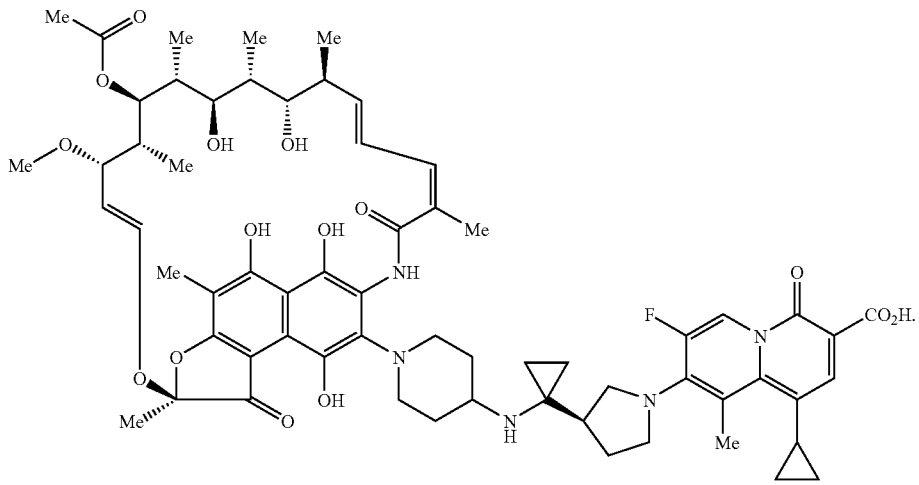

7. A compound having a formula selected from the group consisting of:

a. 3-{[4-(3-Carboxy-1-cyclopropyl-7-fluoro-9-methyl-4-oxo-4H-quinolizine-8-yl)-piperazin-1-yl-imino]-methyl}-rifamycin SV:

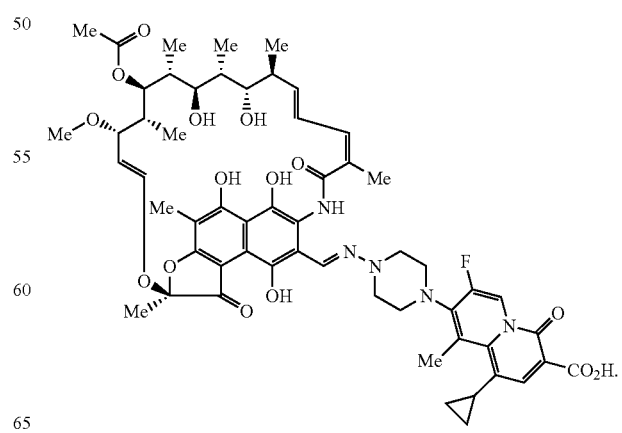

b. (R/S)-3-({4-[1-(3-Carboxy-1-cyclopropyl-7-fluoro-9-methyl-4-oxo-4H-quinolizine-8-yl)-pyrrolidin-3-ylm-ethyl]-piperazin-1-ylimino}-methyl)-rifamycin SV:
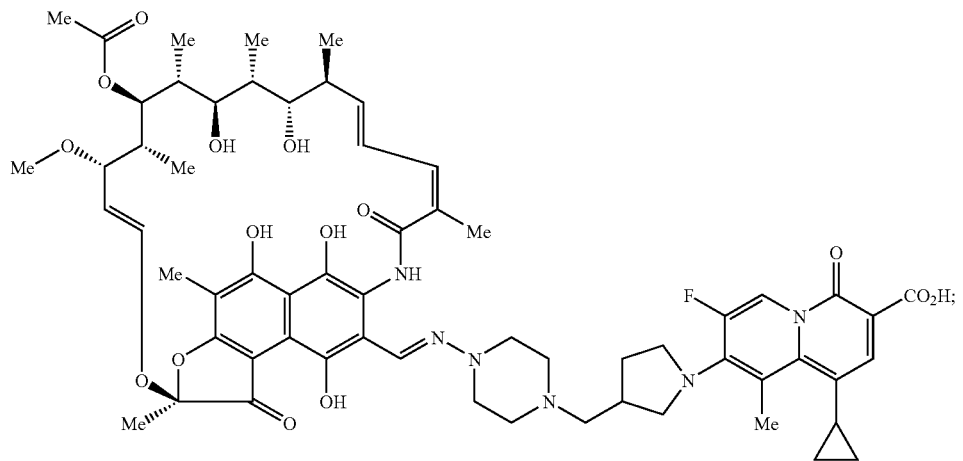
c. (S)-3-({4-[1-(3-Carboxy-1-cyclopropyl-7-fluoro-9-methyl-4-oxo-4H-quinolizine-8-yl)-pyrrolidin-3-yl-oxy-carbonyl]-piperazin-1-yl-imino}-methyl)-rifamycin SV:
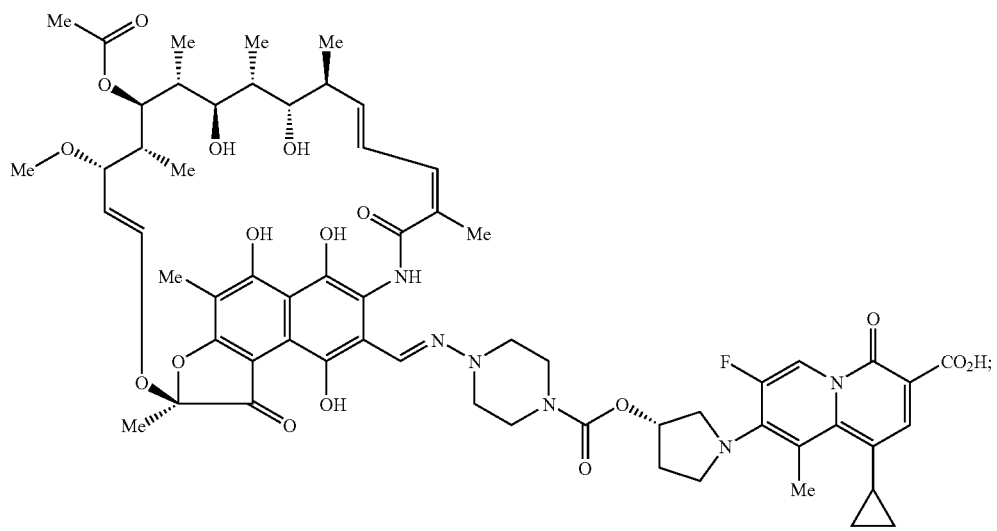

d. (R/S)-3-[(4-{[1-(3-Carboxy-1-cyclopropyl-7-fluoro-9-methyl-4-oxo-4H-quinolizine-8-yl)-pyrrolidin-3-ylmethyl]-methyl-amino}-piperidin-1-ylimino)-methyl]-rifamycin SV:
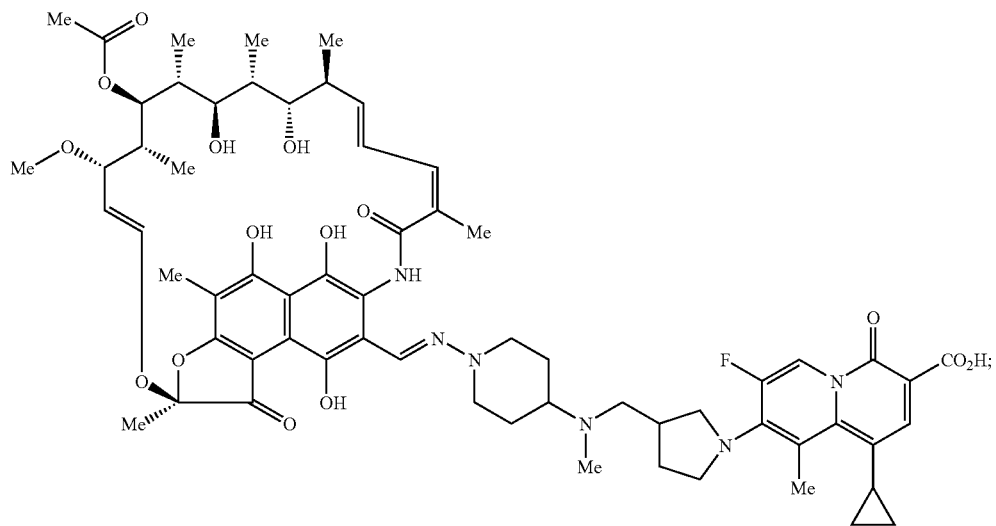
e. (R/S)-3-({4-[1-(3-Carboxy-1-cyclopropl-7-fluoro-9-methyl-4-oxo-4H-quinolizine-8-yl)-pyrrolidin-3-yl-methoxy]-piperidin-1-ylimino}-methyl)-rifamycin SV:
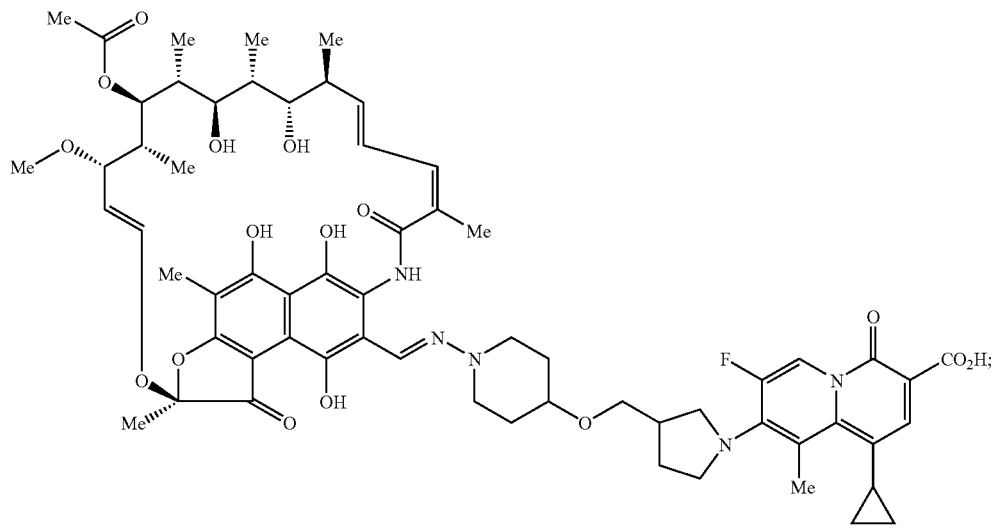

f. (S)-3-{[1-(3-Carboxy-1-cyclopropyl-7-fluoro-9-methyl-4-oxo-4H-quinolizine-8-yl)-pyrrolidin-3-yl]-hydrazinomethyl}-rifamycin SV:
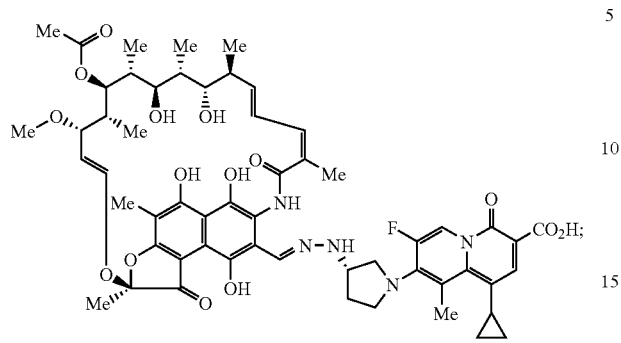
g. (R/S)-3 -{[1-(3-Carboxy-1-cyclopropyl-7-fluoro-9-methyl-4-oxo-4H-quinolizine-8-yl)-pyrrolidin-3-yl]-hydrazinomethyl}-rifamycin SV:
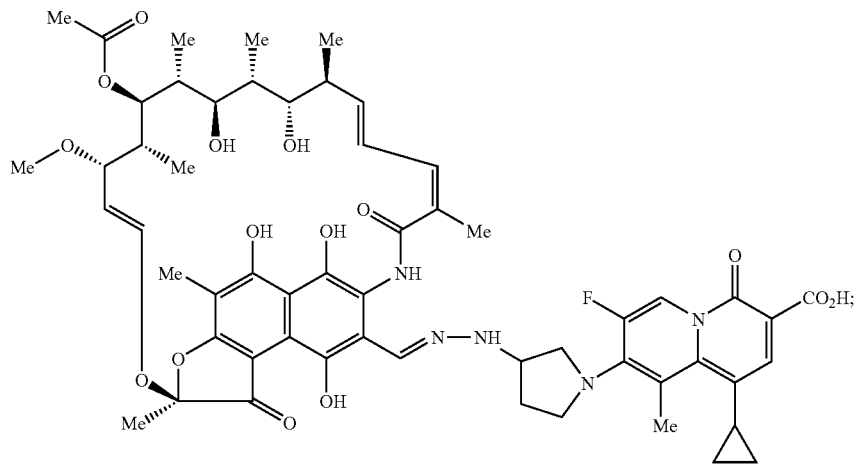
h. (R/S)-3-{[1-(3-Carboxy-1-cyclopropl-7-fluoro-9-methyl-4-oxo-4H-quinolizine-8-yl)-pyrrolidin-3-ylmethyl]-hydrazinomethyl}-rifamycin SV:
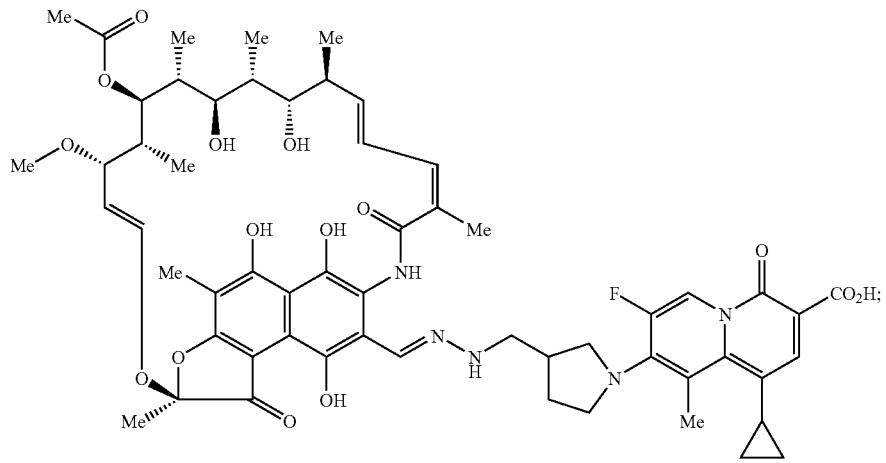

i. (R/S)-3-{[1-(3-Carboxy-1-cyclopropyl-7-fluoro-9-methyl-4-oxo-4H-quinolizine-8-yl)-pyrrolidin-3-yl]-(N-methyl-hydrazino)-methyl}-rifamycin SV:

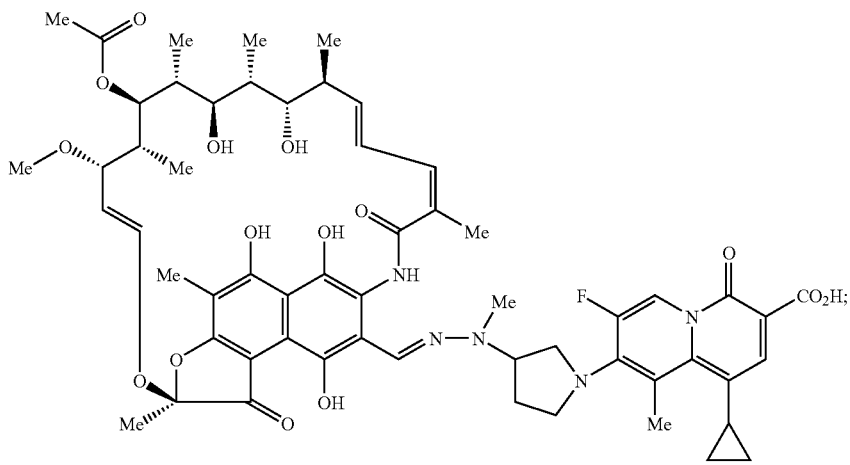

j. (R/S)-3-({3-[1-(3-Carboxy-1-cyclopropyl-7-fluoro-9-methyl-4-oxo-4H-quinolizine-8-yl)-piperidin-4-yl]-pyrrolidin-1-ylimino}-methyl)-rifamycin SV (2014) and (R/S)-3-({4-[1-(3-Carboxy-1-cyclopropyl-7-fluoro-9-methyl-4-oxo-4H-quinolizine-8-yl)-pyrrolidin-3-yl]-piperidin-1-ylimino}-methyl)-rifamycin SV (2015):

k. 3-{[5-(3-Carboxy-1-cyclopropyl-7-fluoro-9-methyl-4-oxo-4H-quinolizin-8-yl)-hexahydro-pyrrolo[3,4-c]pyrrol-2-ylimino]-methyl}-rifamycin SV: